(12) United States Patent
Alonso-Bedate et al.

(10) Patent No.: US 9,187,751 B2
(45) Date of Patent: Nov. 17, 2015

(54) ADJUVANT

(75) Inventors: Carlos Alonso-Bedate, Madrid (ES); Manuel Soto-Alvarez, Madrid (ES); Nuria Parody-De La Fuente, Alcobendas (ES); Yago Pico De Coana-Suarez, Madrid (ES)

(73) Assignee: LABORATORIOS LETI, S.L., Madrid (ES)

( * ) Notice: Subject to any disclaimer, the term of this patent is extended or adjusted under 35 U.S.C. 154(b) by 0 days.

(21) Appl. No.: 13/884,939

(22) PCT Filed: Nov. 10, 2011

(86) PCT No.: PCT/EP2011/069849
§ 371 (c)(1),
(2), (4) Date: Sep. 26, 2013

(87) PCT Pub. No.: WO2012/062861
PCT Pub. Date: May 18, 2012

(65) Prior Publication Data
US 2014/0030293 A1      Jan. 30, 2014

Related U.S. Application Data

(60) Provisional application No. 61/412,034, filed on Nov. 10, 2010.

(30) Foreign Application Priority Data

Nov. 10, 2010   (EP) .................................. 10190705

(51) Int. Cl.
*C12N 15/67*   (2006.01)
*C07K 14/44*   (2006.01)
*C07H 21/02*   (2006.01)
*A61K 39/00*   (2006.01)

(52) U.S. Cl.
CPC .............. *C12N 15/67* (2013.01); *C07K 14/44* (2013.01); *A61K 2039/55511* (2013.01); *C07H 21/02* (2013.01)

(58) Field of Classification Search
CPC ....... A61K 49/00; A61K 39/00; A61K 39/02; A61K 45/00; C07H 21/02; C07H 21/04

USPC ................. 424/9.1, 9.2, 184.1, 185.1, 192.1, 424/234.1, 278.1; 530/300, 350; 536/23.1, 536/23.7

See application file for complete search history.

(56) References Cited

U.S. PATENT DOCUMENTS 6,458,359 B1 * 10/2002 Bedate et al. ............... 424/192.1
2003/0138451 A1    7/2003 Alonso Bedate et al.
2005/0287176 A1   12/2005 Bedate et al.

OTHER PUBLICATIONS

Carcelen, J., et al., "The Chimerical Multi-Component Q Protein from Leistimania in the Absence of Adjunct Protects Dogs Against an Experimental Leishmania Infanturn Infection," Vaccine, vol. 27, No. 43, pp. 5964-5973 (Oct. 9, 2009).
Iniesta, V., et al ,"Leishmania Major Infection in Susceptible and Resistant Mice Elicit a Differential Humoral Response Against a Total Soluble Fraction and Defined Recombinant Antigens of the Parasite," Parasitology Research, vol. 102, No. 5, pp. 887-893 (Jan. 10, 2008).
McKierrian, Eadaoin, et al., "The Role of S100 Gene in Breast Cancer Progression," Tumor Biology, vol. 32, No. 3, pp. 441-450 (Jun. 2011).
Passos, S., et al "Recombinant Leishmania Antigens for Serodiagnosis of Visceral Leishmaniasis" Clinical and Diagnostic Laboratory Immunology, vol. 12, No. 10, pp. 1164-1167 (Oct. 2005).
Pedreira tie Carvalho, Lucas Pedreira, et al., "Characterization of the Immune Response to Leishmania Infantum Recombinant Antigens," Microbes and Infection, vol. 5, No. 1, pp. 7-12 (Jan. 2003).
Pico de Coana, Y., et al., "Molecular Cloning and Characterization of Cup a 4, a New Allergen from Cupressus Arizonica," Biochemical and Biophysical Research Communications, vol. 401, No. 3, pp. 451-457 (Oct. 22, 2010).
Requena, J., el al., "Immune and Clinical Parameters Associated with Leishmania Infantum Infection in the Golden Hamster Model," Veterinary Immunology and Immunopathology, Elsevier, vol. 76, No. 3-4, pp. 269-281 (Oct. 31, 2000).
Soto, Manuel, et al., "Multicomponent Chimeric Antigen for Serodiagnosis of Canine Visceral Leishmaniasis," Journal of Clinical Microbiology, American Society for Microbiology, vol. 36, No. 1, pp. 58-63 (Jan. 1, 1998).

\* cited by examiner

*Primary Examiner* — Rodney P Swartz
(74) *Attorney, Agent, or Firm* — Morgan, Lewis & Bockius LLP

(57) ABSTRACT

The invention relates to a new adjuvant and to its use in combination with an antigen.

16 Claims, 16 Drawing Sheets

Fig 4.1
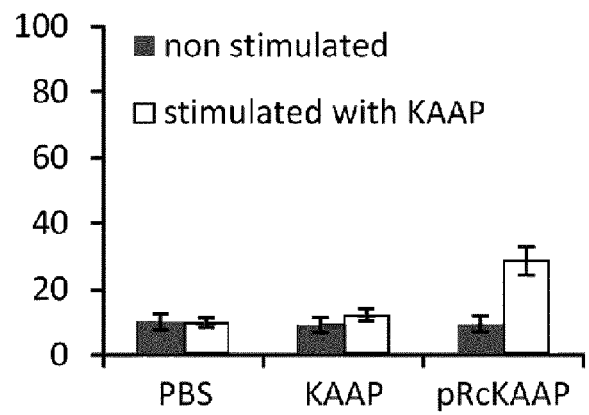
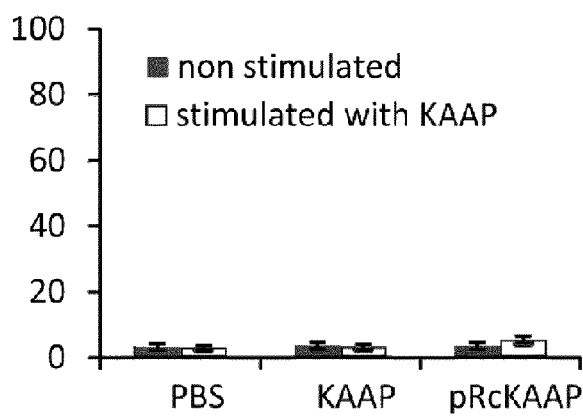
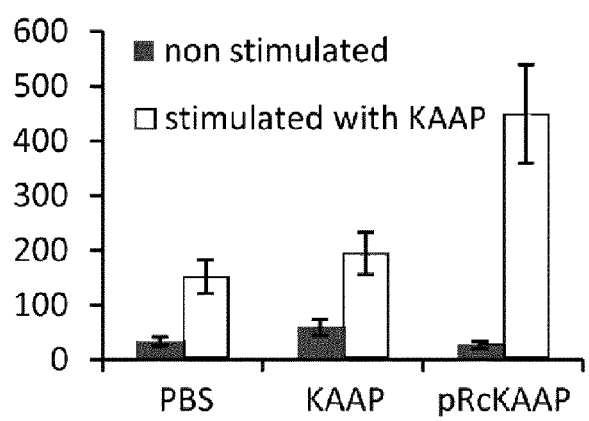

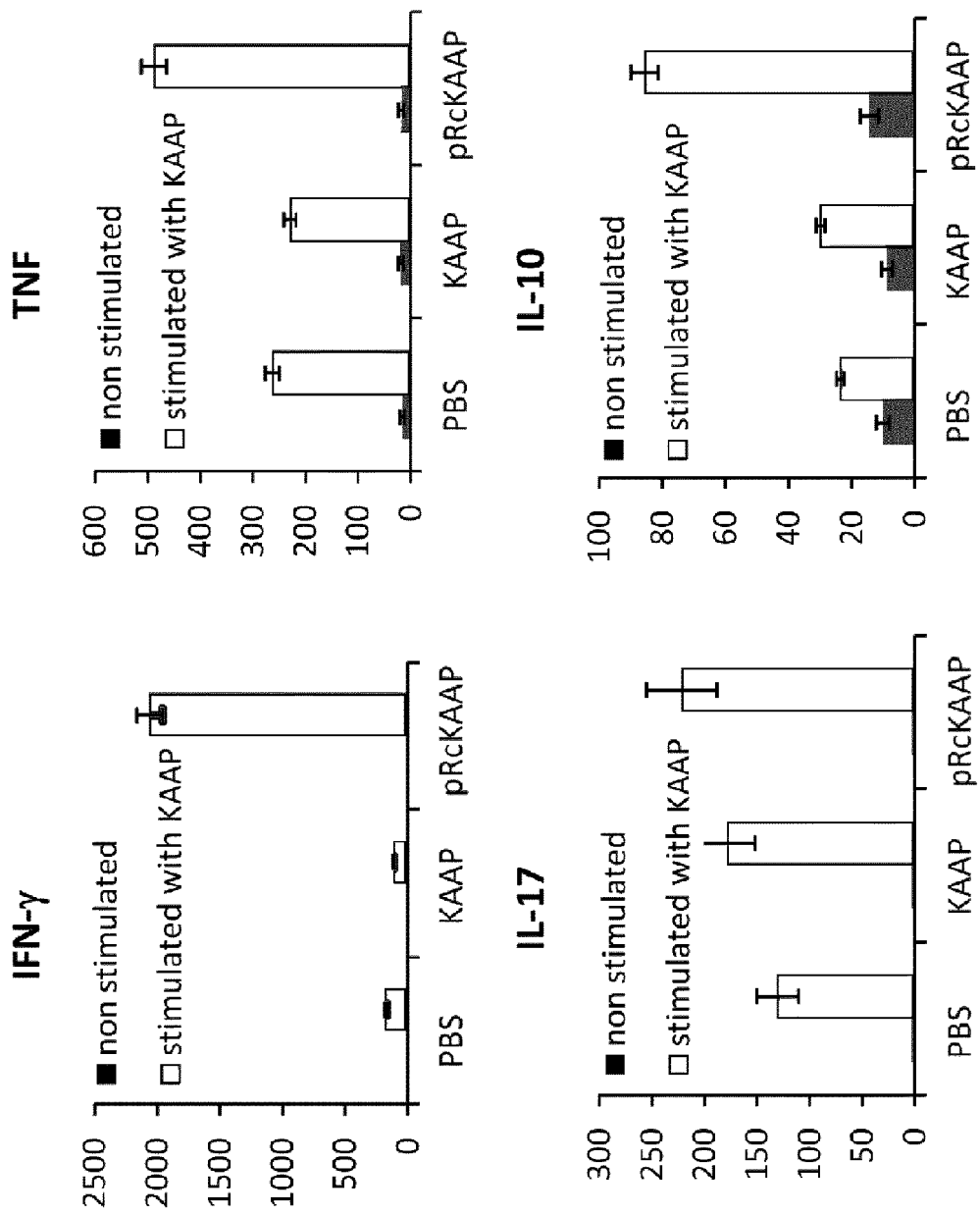
Fig 4.2

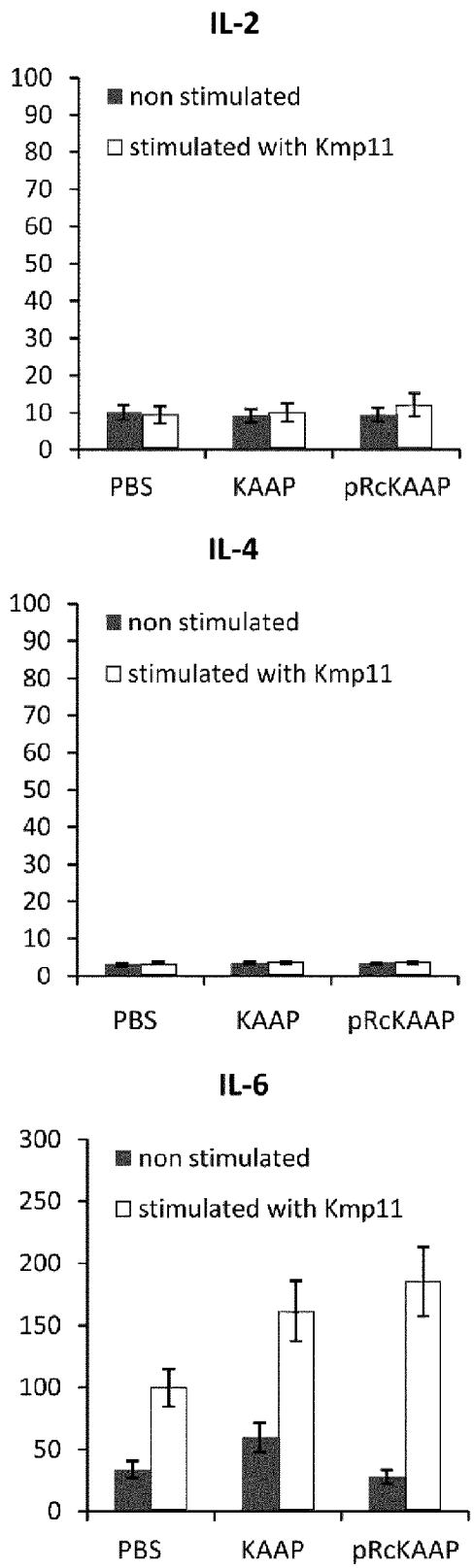
Fig 5.1

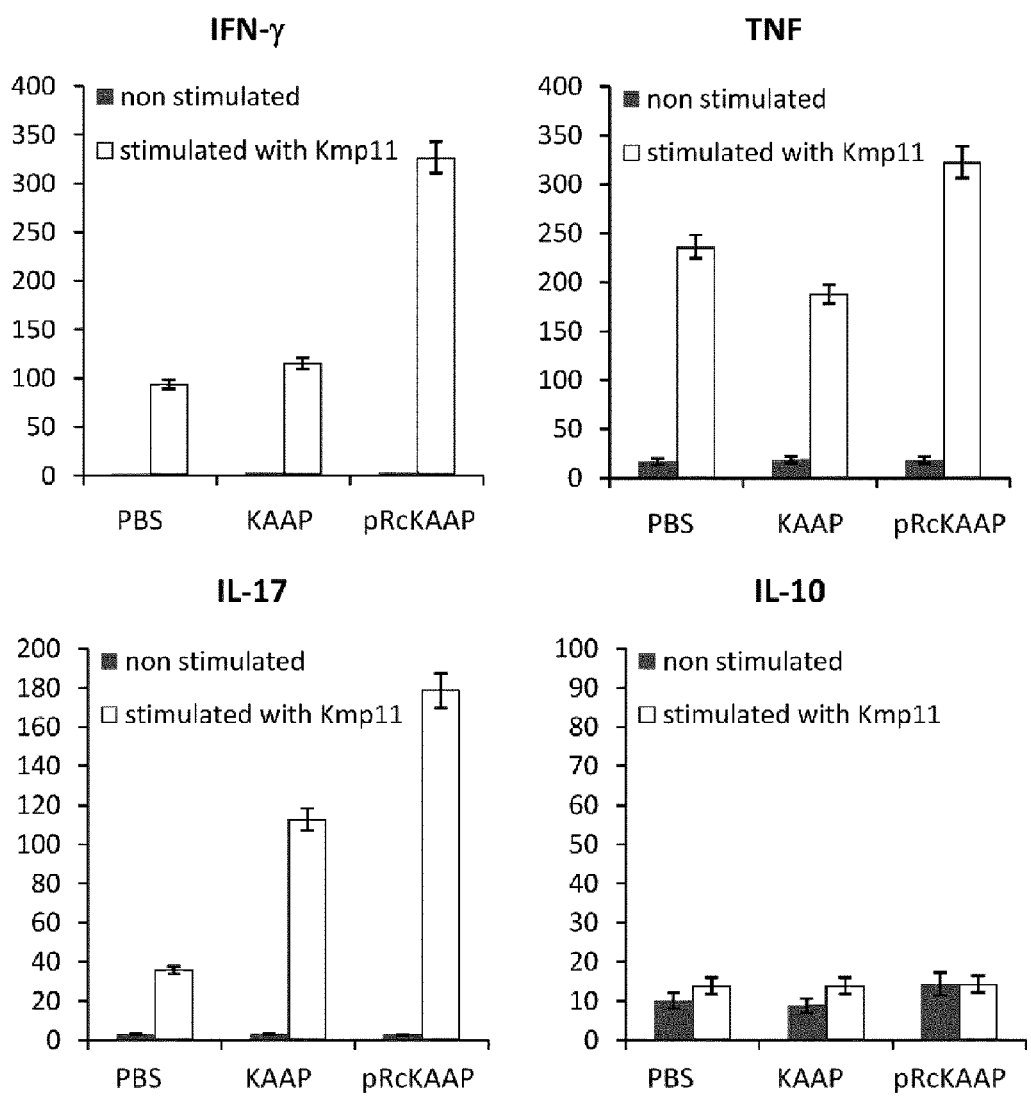
Fig 5.2

Fig 14  a
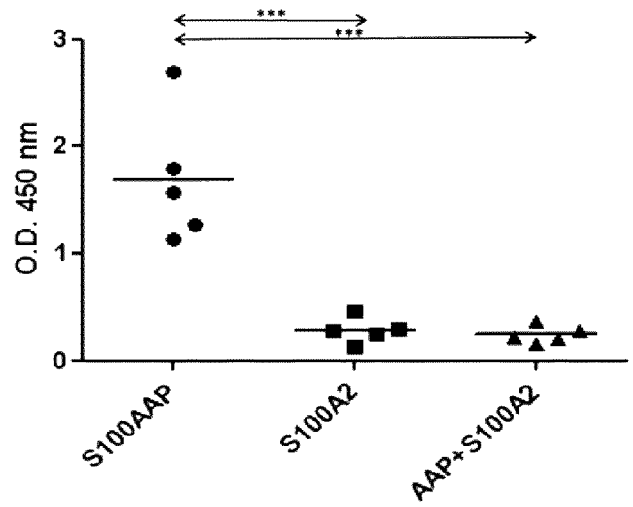
b IgG1
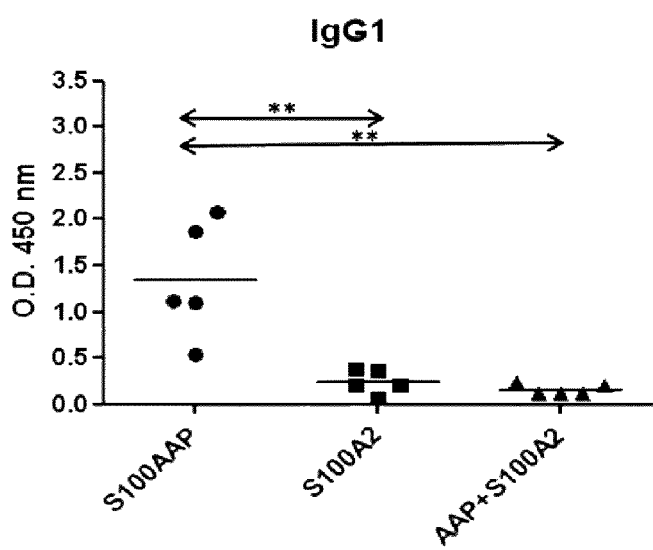
c IgG2a
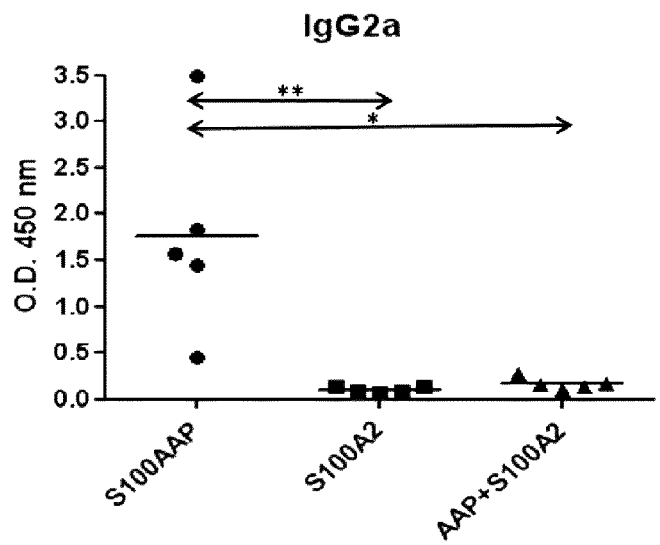

SEQUENCE LISTING

<160> NUMBER OF SEQ ID NOS: 47

<210> SEQ ID NO 1
<211> LENGTH: 254
<212> TYPE: PRT
<213> ORGANISM: Artificial
<220> FEATURE:
<223> OTHER INFORMATION: chimeric protein AAP - Augmentor and Activator
      Protein.

<400> SEQUENCE: 1

Gly Ser Ser Arg Pro Met Ser Thr Lys Tyr Leu Ala Ala Tyr Ala Leu
1               5                   10                  15

Ala Ser Leu Ser Lys Ala Ser Pro Ser Gln Ala Asp Val Glu Ala Ile
            20                  25                  30

Cys Lys Ala Val His Ile Asp Val Asp Gln Ala Thr Leu Ala Phe Val
        35                  40                  45

Met Glu Ser Val Thr Gly Arg Asp Val Ala Thr Leu Ile Ala Glu Gly
    50                  55                  60

Ala Ala Lys Met Ser Ala Met Pro Ala Ala Ser Ser Gly Ala Ala Ala
65                  70                  75                  80

Gly Val Thr Ala Ser Ala Ala Gly Asp Ala Ala Pro Ala Ala Ala Ala
                85                  90                  95

Ala Lys Lys Asp Glu Pro Glu Glu Glu Ala Asp Asp Met Gly Pro
            100                 105                 110

Ser Arg Val Asp Pro Met Gln Tyr Leu Ala Ala Tyr Ala Leu Val Ala
        115                 120                 125

Met Ser Gly Lys Thr Pro Ser Lys Ala Asp Val Gln Ala Val Leu Lys
    130                 135                 140

Ala Ala Gly Val Ala Val Asp Ala Ser Arg Val Asp Ala Val Phe Gln
145                 150                 155                 160

Glu Val Glu Gly Lys Ser Phe Asp Ala Leu Val Ala Glu Gly Arg Thr
                165                 170                 175

Lys Leu Val Gly Ser Gly Ser Ala Ala Pro Ala Gly Ala Val Ser Thr
            180                 185                 190

Ala Gly Ala Gly Ala Gly Ala Val Ala Glu Ala Lys Lys Glu Glu Pro 195                 200                 205
Glu Glu Glu Glu Ala Asp Asp Asp Met Gly Pro Val Asp Leu Gln Pro
                210                 215                 220
Ala Ala Ala Ala Pro Ala Ala Pro Ser Ala Ala Lys Glu Glu Pro
225                 230                 235                 240
Glu Glu Ser Asp Glu Asp Asp Phe Gly Met Gly Gly Leu Phe
                245                 250

<210> SEQ ID NO 2
<211> LENGTH: 765
<212> TYPE: DNA
<213> ORGANISM: Artificial
<220> FEATURE:
<223> OTHER INFORMATION: pAAP - nucleotide sequence encoding protein
      AAP - Augmentor and Activator Protein.

<400> SEQUENCE: 2
ggatcctcta gacccatgtc caccaagtac ctcgccgcgt acgctctggc ctccctgagc    60
aaggcgtccc cgtctcaggc ggacgtggag gctatctgca aggccgtcca catcgacgtc   120
gaccaggcca ccctcgcctt tgtgatggag agcgttacgg gacgcgacgt ggccaccctg   180
atcgcggagg gcgccgcgaa gatgagcgcg atgccggcgg ccagctctgg tgccgctgct   240
ggcgtcactg cttccgctgc gggtgatgcg gctccggctg ccgccgctgc taagaaggac   300
gagccggagg aggaggccga cgacgacatg ggcccctcta gagtcgaccc catgcagtac   360
ctcgccgcgt acgccctcgt ggcgatgtct ggcaagacgc cgtcgaaggc ggacgttcag   420
gctgtcctga aggccgccgg cgttgccgtg atgcctccc gcgtggatgc cgtcttccag   480
gaggtggagg gcaagagctt cgatgcgctg gtggccgagg ccgcacgaa gctggtgggc   540 tctggctctg ccgctcctgc tggcgctgtc tccactgctg gtgccggcgc tggcgcggtg   600
gccgaggcga agaaggagga gcccgaggag gaggaggccg atgatgacat gggcccccgtc   660 gacctgcagc ccgccgctgc cgcgccggcc gcccctagcg ccgctgccaa ggaggagccg   720
gaggagagcg acgaggacga cttcggcatg ggcggtctct ctaa              765

<210> SEQ ID NO 3
<211> LENGTH: 132
<212> TYPE: PRT
<213> ORGANISM: Leishmania infantum

<400> SEQUENCE: 3

Met Ala Thr Pro Arg Ser Ala Lys Lys Ala Val Arg Lys Ser Gly Ser
1               5                   10                  15

Lys Ser Ala Lys Cys Gly Leu Ile Phe Pro Val Gly Arg Val Gly Gly
                20                  25                  30

Met Met Arg Arg Gly Gln Tyr Ala Arg Ile Gly Ala Ser Gly Ala
            35                  40                  45

Val Tyr Leu Ala Ala Val Leu Glu Tyr Leu Thr Ala Glu Leu Leu Glu
        50                  55                  60

Leu Ser Val Lys Ala Ala Ala Gln Ser Gly Lys Lys Arg Cys Arg Leu
65                  70                  75                  80

Asn Pro Arg Thr Val Met Leu Ala Ala Arg His Asp Asp Ile Gly
                85                  90                  95

Thr Leu Leu Lys Asn Val Thr Leu Ser His Ser Gly Val Val Pro Asn
            100                 105                 110

Ile Ser Lys Ala Met Ala Lys Lys Lys Gly Gly Lys Lys Gly Lys Ala
        115                 120                 125

Thr Pro Ser Ala
    130

<210> SEQ ID NO 4
<211> LENGTH: 691
<212> TYPE: DNA
<213> ORGANISM: Leishmania infantum

<400> SEQUENCE: 4
gcctcatccg tcatccgtca tctttgtgct acagctttac tctcactccc ctccaaccta      60
cccatcgcag ccatggctac tcctcgcagc gccaagaagg ccgtccgcaa gagcggctcc     120
aagtccgcga aatgtggtct gatcttcccg gtgggccgcg tcggcgggat gatgcgccgc     180
ggccagtacg ctcgccgcat cggtgcctct ggcgccgtgt acctggccgc cgtgctggag     240
tacctgacgg cggagctgct ggagctgtcc gtgaaggcgg ccgcgcagag cgggaagaag     300
cggtgccgcc tgaacccgcg caccgtgatg ctggccgcgc gccacgacga cgacatcggc     360
acgcttctga agaacgtgac cttgtctcac agcggcgttg tgccgaacat cagcaaggcg     420
atggcaaaga agaagggcgg caagaagggc aaggcgacac cgagcgcgta agtcctccgg     480
cctgacagcg cacacgcgcc gctgtattgt gcgcgtgcgc gcgggtcccg actggggccg     540
gcgatgaggc gcatcatacc tccatagaga ccctatcttt tgttttatgg cttctcagat     600
gaccacttgg ttcttcctgc ctttgtttgg tttgttttct cctcccctc cgccgagggt      660 acgagtcagg gtaggctcgg acaaaaaaaa a                                    691

<210> SEQ ID NO 5
<211> LENGTH: 111
<212> TYPE: PRT
<213> ORGANISM: Leishmania infantum

<400> SEQUENCE: 5

Met Ala Ser Ser Arg Ser Ala Pro Arg Lys Ala Ser His Ala His Lys
1               5                   10                  15

Ser His Arg Lys Pro Lys Arg Ser Trp Asn Val Tyr Val Gly Arg Ser
            20                  25                  30

Leu Lys Ala Ile Asn Ala Gln Met Ser Met Ser His Arg Thr Met Ser
        35                  40                  45

Ile Val Asn Ser Tyr Val Asn Asp Val Met Glu Arg Ile Cys Met Glu
    50                  55                  60

Ala Ala Ser Ile Val Arg Ala Asn Lys Lys Arg Thr Leu Gly Ala Arg
65                  70                  75                  80

Glu Val Gln Thr Ala Val Arg Ile Val Leu Pro Ala Glu Leu Ala Lys
                85                  90                  95

His Ala Met Ala Glu Gly Thr Lys Ala Val Ser Ser Ala Ser Ala
            100                 105                 110

<210> SEQ ID NO 6
<211> LENGTH: 894
<212> TYPE: DNA
<213> ORGANISM: Leishmania infantum

<400> SEQUENCE: 6
ccaagccagc caaatccttc gcactttcac gctgtccctc ctttccaacc aacccacatc      60
accatggcct cttctcgctc tgctccccgc aaggcttccc acgcgcacaa gtcgcaccgc     120
aagccgaagc gctcgtggaa cgtgtacgtg ggccgctcgc tgaaggcgat caacgcccag     180

```
atgtcgatgt cgcaccgcac gatgagcatc gtgaactcgt acgtgaacga cgtgatggag    240
cgcatctgca tggaggccgc gtcgatcgtt cgcgcgaaca agaagcgcac gttgggtgcg    300
cgcgaggtgc agacggcggt gcgcattgtg ctgccggcgg agctcgcgaa gcacgccatg    360
gctgagggca cgaaggccgt gtcgagcgcg tcggcttgag cggctcagtt agagggtttg    420
tccacgcctc ggccgtgtgt ccggggtgtg gggtaccctc aactcccctc tccccgccta    480
cgccgtgggt tttcatagag atttattgtt tcttttcga ttctctttcc ttgaaggtga    540
tgtctcgtcc tttgctggag tgcgtgccgg gttcgcgggc ggtagaaagc agcggcggag    600
gaggcagcgg cggcgcgaga cggtgaaggg gaggagaggc gggccgaaag cacagatgcg    660
cttctccgtc tctttctccc ttctctgcat tcgccctcgc tgctcctctc tgatgccctc    720
gtacctcgtg gtgcgcgcgt ctcccgctcg ccgtccgcgc cacgctgcac agaggcgtgc    780
acggtttgtc ttctatctca gaacgagtga cacacacgtt ttcttgttcc ccctccccc    840 cttcgtcatc gcttcttcgt tttcgttgtc gtctcgacgc ccaaaaaaaa aaaa          894
```

<210> SEQ ID NO 7
<211> LENGTH: 129
<212> TYPE: PRT
<213> ORGANISM: Leishmania infantum
<400> SEQUENCE: 7

```
Met Ser Arg Thr Lys Glu Thr Ala Arg Ala Lys Arg Thr Ile Thr Ser
1               5                   10                  15

Lys Lys Ser Lys Lys Ala Pro Ser Gly Ala Ser Gly Val Lys Arg Ser
            20                  25                  30

His Arg Arg Trp Arg Pro Gly Thr Cys Ala Ile Arg Glu Ile Arg Lys
        35                  40                  45

Phe Gln Lys Ser Thr Ser Leu Leu Ile Gln Cys Ala Pro Phe Gln Arg
    50                  55                  60

Leu Val Arg Gly Val Glu Arg Gln Lys Glu Gly Leu Arg Phe Gln Ser
65                  70                  75                  80

Ser Ala Ile Met Ala Leu Gln Glu Ala Thr Glu Ala Tyr Ile Val Ser
                85                  90                  95

Leu Met Ala Asp Thr Asn Leu Ala Cys Ile His Ala Lys Arg Val Thr
            100                 105                 110

Ile Gln Pro Lys Asp Ile Gln Leu Ala Leu Arg Leu Arg Gly Glu Arg
        115                 120                 125

His
```

<210> SEQ ID NO 8
<211> LENGTH: 587
<212> TYPE: DNA
<213> ORGANISM: Leishmania infantum
<400> SEQUENCE: 8

```
gtttcactac cgccatccaa cccctgcca ctcccacccc caccgcacca ccatgtcccg      60
caccaaggag accgcccgcg cgaagcgcac catcacgtcg aagaagagca agaaggcgcc    120
gagcggggcg tccggcgtga agaggtcgca tcgccgctgg cgcccgggca cctgcgcgat    180
ccgcgagatc cgcaagttcc agaagagtac gagcctgctg atccagtgcg cgccgttcca    240
gcgcctggtg cgaggtgtcg agcggcagaa ggagggcctg cgcttccaga gcagcgctat    300
catggcgctg caggaggcga cggaggcgta cattgtgtcg ctgatggcgg acacgaacct    360
cgcctgcatc cacgcgaagc gcgtgacgat ccagccgaag gacatccagc tggcgctgcg    420
```

```
cctgcgcggt gagcgccact agggcgggcc cgctctcccc ccctcatag ataccatgtt    480 tttgtttcct ttcttttcgc cttccctaag tcgtgcacgc tgccctgccg cggcagccga    540
gagagtgaga gggtcattga acctctagag cccgccaaaa aaaaaaa                  587
```

<210> SEQ ID NO 9
<211> LENGTH: 100
<212> TYPE: PRT
<213> ORGANISM: Leishmania infantum

<400> SEQUENCE: 9

```
Met Ala Lys Gly Lys Arg Ser Thr Asp Ala Lys Gly Ser Gln Arg Arg
1               5                   10                  15

Gln Lys Lys Val Leu Arg Asp Asn Ile Arg Gly Ile Thr Arg Gly Cys
                20                  25                  30

Val Arg Arg Met Ala Arg Arg Gly Gly Val Lys Arg Ile Ser Thr Glu
            35                  40                  45

Val Tyr Glu Glu Val Arg Arg Val Leu Lys Ala Tyr Val Glu Asp Ile
        50                  55                  60

Val Arg Cys Ser Thr Ala Tyr Thr Glu Tyr Ala Arg Lys Lys Thr Val
65                  70                  75                  80

Thr Ala Cys Asp Val Val Thr Ala Leu Arg Lys Gln Gly His Ile Leu
                85                  90                  95

Tyr Gly Tyr Ala
            100
```

<210> SEQ ID NO 10
<211> LENGTH: 531
<212> TYPE: DNA
<213> ORGANISM: Leishmania infantum

<400> SEQUENCE: 10

```
gctccctttc ttgcctcctc tccccccac gcctcctccc ttcacatatc caccatggcc     60
aagggcaagc gttccactga tgccaagggc agccagaggc gccagaagaa ggtgctgcgc   120
gacaacatcc gcggcatcac tcgcggctgc gtccgccgca tggcgcgccg cggtggcgtg   180
aagcgcatct cgaccgaggt gtacgaagag gtgcgccgtg tgctgaaggc ctacgtggag   240
gacattgtgc gctgcagcac ggcctacacc gagtacgcgc gcaagaagac cgtgacggcg   300
tgcgatgttg tgaccgcgct gcgcaagcaa ggccacatcc tgtacggcta cgcgtaaatg   360
ctcgcagagc cgctgcacac tcatagatac accttctttg ttcatgccgt cgtttcgttg   420
gctttcttgg ttttcgactt cccttccccc cactatggct tttctttcgt ctcgtgctgg   480
cacccttccc tactcatcgc tgtttgctga aggcagtaca gaacgaagcg g            531
```

<210> SEQ ID NO 11
<211> LENGTH: 323
<212> TYPE: PRT
<213> ORGANISM: Leishmania infantum

<400> SEQUENCE: 11

```
Met Pro Ser Ile Thr Thr Ala Lys Arg Glu Tyr Glu Glu Arg Leu Val
1               5                   10                  15

Asp Cys Leu Thr Lys Tyr Ser Cys Val Leu Phe Val Gly Met Asp Asn
                20                  25                  30

Val Arg Ser Gln Gln Val His Asp Val Gly Arg Ala Leu Arg Ala Lys
            35                  40                  45
```

```
Ala Glu Phe Met Met Gly Lys Lys Thr Leu Gln Gly Lys Ile Val Glu
 50                  55                  60

Lys Arg Ala Gln Ala Lys Asp Ala Ser Pro Glu Ala Lys His Phe Asn
 65                  70                  75                  80

Asp Gln Cys Glu Glu Tyr Asn Leu Leu Ser Gly Asn Thr Gly Leu Ile
                 85                  90                  95

Phe Thr Asn Asn Ala Val Gln Glu Ile Thr Ser Val Leu Asp Ala His
             100                 105                 110

Arg Val Lys Arg Ala Ala Arg Val Gly Ala Ile Ser Pro Cys Asp Val
             115                 120                 125

Ile Val Ala Ala Gly Ser Thr Gly Met Glu Pro Thr Gln Thr Ser Phe
130                 135                 140

Phe Gln Ala Leu Asn Ile Ala Thr Lys Ile Ala Lys Gly Met Val Glu
145                 150                 155                 160

Ile Val Thr Glu Lys Lys Val Leu Ser Val Gly Asp Lys Val Asp Asn
                 165                 170                 175

Ser Thr Ala Thr Leu Leu Gln Lys Leu Asn Ile Ser Pro Phe Tyr Tyr
             180                 185                 190

Gln Val Asn Val Leu Ser Val Trp Asp Arg Gly Val Leu Phe Thr Arg
             195                 200                 205

Glu Asp Leu Met Met Thr Glu Asp Met Val Glu Lys Met Leu Met Glu
210                 215                 220

Gly Leu Ser Asn Val Ala Met Ala Leu Gly Ala Gly Ile Pro Thr
225                 230                 235                 240

Ser Ser Thr Ile Gly Pro Met Leu Val Asp Ala Phe Lys Asn Leu Leu
                 245                 250                 255

Ala Val Ser Val Ala Thr Ser Tyr Glu Phe Glu Glu His Asn Gly Lys
             260                 265                 270

Glu Leu Arg Glu Ala Ala Ile Asn Gly Leu Leu Ala Gly Ser Cys Ser
             275                 280                 285

Ala Ala Ala Glu Pro Ala Ala Ala Pro Ala Ala Pro Ser Ala Ala
290                 295                 300

Ala Lys Glu Glu Pro Glu Glu Ser Asp Glu Asp Asp Phe Gly Met Gly
305                 310                 315                 320

Gly Leu Phe

<210> SEQ ID NO 12
<211> LENGTH: 3790
<212> TYPE: DNA
<213> ORGANISM: Leishmania infantum

<400> SEQUENCE: 12
atgcgcgcgc gcgcgcgaga gagcatgtat ccctgcgtgc cttcaatgga gacttgacac      60
ccctcttctc tgctctctgc tttctgctcc gtccctaat taccttgact gccttttact     120
tgttcccttt ctatttcctc gggttttggc aaccttcctt atgcgcccaa cacccacaac     180 ataccacc caaatcgtt gcttcacggc ctcccctcgt gctttgcagc tccctttagc     240
aacgatgccg tctatcacca ctgccaagcg cgagtacgag gagcgcctcg tcgactgcct     300
gaccaagtac agctgcgtgc tgttcgtggg catggacaac gtccgctcgc agcaggtgca     360
cgatgtcggc cgtgcgctgc gcgcgaaggc cgagttcatg atgggcaaga agacgctgca     420
gggcaagatc gtggagaagc gcgcgcaagc caaggacgcg agcccgagg cgaagcactt     480 caacgatcag tgtgaggagt acaacctgct gagcggcaac accggcctca tcttcacgaa     540
```

-continued

```
caacgctgtc caggagatca cgtctgtgct tgacgcgcac cgcgtgaagc gcgcggcgcg     600
tgtcggagcg atttccccgt gtgacgtgat tgtcgctgct ggcagcaccg gcatggagcc     660
gacccagacg tccttcttcc aggcgctgaa cattgcgacg aagattgcca agggtatggt     720
ggagatcgtg acgagaaga aggtgctgag cgtcggcgac aaggtggaca actcgacggc      780
gacgctgctg caaaagctga acatcagccc gttctactac caggtgaatg tgctgtccgt     840
gtgggaccgc ggtgtgctgt tcacccgcga ggacctgatg atgacggagg acatggtgga     900
gaagatgctg atggaaggcc tgagcaacgt tgcggcgatg gcgctgggtg ctggcatccc     960
gacgtcttcg acgattggcc cgatgctggt ggacgccttc aagaacctgc tggcgtctc    1020 tgtggcgacc tcgtacgagt tcgaggagca caacggcaag gagctgcgcg aggccgcgat   1080
caacggcctg ctggccggct cttgctcggc tgctgcggag cccgccgctg ccgcgccggc   1140
cgcccctagc gccgctgcca aggaggagcc ggaggagagc gacgaggacg acttcggcat   1200
gggcggtctc ttctaagcga ctcgccatct cttagcctcc ttgtggtgcg cttgaggtgc   1260
tctcgctctg cttctccttg cagtgttggc tgactctagc gggtatgtgt cgtcgcatta   1320
cacccacctc tcccacccct ttgctctacg cgctcgcatg cgcaatccgt gaatcatcga   1380
gggaagtctc tctgggtggc agtgggtaag cttgtgagga aagaggtgtg tgtgtgagcg   1440
ggcaggtacg tcggaccact taaacaaaca aacacacaca cacacggaaa gactcacgta   1500
cagcatccgt ccgcgcaac agcaacgtcc gccgcgcgaa gcagagcgcg tgcgctcatt    1560
gtaccgctgt gaacggagga ggggggact cttcgctttt ttcttttct tttttttgtt    1620 tcggtagttt attcttcatt ttccgtctca actcaaaaaa cagcacaaaa acgcggaaac   1680
gcagcatgag tggcgccgtt gcaatcgggg acggtggcgg cgcaacgcgt cgtggcaact   1740
gcgcatgggt tgctatctga tggatggttg cactgctgct cgaacacagg tggacctccc   1800
ccccccccgc aacgacgacg tccggtcgag tcgcgggcgt gtggccgtga gcacagggta   1860 gccttttcttt gcgtcgcaca gcacctatcg tcgtcgtcgg cactcctcat cacatctccc   1920
tcgtgtcgca cgaaggtgtg ctgtctgtga ggacgcttcc gtgtgagtag gtgcgtgcaa   1980
acatgcgtgc atcggcaccg gatcgcggtc gggtaggttc cacgctcctg gagggtcgca   2040
agtgtcttgc tgctccaggt gactgatgac caaggccata tcctcacgca acaccttcac   2100
tgctgccgcg ctgcttttcct ccagcacgaa gcgagcacag gggcacgggt gggggcggca   2160
agcgagtagc ctctgaggtt gtgcgtaggc gacacgtcgt gtgccagtgg gcactgcgca   2220 cctttttcagt gttgtgtgtg gaacacaggg tcggcgcacg ctgtcttcgg tgatgctttc   2280
tcattatgag ccgcttgccg agcgtgcgcg cgaccccgg cccctcctca cctcctcgcg    2340
cggagttaac gcgtgcacgc tgtgtcccct gtgtaaagac agcttccccc accccttgt    2400 caactccctc tcggtccgtc tttctcgcgt tcattctctc ttcttcgtga acgaaacacg   2460
accactcgcc tcgcatattc cgcgtgccca atatcccact cactccctta cacatgcatt   2520
gtccgtgcca caacccggcg cacacttcgg cacacgaaaa acaccttccc cgaccccacg   2580
acagatagcc aaggctattg caagtctcac aagatgccgt ctatcaccac tgccaagcgc   2640
gagtacgagg agcgcctcgt cgactgcctg accaagtaca gctgcgtgct gttcgtgggc   2700
atggacaacg tccgctcgca gcaggtgcac gatgtcggcc gtgcgctgcg cgcgaaggcc   2760
gagttcatga tgggcaagaa gacgctgcag ggcaagatcg tggagaagcg cgcgcaagcc   2820
aaggacgcga gccccgaggc gaagcacttc aacgatcagt gtgaggagta caacctgctg   2880
agcggcaaca ccggcctcat cttcacgaac aacgctgtcc aggagatcac gtctgtgctt   2940
```

```
gacgcgcacc gcgtgaagcg cgcggcgcgt gtcggagcga tttccccgtg tgacgtgatt    3000
gtcgctgctg gcagcaccgg catggagccg acccagacgt ccttcttcca ggcgctgaac    3060
attgcgacga agattgccaa gggtatggtg gagatcgtga cggagaagaa ggtgctgagc    3120
gtcggcgaca aggtggacaa ctcgacggcg acgctgctgc aaaagctgaa catcagcccg    3180
ttctactacc aggtgaatgt gctgtccgtg tgggaccgcg gtgtgctgtt cacccgcgag    3240
gacctgatga tgacggagga catggtggag aagatgctga tggaaggcct gagcaacgtt    3300
gcggcgatgg cgctgggtgc tggcatcccg acgtcttcga cgattggccc gatgctggtg    3360
gacgccttca agaacctgct ggctgtctct gtggcgacct cgtacgagtt cgaggagcac    3420
aacggcaagg agctgcgcga ggccgcgatc aacggcctgc tggccggctc ttgctcggct    3480
gctgcggagc ccgccgctgc cgcgccggcc gcccctagcg ccgctgccaa ggaggagccg    3540
gaggagagcg acgaggacga cttcggcatg gcggtctctt ctaagcgac tcgccatctc    3600 ccactgagca ccgtcgagtg ttcgtgtgtt cgcagggtgg acagcggcga gcgtgtgatg    3660
cccttggatc atcaggaagc aactctctcc ctttctctct gtgttcttcg tttcttcttt    3720
cattagtttt ggatcgccgt gcgctgcgca tcgctcagtt ctcatttata tcaataacaa    3780
caacgaagac                                                           3790
```

<210> SEQ ID NO 13
<211> LENGTH: 260
<212> TYPE: PRT
<213> ORGANISM: Leishmania major

<400> SEQUENCE: 13

```
Met Gly Lys Thr Val Leu Ser Cys Arg Lys Gly Asn Gly Ser Val Tyr
1               5                   10                  15

Gln Val His Gly His Lys Arg Leu Gly Pro Ala Lys Leu Arg Ile Leu
            20                  25                  30

Asp Tyr Ala Glu Arg His Gly Tyr Met Arg Gly Val Val Lys Ser Ile
        35                  40                  45

Glu His Glu Ala Gly Arg Gly Ala Ala Leu Ala Arg Val Glu Phe Arg
    50                  55                  60

His Pro Tyr Lys Phe Arg Arg Val Lys Glu Leu Met Val Ala Pro Glu
65                  70                  75                  80

Gly Met Phe Thr Gly Gln Ser Val Phe Cys Gly Gln Lys Ala Pro Leu
                85                  90                  95

Ala Ile Gly Asn Val Leu Pro Leu Gly Gln Ile Thr Glu Gly Cys Ile
            100                 105                 110

Val Cys Asn Val Glu Ala Lys Pro Gly Asp Arg Gly Thr Leu Ala Arg
        115                 120                 125

Ala Ser Gly Asp Tyr Cys Ile Ile Ile Ser His Asn His Glu Thr Gly
    130                 135                 140

Arg Thr Arg Leu Lys Leu Pro Ser Gly Gln Lys Lys Ser Val Pro Ser
145                 150                 155                 160

Thr Ser Arg Ala Met Ile Gly Ile Ile Ser Gly Gly Arg Ile Glu
                165                 170                 175

Lys Pro Val Leu Lys Ala Gly Asn Ser Phe Tyr Arg Phe Arg Gly Lys
            180                 185                 190

Arg Asn Cys Trp Pro Lys Val Arg Gly Val Ala Arg Asn Pro Val Glu
        195                 200                 205

His Pro His Gly Gly Gly Asn His Gln His Ile Gly His Pro Ser Thr
```

```
                210                 215                 220
Val Ser Arg His Ser Pro Pro Gly Gln Lys Val Gly Leu Ile Ala Ala
225                 230                 235                 240

Arg Arg Thr Gly Arg Ile Arg Gly Gly Lys Ala Val Lys Gly Ala Trp
                245                 250                 255

His Pro Glu Glu
        260

<210> SEQ ID NO 14
<211> LENGTH: 783
<212> TYPE: DNA
<213> ORGANISM: Leishmania major

<400> SEQUENCE: 14
atgggtaaga ctgtgctgag ctgccgtaag ggcaacggct ccgtgtacca ggtgcacggc      60
cacaagcgcc ttggccccgc caagctgcgc attctggact acgccgagcg ccacggctac     120
atgcgcggtg tggtgaagtc gatcgagcac gaggctggcc gcggtgcggc gctggcgcgc     180
gtggagttcc gccacccgta caagttccgc cgcgtgaagg agctgatggt ggcgccggag     240
ggcatgttca ccggccagtc ggtgttctgc ggccagaagg ccccgctcgc gatcggcaac     300
gtgctgcccc ttggccagat cacggagggc tgcattgtgt gcaacgtgga ggcgaagccc     360
ggtgaccgcg gcacgctggc gcgcgcgtcc ggcgactact gcatcatcat ctcgcacaac     420
cacgagacag gccgcacgcg cctgaagctg ccgagcgggc agaagaagtc cgtgccgagc     480
acgagccgcg cgatgatcgg catcatcagc ggcggtggcc gcatcgagaa gcccgtgctg     540
aaggccggta actcgttcta ccgcttccgc ggcaagcgca actgctggcc caaggtgcgt     600
ggtgttgccc gcaacccggt ggagcacccg cacggtggtg gtaaccatca gcacattggc     660
cacccgtcga cggtgtcgcg ccactcgccg ccgggccaga aggtgggtct gatcgctgcc     720
cgtcgcaccg gccgtattcg cggtggtaag gctgtcaagg gcgcgtggca cccggaggag     780
taa                                                                  783

<210> SEQ ID NO 15
<211> LENGTH: 252
<212> TYPE: PRT
<213> ORGANISM: Leishmania major

<400> SEQUENCE: 15

Met Ala Thr His Ser Val Tyr Gly Asn Ala Ser Asp Met Pro Ala Val
1               5                   10                  15

Pro Ala Pro Glu Ser Ala Ile Lys Arg Ala Ala Phe Lys Gln Gln
            20                  25                  30

Thr Glu Ser Phe Lys Lys Ala Val Val Ala Arg Lys Ala Ala Lys Ala
        35                  40                  45

Ala Leu Lys Lys Thr Ala Tyr Leu Arg Ala Arg Lys Tyr Ser Arg Glu
    50                  55                  60

Tyr Arg Gly Ala Glu Lys Lys Leu Val Thr Leu Arg Arg Gln Ala Ala
65                  70                  75                  80

Ser His Gly Asn Tyr Tyr Leu Glu Ala Lys Pro Lys Val Ala Val Val
                85                  90                  95

Thr Arg Ile Arg Gly Ile Ala Lys Val Asn Pro Lys Gln Arg Lys Ile
            100                 105                 110

Leu Gln Leu Leu Arg Leu Arg Gln Ile Phe Asn Thr Val Phe Val Lys
        115                 120                 125
```

```
Met Asn Lys Pro Met Glu Asn Met Leu Arg Ala Val Glu Pro Tyr Ile
    130                 135                 140
Ala Tyr Gly Tyr Pro Ser Leu Ala Thr Val Arg Ala Met Val Tyr Lys
145                 150                 155                 160
Arg Gly Tyr Leu Lys Ile Asn Gly Gln Arg Val Lys Ile Thr Asp Asn
                165                 170                 175
Gln Met Ile Lys Asp Lys Tyr Asn Asn Val Asp Ile Val Cys Ala Glu
            180                 185                 190
Asp Met Val Asn Gln Ile Tyr Thr Cys Gly Lys His Phe Arg Thr Val
        195                 200                 205
Thr His Gly Met Trp Pro Phe Lys Leu Ala Pro Pro Ala Gly Gly Met
    210                 215                 220
Arg Gln Lys Arg Arg His Phe Val Glu Gly Gly Asp Tyr Gly Asn Arg
225                 230                 235                 240
Asp Thr Leu Ile Asn Arg Phe Leu Ala Arg Met Ile
                245                 250

<210> SEQ ID NO 16
<211> LENGTH: 759
<212> TYPE: DNA
<213> ORGANISM: Leishmania major

<400> SEQUENCE: 16
atggccacac actcagttta cggcaacgca tccgacatgc ccgctgtccc tgcccctgag     60
tccgcgatca agcgtgctgc gttcaagcag cagcagacgg agagcttcaa gaaggccgtg    120
gtggccagaa aggctgccaa ggctgccctg aagaagaccg cctacctgcg tgcccgcaaa    180
tactcccgcg agtaccgcgg tgcggagaag aagctggtga cgctgcgccg ccaggccgcc    240
tctcacggta actactacct ggaggcgaag ccgaaggttg ccgtggtgac tcgcatccgc    300
ggtatcgcca aggtgaaccc gaagcagcgc aagattcttc agttgctgcg cctgcgccag    360
atcttcaaca cggtgtttgt gaagatgaac aagccgatgg agaacatgct gcgtgcggtg    420
gagccctaca tcgcgtacgg ctacccgtcc ctggccaccg tccgcgcgat ggtgtacaag    480
cgcggctacc tgaagatcaa cggccagcgc gtgaagatca ccgacaacca gatgatcaag    540
gataagtaca acaacgtgga cattgtgtgt gccgaggata tggtgaacca gatctacacc    600
tgcggcaagc acttccgcac ggtgacgcac ggcatgtggc ccttcaagct ggcccctccg    660
gccggtggca tgcgccagaa gcgccgtcac ttcgtggagg gtggcgacta tggtaaccgc    720
gacaccttga tcaaccgctt cctcgcccgc atgatctga                            759

<210> SEQ ID NO 17
<211> LENGTH: 264
<212> TYPE: PRT
<213> ORGANISM: Leishmania major

<400> SEQUENCE: 17

Met Pro Gly Lys Glu Val Lys Lys Val Thr Gln Pro Ala Lys Ala Ala
1               5                   10                  15
Ser Pro Tyr Lys Lys Pro Ala Val Ala Ser His Phe Ala Ala Arg Pro
            20                  25                  30
Lys Asn Phe Gly Ile Gly Gln Asp Val Pro Tyr Ala Arg Asp Leu Ser
        35                  40                  45
Arg Phe Met Arg Trp Pro Thr Phe Val Thr Met Gln Arg Lys Lys Arg
    50                  55                  60
Val Leu Gln Arg Arg Leu Lys Val Pro Pro Ala Leu Asn Gln Phe Thr
```

```
                65                  70                  75                  80
Lys Val Leu Asp Arg Ala Ser Arg Asn Glu Ala Leu Lys Leu Ile Lys
                    85                  90                  95
Lys Tyr Ala Pro Glu Thr Arg Lys Ala Arg Glu Arg Leu Gln Lys
                100                 105                 110
Val Ala Glu Glu Lys Lys Asp Pro Lys Lys Thr Val Ser Thr Lys
                115                 120                 125
Ala Pro Leu Ala Val Val Thr Gly Leu Gln Glu Val Thr Arg Ala Ile
130                 135                 140
Glu Lys Lys Gln Ala Arg Met Val Val Ile Ala Asn Asn Val Asp Pro
145                 150                 155                 160
Val Glu Leu Val Leu Trp Met Pro Asn Leu Cys Arg Ala Asn Lys Ile
                165                 170                 175
Pro Tyr Ala Ile Val Lys Asp Met Ala Arg Leu Gly Asp Ala Ile Gly
                180                 185                 190
Arg Lys Thr Ala Thr Cys Val Ala Leu Thr Asp Val Asn Ala Glu Asp
                195                 200                 205
Glu Ala Thr Leu Lys Asn Leu Ile Arg Ser Val Asn Ala Arg Phe Leu
210                 215                 220
Ser Arg Ser Asp Val Ile Arg Arg Gln Trp Gly Gly Leu Gln Leu Ser
225                 230                 235                 240
Leu Arg Ser Arg Ala Glu Leu Arg Lys Lys His Ala Arg Asn Ala Gly
                245                 250                 255
Val Asp Ala Ala Ala Ile Ile Gln
                260

<210> SEQ ID NO 18
<211> LENGTH: 795
<212> TYPE: DNA
<213> ORGANISM: Leishmania major

<400> SEQUENCE: 18
atgcccggca aggaagtgaa gaaggtgacg cagcccgcga aggccgcgtc tccgtacaag      60
aagcccgccg ttgcgtcgca tttcgcggcc cgcccgaaga acttcggtat tggccaggat    120
gtgccgtacg cgcgtgacct gtcccgcttc atgcggtggc cgacgttcgt gacgatgcag    180
cgcaagaagc gcgtgctgca gcgccgcctg aaggtgccgc cggcgctgaa ccagttcacg    240
aaggtgctgg accgcgcgag ccgaaacgag gcgctgaagc tgattaagaa gtacgcgccg    300
gagacccgca aggctcgccg cgagcgcctg cagaaggttg ccgaggagaa gaagaaggac    360
ccgaagaaga cggtatcgac gaaggctccc ctggctgttg tgaccggtct gcaggaggtg    420
acgcgcgcga tcgagaagaa gcaggctcgc atggttgtga tcgcgaacaa cgtggaccct    480
gtggagctcg tgctgtggat gccgaacctg tgccgcgcga acaagatccc gtatgccatc    540
gtgaaggaca tggcgcgcct gggcgatgcg atcgggcgga gacggcgac gtgcgttgcg    600 ctcaccgacg tgaacgccga ggatgaggcg acgctgaaga acctgatccg ctccgtgaac    660
gctcgcttct tgtcccgctc ggacgtgatc cgccgccagt ggggtggtct gcagctgtct    720
ctgcgatccc gcgcggagct gcgcaagaag catgcccgca acgctggtgt ggacgccgcg    780
gccatcatcc agtaa                                                     795

<210> SEQ ID NO 19
<211> LENGTH: 222
<212> TYPE: PRT
<213> ORGANISM: Leishmania major
```

<400> SEQUENCE: 19

```
Met Ala Phe Pro Ser Arg Lys Asp Ala Phe Arg Ala Gln Arg Lys Gly
1               5                   10                  15

Ala Lys Lys His Arg Pro Glu Ile Ile Val Ile Asp Leu Lys Asp His
            20                  25                  30

Val Leu Gly Arg Ala Ala Val Val Ala Lys Gln Leu Leu Leu Gly
        35                  40                  45

Lys Lys Ile Thr Val Val Arg Cys Glu Gln Leu Asn Ile Ala Gly Thr
50                  55                  60

Glu Ile Arg Asn Lys Ile Lys Tyr Leu Gln Tyr Leu Arg Lys Arg Lys
65                  70                  75                  80

Leu Thr Asn Pro Thr Lys Gly Pro Phe His His Arg Ala Pro Ser Asp
                85                  90                  95

Val Phe Val Arg Thr Val Arg Ser Met Leu Pro Arg Tyr Thr Lys Arg
            100                 105                 110

Gly Met Lys Ala Leu Asn Ser Leu Val Ala Tyr Glu Gly Ile Pro Pro
        115                 120                 125

Asn Val Val Arg Thr Gly Gly Arg Val Val Ile Pro Arg Ala Gln Arg
130                 135                 140

His Val Cys Tyr Arg Ser Glu Arg Pro Tyr Thr Val Leu Gly Asn Met
145                 150                 155                 160

Cys Lys His Val Gly Trp Lys Tyr Ser Asp Val Val Ala Asn Leu Glu
                165                 170                 175

Lys Ala Arg Val Glu Lys Ala Ser Arg His His Glu Lys Gln Ala Lys
            180                 185                 190

Leu Arg Asp Ala Trp Lys Ser Ala Arg Lys Glu Ala Leu Ala Lys Met
        195                 200                 205

Pro Lys His Asn Val Glu Val Leu Lys Lys Phe Gly Tyr Ala
210                 215                 220
```

<210> SEQ ID NO 20
<211> LENGTH: 669
<212> TYPE: DNA
<213> ORGANISM: Leishmania major

<400> SEQUENCE: 20

```
atggccttc ctagccgcaa ggatgcgttc cgcgcgcagc gcaagggcgc caagaagcac    60
cgccccgaga tcatcgtgat cgacctgaag gatcacgtgc ttggtcgcgc ggcggctgtg   120
gttgccaagc agctgctcct gggtaagaag atcaccgtgg tgcgctgcga gcagctcaac   180
attgccggta cggagatccg caacaagatc aagtacctgc agtacctgcg caagcggaag   240
ctgacgaacc ccacaaaggg tcccttccac caccgtgccc cgtccgacgt gtttgtccgc   300
actgtgcgca gcatgctgcc ccggtacacg aagcgcggca tgaaggcgct taactcgctg   360
gtggcctacg agggaattcc gcccaacgtg gtgcgcacgg gcgggcgcgt ggtgatcccg   420
cgcgcccagc gccatgtgtg ctaccgctcg gagcgtcctt acacagtgct cggcaacatg   480
tgcaagcacg tgggctggaa gtacagcgac gtcgtcgcca atctcgagaa ggctcgcgtg   540
gagaaggcgt cccgccacca cgaaaagcag gcgaagcttc gcgacgcgtg gaagtcggcc   600
cgcaaggagg cgctcgccaa gatgcccaag cacaacgtgg aggtgctgaa gaagtttggc   660
tacgcgtag                                                           669
```

<210> SEQ ID NO 21

<211> LENGTH: 273
<212> TYPE: PRT
<213> ORGANISM: Leishmania major

<400> SEQUENCE: 21

```
Met Ala Lys Lys His Leu Lys Arg Leu Tyr Ala Pro Lys Asp Trp Met
1               5                   10                  15

Leu Ser Lys Leu Thr Gly Val Phe Ala Pro Arg Pro Arg Pro Gly Pro
            20                  25                  30

His Lys Leu Arg Glu Cys Leu Pro Leu Leu Val Ile Ile Arg Asn Arg
        35                  40                  45

Leu Lys Tyr Ala Leu Asn Ala Arg Glu Gly Glu Met Ile Leu Arg Gln
    50                  55                  60

Gly Leu Val His Val Asp Asn His Pro Arg Arg Asp Gly Lys Tyr Pro
65                  70                  75                  80

Ala Gly Phe Met Asp Val Val Glu Ile Pro Lys Thr Gly Asp Arg Phe
                85                  90                  95

Arg Leu Met Tyr Asp Val Lys Gly Arg Phe Ala Leu Val Asn Leu Ser
            100                 105                 110

Glu Ala Glu Ala Gln Ile Lys Leu Met Lys Val Val Asn Leu Tyr Thr
        115                 120                 125

Ala Thr Gly Arg Val Pro Val Ala Val Thr His Asp Gly His Arg Ile
    130                 135                 140

Arg Tyr Pro Asp Pro His Thr Ser Ile Gly Asp Thr Ile Val Tyr Asn
145                 150                 155                 160

Val Lys Glu Lys Lys Cys Val Asp Leu Ile Lys Asn Arg Gln Gly Lys
                165                 170                 175

Ala Val Ile Val Thr Gly Gly Ala Asn Arg Gly Arg Ile Gly Glu Ile
            180                 185                 190

Val Lys Val Glu Cys His Pro Gly Ala Phe Asn Ile Ala His Leu Lys
        195                 200                 205

Asp Ala Ser Gly Ala Glu Phe Ala Thr Arg Ala Ala Asn Ile Phe Val
    210                 215                 220

Ile Gly Lys Asp Leu Asn Asn Leu Gln Val Thr Val Pro Lys Gln Gln
225                 230                 235                 240

Gly Leu Arg Met Asn Val Ile Gln Glu Arg Glu Arg Leu Ile Ala
                245                 250                 255

Ala Glu Ala Arg Lys Asn Ala Pro Ala Arg Gly Ala Arg Ala Arg
            260                 265                 270

Lys
```

<210> SEQ ID NO 22
<211> LENGTH: 822
<212> TYPE: DNA
<213> ORGANISM: Leishmania major

<400> SEQUENCE: 22

```
atggccaaga agcacctcaa gcgcttgtat gcgcccaagg actggatgct gagcaagctg      60
accggcgtgt tcgcgccgcg tccgcgtccg ggtccgcaca agctgcgcga gtgcctgccg     120
ctgctggtga tcatccgcaa ccggctgaag tacgcgctga acgcgcgcga gggtgagatg     180
atcctgcgcc agggtctggt gcacgtggac aaccaccgc gccgcgacgg caagtatccc      240
gccggtttca tggacgtggt cgagatcccc aagacgggcg accgcttccg cctgatgtac     300
gacgtcaagg gccgcttcgc gttggtgaac ctgtccgagg cggaggcgca gatcaagctg     360
```

```
atgaaggttg tgaacctgta cacggccacc ggccgcgtgc cggtcgctgt gacgcacgac    420
ggccaccgca tccgctaccc ggacccgcac acctccattg gtgacaccat cgtgtacaac    480
gtcaaggaga agaagtgcgt ggacctgatc aagaaccgcc agggcaaggc cgtgatcgtg    540
accggtggcg ccaaccgcgg ccgcatcggc gagatcgtga aggtggagtg ccaccccggt    600
gcgttcaaca ttgcgcacct gaaggacgcg tccggcgccg agttcgccac ccgcgccgcg    660
aacatcttcg tgatcggcaa ggacctgaac aacctgcagg taacggtgcc gaagcagcag    720
ggcctgcgca tgaacgtgat ccaggagcgc gaggagcgcc tgatcgcggc ggaggcccgc    780
aagaacgcgc cggctcgtgg tgcccgcagg gcccgcaagt ga                      822
```

```
<210> SEQ ID NO 23
<211> LENGTH: 249
<212> TYPE: PRT
<213> ORGANISM: Leishmania major

<400> SEQUENCE: 23
```

```
Met Lys Leu Asn Ile Ala Tyr Pro Arg Asn Gly Thr Val Lys Gln Phe
  1               5                  10                  15

Glu Ile Ser Asp Glu Val Leu Arg Arg Val Gln Leu Gln Asp Tyr Arg
             20                  25                  30

Leu Gly Asn Glu Val Asp Gly Ala Ile Phe Gly Ser Glu Phe Lys Gly
         35                  40                  45

Tyr Ile Phe Arg Leu Arg Gly Ser Asp Lys Asp Gly Phe Pro Met
     50                  55                  60

Val Pro Gly Val Leu Ala Ser Ser Arg Val Ser Leu Leu Val Lys Arg
 65                  70                  75                  80

Gly Ala Ile Gly Phe Asn Thr Phe Arg Gly Tyr Gln Gly Glu Arg Arg
                 85                  90                  95

Arg Lys Asn Val Arg Gly Cys Val Leu Ala Ser Asp Ile Ala Leu Val
            100                 105                 110

Asn Val Thr Ile Ser Lys Val Gly Asp Gln Pro Ile Glu Gly Val Thr
        115                 120                 125

Asp Thr Thr Ala Pro Arg Arg Leu Gly Pro Lys Arg Ala Ser Lys Ile
    130                 135                 140

Arg Lys Leu Phe Asn Leu Ser Arg Thr Glu Asp Val Arg Lys Tyr Val
145                 150                 155                 160

Val Arg Arg Arg Val Val Lys Ser Gly Lys Lys Asp Arg Leu Lys Ala
                165                 170                 175

Pro Lys Ile Gln Arg Leu Ile Thr Pro Arg Val Lys Ala Arg Arg Ala
            180                 185                 190

Lys Lys Ala Lys Asp Ala Ile Ala Lys Val Arg Ala Ser Ala Ala Glu
        195                 200                 205

Arg Arg Glu Tyr Leu Arg Leu Ile Ala Ser Asn Arg Arg Ala Leu Arg
    210                 215                 220

Gln Arg Asp His Ser Lys Lys His Thr Arg Lys Val His Ala Gln Arg
225                 230                 235                 240

Ala Glu Val Ala Ala Phe Gln Lys Lys
                245
```

```
<210> SEQ ID NO 24
<211> LENGTH: 750
<212> TYPE: DNA
<213> ORGANISM: Leishmania major

<400> SEQUENCE: 24
```

-continued

```
atgaagctca acatcgcgta cccccgcaac gggacggtga agcagttcga gatctcggac    60
gaggtgctcc gccgcgtgca gctgcaggac taccgcctcg gcaacgaggt ggacggcgcc   120
atctttggta gcgagttcaa gggctacatc ttccgcctgc gcggtggctc ggacaaggat   180
ggtttcccga tggtccctgg cgtgcttgcc tccagccgtg tgtcgctgct ggtgaagcgc   240
ggtgcgatcg gcttcaacac cttccgcggc taccagggtg agcgccgccg caagaacgtt   300
cgcggctgcg tgctcgcgag cgacattgcg ctggtgaacg tgaccatctc caaggtcggt   360
gaccagccga tcgagggtgt gacggacacc acggctcccc gccgtctggg tccgaagcgc   420
gcgagcaaga tccgcaagct cttcaacctg tcccgcaccg aagacgtgcg gaagtacgtt   480
gttcgccgcc gcgtcgtgaa gagcggcaag aaggaccggc tgaaggcccc gaagatccag   540
cgtctgatca cgccgaggt caaggcccgc cgtgccaaga aggccaagga cgccatcgcc    600
aaggtgcgcg cgtctgccgc tgagcgccgt gagtacctgc gccttatcgc ctcgaaccgc   660
cgtgcgctgc cccagcgtga ccactccaag aagcacaccc ggaaggtgca cgcccagcgc   720
gctgaggtgg cagcattcca gaagaagtaa                                   750
```

<210> SEQ ID NO 25
<211> LENGTH: 419
<212> TYPE: PRT
<213> ORGANISM: Leishmania major

<400> SEQUENCE: 25

```
Met Ser His Cys Lys Phe Glu His Pro Arg His Gly His Leu Gly Phe
  1               5                  10                  15

Leu Pro Arg Lys Arg Ser Arg Gln Ile Arg Gly Arg Ala Arg Ala Phe
                 20                  25                  30

Pro Lys Asp Asp Ala Thr Gln Lys Pro His Leu Thr Ser Phe Met Val
             35                  40                  45

Phe Lys Ala Gly Met Thr His Ile Val Arg Asp Val Asp Arg Pro Gly
         50                  55                  60

Ser Lys Val Asn Lys Lys Glu Val Val Glu Pro Val Thr Ile Leu Glu
 65                  70                  75                  80

Ala Pro Pro Met Val Ile Val Gly Ile Val Gly Tyr Arg Gln Thr Pro
                 85                  90                  95

Val Gly Leu Lys Thr Ile Gly Thr Val Trp Ala His Thr Ser Val
                100                 105                 110

Glu Phe Arg Arg Arg Tyr Tyr Lys Asn Trp Lys Gln Ser Ala Gln Leu
                115                 120                 125

Ala Phe Ser Arg Gln Lys Gln Phe Ala Asn Thr Lys Glu Gly Lys Val
            130                 135                 140

Ala Glu Ala Arg Thr Leu Asn Ala Phe Ala Lys Ala Ser Val Ile
145                 150                 155                 160

Arg Val Ile Ala His Thr Gln Leu Arg Lys Leu Arg Asn His Arg Val
                165                 170                 175

Gly Val Lys Lys Ala His Val Gln Glu Ile Gln Val Asn Gly Gly Ser
                180                 185                 190

Val Ala Ala Lys Ile Ala Leu Ala Lys Ser Leu Leu Glu Lys Glu Val
            195                 200                 205

Arg Val Asp Ser Val Phe Gln Gln Ser Glu Ala Cys Asp Val Cys Ser
        210                 215                 220

Val Thr Lys Gly His Gly Thr Glu Gly Val Val Lys Arg Trp Gly Val
225                 230                 235                 240
```

```
Ala Cys Leu Pro Arg Lys Thr His Arg Gly Leu Arg Lys Val Ala Cys
            245                 250                 255

Ile Gly Ala Trp His Pro Ala Arg Val Met Tyr Thr Val Ala Arg Ala
        260                 265                 270

Gly Gln His Gly Tyr His His Arg Thr Gln Leu Asn Lys Lys Ile Tyr
    275                 280                 285

Gln Ile Gly Arg Ser Val Ala Val Glu Pro Asn Gln Ala Thr Thr Thr
290                 295                 300

Tyr Asp Leu Thr Ala Lys Thr Ile Thr Pro Met Gly Gly Phe Val Gly
305                 310                 315                 320

Tyr Gly Thr Val Arg Asn Asp Tyr Val Met Leu Lys Gly Ser Val Ser
            325                 330                 335

Gly Pro Arg Arg Arg Val Met Thr Leu Arg Arg Pro Met Ala Pro Gln
        340                 345                 350

Thr Ser Arg Gln Leu Lys Glu Lys Ile Val Leu Lys Phe Ile Asp Thr
    355                 360                 365

Ser Ser Lys Ile Gly His Gly Arg Phe Gln Thr Lys Lys Glu Lys Asn
370                 375                 380

Gln Trp Phe Gly Pro Leu Lys Lys Asp Arg Ile Arg Arg Glu Glu Arg
385                 390                 395                 400

Leu Arg Lys Glu Arg Ala Ala Arg Ala Val Glu Arg Lys Ala Lys Ala
            405                 410                 415

Ala Lys Lys

<210> SEQ ID NO 26
<211> LENGTH: 1260
<212> TYPE: DNA
<213> ORGANISM: Leishmania major

<400> SEQUENCE: 26
atgtctcact gcaagttcga gcaccccgc cacggccatc tcggcttcct gccgcgcaag      60
cgctcgcgcc agatccgcgg ccgtgcgcgc gcgttcccca aggacgacgc gacgcagaag     120
ccccacctga cgagcttcat ggtgttcaag gccggtatga cgcacattgt gcgtgatgtc     180
gatcgccctg gatcgaaggt gaacaagaag gaagtggtgg agccggtgac gatcctggag     240
gcgccgccga tggtgattgt cggcattgtg ggctaccgcc aaacgccggt ggcctgaag     300
acgatcggca ccgtgtgggc gcaccacacg agcgtcgagt ccgccgccg ctactacaag     360
aactggaagc agtctgcgca actggccttc tcccgccaga agcagtttgc gaacacgaag     420
gagggcaagg tcgccgaggc gcgcacgctg aacgcgttcg cgaagaaggc gtccgtcatc     480
cgcgtgatcg cgcacacgca gctgcgcaag cttcgcaacc accgcgtggg cgtgaagaag     540
gcgcacgtgc aggagatcca ggtcaacggc ggcagcgttg cggcgaagat cgcgctggcc     600
aagtccctgc tggagaagga ggtgcgcgtc gactccgtgt ccagcagtc cgaggcgtgc     660
gacgtgtgct ccgtcacgaa aggccacggt acggagggcg tggtgaagcg ctggggcgtt     720
gcctgcctgc cacgcaagac gcaccgcggt ctgcgcaagg ttgcgtgcat cggcgcgtgg     780
caccctgccc gcgtcatgta cactgtcgcg cgcgccggtc agcacggtta ccaccaccgc     840
acgcagctga caagaagat ctaccagatc ggccgctccg ttgctgtgga gccgaaccag     900
gcgacgacga cctacgatct gacagccaag acgatcacgc ccatgggtgg cttcgtcggc     960
tacggtacgg tgcgcaacga ctacgtgatg ctgaagggct ccgtgtctgg cccgcgccgc    1020
cgtgtgatga cgctgcgccg cccgatggcg ccgcagacgt cgcgccagct gaaggagaag    1080
```

```
atcgtgctga agttcatcga cacgagctcg aagatcggcc acggccgctt ccagacgaag    1140
aaggagaaga accagtggtt cggcccgctc aagaaggacc gcatccgccg cgaggagcgc    1200
ctgcgcaagg agcgcgctgc ccgcgccgtg gagcgcaagg caaaggccgc gaagaagtaa    1260
```

<210> SEQ ID NO 27
<211> LENGTH: 328
<212> TYPE: PRT
<213> ORGANISM: Leishmania major

<400> SEQUENCE: 27

```
Met Cys Thr Leu Ala Asn Trp Val Arg Ala Ile Ile Lys Lys His Ser
1               5                   10                  15

Thr Leu Ala His Thr Leu Glu Met Pro Phe Val Lys Val Lys Asn
            20                  25                  30

Lys Ala Tyr Phe Lys Arg Phe Gln Val Lys Tyr Arg Arg Arg Glu
        35                  40                  45

Gly Lys Thr Asp Tyr His Ala Arg Arg Gln Met Val Leu Gln Asp Lys
    50                  55                  60

Thr Lys Phe Gly Ser Pro Lys Tyr Arg Leu Val Val Arg Ile Thr Asn
65                  70                  75                  80

Lys Asp Ile Ile Ala Gln Ile Val Gln Ala Lys Ile Val Gly Asp Glu
                85                  90                  95

Val Val Met Ala Ala Tyr Ala His Glu Leu Pro Ala Phe Gly Ile Glu
            100                 105                 110

His Gly Leu Thr Asn Tyr Ala Ala Ala Tyr Thr Gly Leu Leu Leu
        115                 120                 125

Ala Arg Arg Thr Leu Ala Lys Leu Gly Ile Ala Asp Lys Phe Gln Gly
130                 135                 140

Ala Lys Glu Ala Asp Gly Ser Tyr Ser Ala Val Arg Thr Lys Lys Asp
145                 150                 155                 160

Asp Glu Gly Asp Glu Glu Arg Phe Pro Phe Lys Ala Ile Leu Asp
                165                 170                 175

Val Gly Leu Ala Arg Thr Thr Thr Gly Ala Arg Val Phe Gly Val Leu
            180                 185                 190

Lys Gly Ala Val Asp Gly Gly Met Ala Val Pro His Arg Pro Asn Arg
        195                 200                 205

Phe Pro Gly Tyr Asn Lys Glu Lys Ser Ser Leu Asp Ala Lys Val His
    210                 215                 220

Arg Asp Arg Ile Phe Gly Lys His Val Ala Asp Tyr Leu Lys Gln Val
225                 230                 235                 240

Lys Glu Glu Ala Ser Ser Asn Pro Asp Glu Lys Cys Val Gln Phe Ser
                245                 250                 255

Lys Tyr Met Ala Ala Lys Val Leu Pro Glu Ser Ile Glu Gly Met Tyr
            260                 265                 270

Lys Lys Ala His Ala Ala Ile Arg Ala Asp Pro Ser Lys Ser Leu Pro
        275                 280                 285

Lys Lys Ala Lys Lys Glu Gly Val Ala His Lys Ser Tyr Lys Thr Lys
    290                 295                 300

Lys Leu Ser Gly Ala Glu Lys Arg Ala Ala Lys Ala Lys Val Ala
305                 310                 315                 320

Ala Ile Arg Glu Arg Leu Gly Lys
                325
```

```
<210> SEQ ID NO 28
<211> LENGTH: 987
<212> TYPE: DNA
<213> ORGANISM: Leishmania major

<400> SEQUENCE: 28
atgtgcacgc tggcaaattg ggtacgcgct atcatcaaga aacactcaac actcgcccac      60
acactcgaga tgccgttcgt caaggtcgtg aagaacaagg cgtacttcaa gcgcttccag     120
gtgaagtacc gccgtcgccg cgagggcaag acggactacc acgcgcgccg gcagatggtg     180
ctgcaggaca agacgaagtt cggctcgccc aagtaccgcc ttgttgtgcg catcacgaac     240
aaggacatca ttgcgcagat cgtgcaggcg aagatcgtcg cgacgaggt ggtgatggcc      300 gcgtacgcgc acgagctgcc tgcgttcggc attgagcacg gcctgacaaa ctacgctgct     360
gcgtacgcga ctggtctgct gctggcgcgc cgcacgctgg cgaagctggg catcgcggac     420
aagttccagg gcgcgaagga ggcggacggc tcgtactctg ctgtgcgcac gaagaaggac     480
gacgagggcg acgacgagga gcgctttccg ttcaaggcga tcctggacgt cggccttgcg     540
cgcacgacga ccggcgcccg cgtgttcggc gtgctgaagg gcgcggtgga cggcggtatg     600
gctgtgccgc accgccccaa ccgcttcccc ggctacaaca aggagaagag ctcgctggac     660
gcgaaggtgc accgcgaccg catctttggc aagcacgtgg cggactacct gaagcaggtg     720
aaggaggagg cgagctcgaa ccctgacgag aagtgcgtgc agttctcgaa gtacatggcc     780
gcgaaggttt tgccggagag catcgagggc atgtacaaga aggcgcacgc ggcgatccgc     840
gcggacccgt cgaagtcgct gccgaagaag gcgaagaagg agggcgtcgc gcacaagagc     900
tacaagacga agaagctgag cggcgcggag aagagggccg ccgcgaaggc gaaggtcgcg     960
gccatccgcg agcgcctcgg caagtaa                                         987

<210> SEQ ID NO 29
<211> LENGTH: 10
<212> TYPE: DNA
<213> ORGANISM: Artificial
<220> FEATURE:
<223> OTHER INFORMATION: Immunostimulatory oligonucleotide Th-1
      promoting adjuvant

<400> SEQUENCE: 29
tcaacgttga                                                             10

<210> SEQ ID NO 30
<211> LENGTH: 14
<212> TYPE: DNA
<213> ORGANISM: Artificial
<220> FEATURE:
<223> OTHER INFORMATION: Immunostimulatory oligonucleotide Th-1
      promoting adjuvant

<400> SEQUENCE: 30
gctagcgtta gcgt                                                        14

<210> SEQ ID NO 31
<211> LENGTH: 33
<212> TYPE: DNA
<213> ORGANISM: Artificial
<220> FEATURE:
<223> OTHER INFORMATION: primer

<400> SEQUENCE: 31
cgggatcctt taatggccac cacgtacgag gag                                   33
```

<210> SEQ ID NO 32
<211> LENGTH: 32
<212> TYPE: DNA
<213> ORGANISM: Artificial
<220> FEATURE:
<223> OTHER INFORMATION: primer

<400> SEQUENCE: 32
cgggatcccc ccttggatgg gtactgcgca gc                                32

<210> SEQ ID NO 33
<211> LENGTH: 1283
<212> TYPE: DNA
<213> ORGANISM: Artificial
<220> FEATURE:
<223> OTHER INFORMATION: pKmp11AAP - PCR product coding for the Kmp11
      protein, digested with BamHI and inserted in the BamHI digested
      vector pAAP.

<400> SEQUENCE: 33
atgagaggat ctcatcacca tcaccatcac acggatcctt taatggccac cacgtacgag      60
gagttttcgg cgaagctgga ccgcctgggt gaggagttca acaggaagat gcaggagcag     120
aacgccaagt tctttgcgga caagccggat gagtcgacgc tgtcgcccga gatgaaggag     180
cactacgaga agttcgagcg catgatcaag gagcacacag agaagttcaa caagaagatg     240
cacgagcact cggagcactt caagcagaag ttcgccgagc tgctggagca gcagaaggct     300
gcgcagtacc catccaaggg gggatcctct agacccatgt ccaccaagta cctcgccgcg     360
tacgctctgg cctccctgag caaggcgtcc ccgtctcagg cggacgtgga ggctatctgc     420
aaggccgtcc acatcgacgt cgaccaggcc accctcgcct tgtgatgga gagcgttacg      480 ggacgcgacg tggccaccct gatcgcgag gcgccgcga agatgagcgc gatgccggcg       540
gccagctctg gtgccgctgc tggcgtcact gcttccgctg cgggtgatgc ggctccggct     600
gccgccgccg cgaagaagga cgagcccgag gaggaggccg acgacgacat gggcccctct     660
agagtcgacc ccatgcagta cctcgccgcg tacgccctcg tggcgctgtc tggcaagacg     720
ccgtcgaagg cggacgttca ggctgtcctg aaggccgccg gcgttgccgt ggatgcctcc     780
cgcgtggatg ccgtcttcca ggaggtggag ggcaagagct tcgatgcgct ggtggccgag     840
ggccgcacga gctggtggg ctctggctct gccgctcctg ctggcgctgt ctccactgct       900
ggtgccggcg ctggcgcggt ggccgaggcg aagaaggagg agcccgagga ggaggaggcc     960
gatgatgaca tgggcccccgt cgacctgcag cccgccgctg ccgcgccggc cgccccctagc  1020 gccgctgcca aggaggagcc ggaggagagc gacgaggacg acttcggcat gggcggtctc    1080
ttctaagcga ctcgccatct cttagcctcc ttgtggtgcg cttgaggtgc tctcgctctg    1140
cttctccttg cagtgttggc tgactctggc gggtatgtgc cgtcgcatta cacccacctc    1200 tcccaccccct tgccctacg cgctcgcatg cgcaatccgt gaatcatcga gggaagtctc    1260
tctgggtggc agtgggtaag ctt                                           1283

<210> SEQ ID NO 34
<211> LENGTH: 361
<212> TYPE: PRT
<213> ORGANISM: Artificial
<220> FEATURE:
<223> OTHER INFORMATION: KAAP - Protein encoded by pKmp11AAP consisting
      of AAP fused to Kmp11

<400> SEQUENCE: 34

```
Met Arg Gly Ser His His His His His His Thr Asp Pro Leu Met Ala
1               5                   10                  15

Thr Thr Tyr Glu Glu Phe Ser Ala Lys Leu Asp Arg Leu Gly Glu Glu
            20                  25                  30

Phe Asn Arg Lys Met Gln Glu Gln Asn Ala Lys Phe Phe Ala Asp Lys
        35                  40                  45

Pro Asp Glu Ser Thr Leu Ser Pro Glu Met Lys Glu His Tyr Glu Lys
    50                  55                  60

Phe Glu Arg Met Ile Lys Glu His Thr Glu Lys Phe Asn Lys Lys Met
65                  70                  75                  80

His Glu His Ser Glu His Phe Lys Gln Lys Phe Ala Glu Leu Leu Glu
                85                  90                  95

Gln Gln Lys Ala Ala Gln Tyr Pro Ser Lys Gly Gly Ser Ser Arg Pro
            100                 105                 110

Met Ser Thr Lys Tyr Leu Ala Ala Tyr Ala Leu Ala Ser Leu Ser Lys
            115                 120                 125

Ala Ser Pro Ser Gln Ala Asp Val Glu Ala Ile Cys Lys Ala Val His
            130                 135                 140

Ile Asp Val Asp Gln Ala Thr Leu Ala Phe Val Met Glu Ser Val Thr
145                 150                 155                 160

Gly Arg Asp Val Ala Thr Leu Ile Ala Glu Gly Ala Ala Lys Met Ser
                165                 170                 175

Ala Met Pro Ala Ala Ser Ser Gly Ala Ala Gly Val Thr Ala Ser
            180                 185                 190

Ala Ala Gly Asp Ala Ala Pro Ala Ala Ala Ala Lys Lys Asp Glu
            195                 200                 205

Pro Glu Glu Glu Ala Asp Asp Met Gly Pro Ser Arg Val Asp Pro
    210                 215                 220

Met Gln Tyr Leu Ala Ala Tyr Ala Leu Val Ala Leu Ser Gly Lys Thr
225                 230                 235                 240

Pro Ser Lys Ala Asp Val Gln Ala Val Leu Lys Ala Ala Gly Val Ala
            245                 250                 255

Val Asp Ala Ser Arg Val Asp Ala Val Phe Gln Glu Val Glu Gly Lys
            260                 265                 270

Ser Phe Asp Ala Leu Val Ala Glu Gly Arg Thr Lys Leu Val Gly Ser
    275                 280                 285

Gly Ser Ala Ala Pro Ala Gly Ala Val Ser Thr Ala Gly Ala Gly Ala
    290                 295                 300

Gly Ala Val Ala Glu Ala Lys Lys Glu Glu Pro Glu Glu Glu Glu Ala
305                 310                 315                 320

Asp Asp Asp Met Gly Pro Val Asp Leu Gln Pro Ala Ala Ala Ala Pro
            325                 330                 335

Ala Ala Pro Ser Ala Ala Ala Lys Glu Glu Pro Glu Glu Ser Asp Glu
            340                 345                 350

Asp Asp Phe Gly Met Gly Gly Leu Phe
            355                 360

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
```

```
cccaagctta tggccaccac ctacgaggag                                        30
```

<210> SEQ ID NO 36
<211> LENGTH: 22
<212> TYPE: DNA
<213> ORGANISM: Artificial
<220> FEATURE:
<223> OTHER INFORMATION: primer

<400> SEQUENCE: 36

```
cattactgga tctatcaaca gg                                                22
```

<210> SEQ ID NO 37
<211> LENGTH: 297
<212> TYPE: PRT
<213> ORGANISM: homo sapiens

<400> SEQUENCE: 37

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

<210> SEQ ID NO 38
<211> LENGTH: 498
<212> TYPE: DNA
<213> ORGANISM: Cupressus arizonica

<400> SEQUENCE: 38

```
atggacgaag ttccgtcaag cgacgaatct aagtcggcaa gctctgggaa acgggttttg        60
gaacagagcg ttcacgaatt ggaagaggtt ttcaagaaat ttgatgcgaa cggggatgga       120
aagatctcag gatcagagct tgcagacatc ttgcggtcta tgggaagtga agtagacgag       180
gcagaggtca aggccatgat ggaggaggca gacacggatg gtgacggtta tgttagcctg       240
caagagtttg tggatctgaa tattaaaggc gctactgtga aggatttgaa gaatgctttc       300
aaagtgtttg atcgggactg taatggcacc atttcgcctg ctgagctgtg cgagactctc       360
aaaagcgtgg gcgagccctg caccatcgag gagtctaaga acattattca caacgtcgac       420
aagaatgggg atggacttat taatgttgaa gaatttcaga caatgatgac aagtgaaatg       480
actgataaga gcaaatga                                                     498
```

<210> SEQ ID NO 39
<211> LENGTH: 1044
<212> TYPE: DNA
<213> ORGANISM: Cupressus arizonica

<400> SEQUENCE: 39

```
tctgataatc ccatagacag ctgctggaga ggagattcga attgggatca aaacagaatg        60
aagctcgcag actgtgttgt gggatttgga agctcgacca tgggaggcaa aggaggagaa       120
atttacaccg tcacaagctc agaagataat cctgtgaatc ctacaccagg aactttgcgc       180
tatgcagcaa caagagaaaa agcactttgg ataattttct ctcagaatat gaatataaag       240
ctccagatgc ctttgtatgt taatggatat aagactattg acggcagggg agcagatgtt       300
catcttggca atggcggtcc ctgtctgttt atgaggaaag cgagccatgt tattctccat       360
ggtttgcata tacacggttg taatacgagt gttttggggg atgttttggt aagtgagtcc       420
attggtgtgg agcctgttca tgctcaggat ggggacgcca ttactatgcg gaatgttaca       480
aatgcttgga ttgatcataa ttctctctcc gattgttctg atggtcttat cgatgttaca       540
cttggttcca ctggaattac tatctccaac aatcacttct tcaaccatca taaagtgatg       600
ttgttaggac atgatgatac atatgatgat gacaaatcta tgaaagtgac agtggcgttc       660
aatcaatttg gacccaatgc tgggcaacga atgccaaggg cacgatatgg acttgtacat       720
gttgcaaaca taattatga tcaatggaat atatatgcta ttggtgggag ttcaaatcca       780
accattctaa gtgaagggaa tagtttcact gcccccaaatg agagctacaa gaaggaagta       840
acaaagcgta tagggtgtga acaacatcca gcttgtgcga actgggtgtg agatccaca        900
cgagatgctt ttactaatgg agcttatttt gtatcatcgg ggaaagctga agacaccaat       960
atatacaata gtaatgaagc tttcaaagtt gagaatggga atgcagctcc tcaattaaca      1020
caaatgctg gagttgtagc ataa                                              1044
```

<210> SEQ ID NO 40
<211> LENGTH: 165
<212> TYPE: PRT
<213> ORGANISM: Cupressus arizonica

<400> SEQUENCE: 40

Met Asp Glu Val Pro Ser Ser Asp Glu Ser Lys Ser Ala Ser Ser Gly

```
             1               5                  10                 15
          Lys Arg Val Leu Glu Gln Ser Val His Glu Leu Glu Val Phe Lys
                          20                 25                 30
          Lys Phe Asp Ala Asn Gly Asp Gly Lys Ile Ser Gly Ser Glu Leu Ala
                          35                 40                 45
          Asp Ile Leu Arg Ser Met Gly Ser Glu Val Asp Glu Ala Glu Val Lys
                          50                 55                 60
          Ala Met Met Glu Glu Ala Asp Thr Asp Gly Asp Gly Tyr Val Ser Leu
          65                      70                 75                 80
          Gln Glu Phe Val Asp Leu Asn Ile Lys Gly Ala Thr Val Lys Asp Leu
                               85                 90                 95
          Lys Asn Ala Phe Lys Val Phe Asp Arg Asp Cys Asn Gly Thr Ile Ser
                              100                105                110
          Pro Ala Glu Leu Cys Glu Thr Leu Lys Ser Val Gly Glu Pro Cys Thr
                              115                120                125
          Ile Glu Glu Ser Lys Asn Ile Ile His Asn Val Asp Lys Asn Gly Asp
                              130                135                140
          Gly Leu Ile Asn Val Glu Glu Phe Gln Thr Met Met Thr Ser Glu Met
          145                     150                155                160
          Thr Asp Lys Ser Lys
                      165

<210> SEQ ID NO 41
<211> LENGTH: 347
<212> TYPE: PRT
<213> ORGANISM: Cupressus arizonica

<400> SEQUENCE: 41

Ser Asp Asn Pro Ile Asp Ser Cys Trp Arg Gly Asp Ser Asn Trp Asp
1               5                  10                 15
Gln Asn Arg Met Lys Leu Ala Asp Cys Val Val Gly Phe Gly Ser Ser
                20                 25                 30
Thr Met Gly Gly Lys Gly Gly Glu Ile Tyr Thr Val Thr Ser Ser Glu
            35                 40                 45
Asp Asn Pro Val Asn Pro Thr Pro Gly Thr Leu Arg Tyr Gly Ala Thr
    50                 55                 60
Arg Glu Lys Ala Leu Trp Ile Ile Phe Ser Gln Asn Met Asn Ile Lys
65                  70                 75                 80
Leu Gln Met Pro Leu Tyr Val Asn Gly Tyr Lys Thr Ile Asp Gly Arg
                85                 90                 95
Gly Ala Asp Val His Leu Gly Asn Gly Pro Cys Leu Phe Met Arg
            100                105                110
Lys Ala Ser His Val Ile Leu His Gly Leu His Ile His Gly Cys Asn
        115                120                125
Thr Ser Val Leu Gly Asp Val Leu Val Ser Glu Ser Ile Gly Val Glu
    130                135                140
Pro Val His Ala Gln Asp Gly Asp Ala Ile Thr Met Arg Asn Val Thr
145                 150                155                160
Asn Ala Trp Ile Asp His Asn Ser Leu Ser Asp Cys Ser Asp Gly Leu
                165                170                175
Ile Asp Val Thr Leu Gly Ser Thr Gly Ile Thr Ile Ser Asn Asn His
            180                185                190
Phe Phe Asn His His Lys Val Met Leu Leu Gly His Asp Asp Thr Tyr
        195                200                205
```

```
Asp Asp Asp Lys Ser Met Lys Val Thr Val Ala Phe Asn Gln Phe Gly
    210                 215                 220

Pro Asn Ala Gly Gln Arg Met Pro Arg Ala Arg Tyr Gly Leu Val His
225                 230                 235                 240

Val Ala Asn Asn Tyr Asp Gln Trp Asn Ile Tyr Ala Ile Gly Gly
            245                 250                 255

Ser Ser Asn Pro Thr Ile Leu Ser Glu Gly Asn Ser Phe Thr Ala Pro
            260                 265                 270

Asn Glu Ser Tyr Lys Lys Glu Val Thr Lys Arg Ile Gly Cys Glu Thr
            275                 280                 285

Thr Ser Ala Cys Ala Asn Trp Val Trp Arg Ser Thr Arg Asp Ala Phe
290                 295                 300

Thr Asn Gly Ala Tyr Phe Val Ser Ser Gly Lys Ala Glu Asp Thr Asn
305                 310                 315                 320

Ile Tyr Asn Ser Asn Glu Ala Phe Lys Val Glu Asn Gly Asn Ala Ala
                325                 330                 335

Pro Gln Leu Thr Gln Asn Ala Gly Val Val Ala
            340                 345

<210> SEQ ID NO 42
<211> LENGTH: 97
<212> TYPE: PRT
<213> ORGANISM: Homo sapiens

<400> SEQUENCE: 42

Met Cys Ser Ser Leu Glu Gln Ala Leu Ala Val Leu Val Thr Thr Phe
1               5                   10                  15

His Lys Tyr Ser Cys Gln Glu Gly Asp Lys Phe Lys Leu Ser Lys Gly
                20                  25                  30

Glu Met Lys Glu Leu Leu His Lys Glu Leu Pro Ser Phe Val Gly Glu
            35                  40                  45

Lys Val Asp Glu Glu Gly Leu Lys Lys Leu Met Gly Ser Leu Asp Glu
50                  55                  60

Asn Ser Asp Gln Gln Val Asp Phe Gln Glu Tyr Ala Val Phe Leu Ala
65                  70                  75                  80

Leu Ile Thr Val Met Cys Asn Asp Phe Phe Gln Gly Cys Pro Asp Arg
                85                  90                  95

Pro

<210> SEQ ID NO 43
<211> LENGTH: 291
<212> TYPE: DNA
<213> ORGANISM: Homo sapiens

<400> SEQUENCE: 43
atgtgcagtt ctctggagca ggcgctggct gtgctggtca ctaccttcca caagtactcc      60
tgccaagagg gcgacaagtt caagctgagt aaggggaaa tgaaggaact tctgcacaag     120
gagctgccca gctttgtggg ggagaaagtg gatgaggagg ggctgaagaa gctgatgggc    180
agcctggatg agaacagtga ccagcaggtg gacttccagg agtatgctgt tttcctggca    240
ctcatcactg tcatgtgcaa tgacttcttc cagggctgcc agaccgacc c              291

<210> SEQ ID NO 44
<211> LENGTH: 26
<212> TYPE: DNA
<213> ORGANISM: artificial
<220> FEATURE:
```

<223> OTHER INFORMATION: primer

<400> SEQUENCE: 44
aaggatccat gtgcagttct ctggag                                          26

<210> SEQ ID NO 45
<211> LENGTH: 26
<212> TYPE: DNA
<213> ORGANISM: artificial
<220> FEATURE:
<223> OTHER INFORMATION: primer

<400> SEQUENCE: 45
aacttaagca gggtcggtct gggcag                                          26

<210> SEQ ID NO 46
<211> LENGTH: 1436
<212> TYPE: DNA
<213> ORGANISM: Artificial
<220> FEATURE:
<223> OTHER INFORMATION: nucleotide sequence encoding a chimeric Protein

<400> SEQUENCE: 46
atgagaggat ctcaccacca ccaccaccac acggatccgc atgcgagctc gaacaacaac        60
aacaataaca ataacaacaa cctcgggatc gagggaaggc ctttagctac tcctcgcagc       120
gccaagaagg ccgtccgcaa gagcggctcc aagtccgcga atgtggtct gatcttcccg        180 gtgggccgcg tcggcgggat gatgcgccgc ggccagtacg ctcgccgcat cggtgcctct       240
ggcgccccca ggatttcaga attctccgtg aaggcggccg cgcagagcgg gaagaagcgg       300
tgccgcctga acccgcgcac cgtgatgctg gccgcgcgcc acgacgacga catcggcacg       360
cttctgaaga acgtgacctt gtctcacagc ggcgttgtgc cgaacatcag caaggcgatg       420
gcaaagaaga agggcggcaa gagggcaag gcgacaccga gcgcgcccga attcggatcc        480
tctagaccca tgtccaccaa gtacctcgcc gcgtacgctc tggcctccct gagcaaggcg       540
tccccgtctc aggcggacgt ggaggctatc tgcaaggccg tccacatcga cgtcgaccag       600 gccacccctcg cctttgtgat ggagagcgtt acggacgcg acgtggccac cctgatcgcg       660
gagggcgccg cgaagatgag cgcgatgccg gcggccagct ctggtgccgc tgctggcgtc       720
actgcttccg ctgcgggtga tgcggctccg gctgccgccg ccgcgaagaa ggacgagccc       780
gaggaggagg ccgacgacga catgggcccc tctagagtcg accccatgca gtacctcgcc       840
gcgtacgccc tcgtggcgct gtctggcaag acgccgtcga aggcggacgt tcaggctgtc       900
ctgaaggccg ccggcgttgc cgtggatgcc tcccgcgtgg atgccgtctt ccaggaggtg       960
gagggcaaga gcttcgatgc gctggtggcc gagggccgca cgaagctggt gggctctggc      1020
tctgccgctc ctgctggcgc tgtctccact gctggtgccg cgctggcgc ggtggccgag      1080 gcgaagaagg aggagcccga ggaggaggag gccgatgatg acatgggccc cgtcgacctg      1140 cagccccgccg ctgccgcgcc ggccgcccct agcgccgctg ccaaggagga gccggaggag      1200
agcgacgagg acgacttcgg catgggcggt ctcttctaag cgactcgcca tctcttagcc      1260
tccttgtggt gcgcttgagg tgctctcgct ctgcttctcc ttgcagtgtt ggctgactct      1320
ggcgggtatg tgccgtcgca ttacacccac ctctcccacc ccttttgccct acgcgctcgc      1380 atgcgcaatc cgtgaatcat cgagggaagt ctctctgggt ggcagtgggt aagctt          1436

<210> SEQ ID NO 47
<211> LENGTH: 412

```
<212> TYPE: PRT
<213> ORGANISM: Artificial
<220> FEATURE:
<223> OTHER INFORMATION: chimeric Protein

<400> SEQUENCE: 47

Met Arg Gly Ser His His His His His His Thr Asp Pro His Ala Ser
1               5                   10                  15

Ser Asn Asn Asn Asn Asn Asn Asn Asn Asn Leu Gly Ile Glu Gly
            20                  25                  30

Arg Pro Leu Ala Thr Pro Arg Ser Ala Lys Lys Ala Val Arg Lys Ser
            35                  40                  45

Gly Ser Lys Ser Ala Lys Cys Gly Leu Ile Phe Pro Val Gly Arg Val
50                  55                  60

Gly Gly Met Met Arg Arg Gly Gln Tyr Ala Arg Arg Ile Gly Ala Ser
65                  70                  75                  80

Gly Ala Pro Arg Ile Ser Glu Phe Ser Val Lys Ala Ala Gln Ser
            85                  90                  95

Gly Lys Lys Arg Cys Arg Leu Asn Pro Arg Thr Val Met Leu Ala Ala
            100                 105                 110

Arg His Asp Asp Asp Ile Gly Thr Leu Leu Lys Asn Val Thr Leu Ser
            115                 120                 125

His Ser Gly Val Val Pro Asn Ile Ser Lys Ala Met Ala Lys Lys Lys
        130                 135                 140

Gly Gly Lys Lys Gly Lys Ala Thr Pro Ser Ala Pro Glu Phe Gly Ser
145                 150                 155                 160

Ser Arg Pro Met Ser Thr Lys Tyr Leu Ala Ala Tyr Ala Leu Ala Ser
                165                 170                 175

Leu Ser Lys Ala Ser Pro Ser Gln Ala Asp Val Glu Ala Ile Cys Lys
            180                 185                 190

Ala Val His Ile Asp Val Asp Gln Ala Thr Leu Ala Phe Val Met Glu
            195                 200                 205

Ser Val Thr Gly Arg Asp Val Ala Thr Leu Ile Ala Glu Gly Ala Ala
    210                 215                 220

Lys Met Ser Ala Met Pro Ala Ala Ser Ser Gly Ala Ala Ala Gly Val
225                 230                 235                 240

Thr Ala Ser Ala Ala Gly Asp Ala Ala Pro Ala Ala Ala Ala Ala Lys
                245                 250                 255

Lys Asp Glu Pro Glu Glu Glu Ala Asp Asp Met Gly Pro Ser Arg
            260                 265                 270

Val Asp Pro Met Gln Tyr Leu Ala Ala Tyr Ala Leu Val Ala Leu Ser
        275                 280                 285

Gly Lys Thr Pro Ser Lys Ala Asp Val Gln Ala Val Leu Lys Ala Ala
        290                 295                 300

Gly Val Ala Val Asp Ala Ser Arg Val Asp Ala Val Phe Gln Glu Val
305                 310                 315                 320

Glu Gly Lys Ser Phe Asp Ala Leu Val Ala Glu Gly Arg Thr Lys Leu
                325                 330                 335

Val Gly Ser Gly Ser Ala Ala Pro Ala Gly Ala Val Ser Thr Ala Gly
            340                 345                 350

Ala Gly Ala Gly Ala Val Ala Glu Ala Lys Lys Glu Glu Pro Glu Glu
            355                 360                 365

Glu Glu Ala Asp Asp Asp Met Gly Pro Val Asp Leu Gln Pro Ala Ala
            370                 375                 380
```

-continued

```
Ala Ala Pro Ala Ala Pro Ser Ala Ala Ala Lys Glu Glu Pro Glu Glu
385                 390                 395                 400

Ser Asp Glu Asp Phe Gly Met Gly Gly Leu Phe
                405                 410
```

ADJUVANT

CROSS REFERENCE TO RELATED APPLICATIONS

The present application is the 35 U.S.C. 371 National Stage of International Application Number PCT/EP2011/069849, filed Nov. 10, 2011, which claims the benefit of U.S. Provisional Application No. 61/412,034, filed Nov. 10, 2010 and claims priority from European patent application EP10190705.3, filed Nov. 10, 2010, the contents of each of which are incorporated herein by reference.

A computer readable text file, entitled 2Rev-P6031289PCT-US-ST25, created on or about Sep. 26, 2013, with a file size of about 71 KB contains the sequence listing for this application and is hereby incorporated by reference in its entirety.

FIELD OF THE INVENTION

The invention relates to a new adjuvant and to its use as a vaccine in combination with an antigen..0

BACKGROUND OF THE INVENTION

Adjuvants are defined as substances whose role is to boost or direct antigen-specific immune responses when used in combination with specific antigens (Wack, A., et al (2005) Curr. Opin. Immunol. 17, 411-418). Usually, adjuvants combined with antigens, as is the case with all currently available commercial vaccines, do not induce immune responses against themselves. Due to the poor immunogenic properties of most antigens, adjuvants are used to enhance, activate and direct the innate and adaptive immune responses to those antigens. The concept of adjuvants has been extended to carriers that interact with surface molecules on specific cells of the immune system that operate at the interface between the immune system of the host and the administered antigen (Segal B H, et al, Drug Discov Today. 2006 June; 11(11-12):534-40). In doing so adjuvants help to stimulate the immune system and increase the response to the co-administered antigen. Therefore, adjuvants have been widely used for the development of vaccines.

Adjuvants can be classified according to their physio-chemical properties or mechanisms of action. The two major classes of adjuvants include compounds that directly act on the immune system such as bacterial toxins that stimulate immune responses, and molecules able to facilitate the presentation of antigens in a controlled manner and behaving as a carrier. At present, a large number of adjuvants are used to increase the immunological features of antigens including oils, aluminium salts, proteins and nucleic acid (Steven G. Reed, et al (2003) Expert Rev. Vaccines 2, 167-188).

In principle, due to the fact that the response against the antigen and the quality of the immune response will depend to a large extent on the purity and nature of the adjuvant. The ideal adjuvant should be chemically and physically well defined in such a way as to facilitate quality control. Since in most cases the antigens are well defined, the control of the adjuvant specificity will ensure reproducible development of the final antigen-specific immunological response. In this context, the adjuvants may not only elicit an immunological response against the antigen but also direct the immune response that the antigen elicited in the host. If the immune response goes in the appropriate direction, the nature of the adjuvant will substantially influence the value of the antigen as a therapeutic product. In addition to helping the induction of an immunological (humoral or cell-mediated) response against antigens, the objective of the adjuvant is to elicit immune effectors that result in the production of specific cytokines. Moreover, since the specificity and magnitude of immune responses induced by the antigen-adjuvant construct may largely depend on the nature of the host immune cells, the potency of the adjuvants cannot be analyzed without reference to the host. Thus, the immune responses induced by an antigen may vary depending on the nature of the adjuvant and of the nature of the host immune system.

There is always a need for new adjuvants since new vaccines are being developed and adjuvants are almost always needed in order to get an efficient induction of an immune response. New adjuvants may also confer new attractive properties to vaccines. For example, they can influence the type and direction of the immune response induced.

DESCRIPTION OF THE INVENTION

We surprisingly show that the genetic fusion of particular protein fragments originating from a *Leishmania* species to a defined antigen is able to significantly increase the immunogenic potentiality of the fused antigen when the resulting chimeric protein is administered in vivo to mice. We also show that the protein resulting from the in vivo expression of the chimeric gene present in a DNA plasmid also induces a high humoral response against the genetically fused antigen while the administration of the plasmid containing the gene coding for the antigen alone does not.

Nucleic Acid Molecule

In a first aspect there is provided a nucleic acid molecule represented by a nucleotide sequence selected from the group consisting of:
  i. nucleotide sequences encoding a polypeptide or a peptide comprising an amino acid sequence that has at least 50% sequence identity or similarity with the amino acid sequence of SEQ ID NO:1,
  ii. nucleotide sequences comprising a nucleotide sequence that has at least 50% sequence identity or similarity with the nucleotide sequence of SEQ ID NO:2,
  iii. nucleotide sequences the complementary strand of which hybridizes to a nucleic acid molecule of sequence of (i) or (ii) and
  iv. nucleotide sequences which differ from the sequence of a nucleic acid molecule under (iii) due to the degeneracy of the genetic code.

Said nucleic acid molecule is preferably for use as an adjuvant when said nucleic acid molecule is operably linked to a nucleotide sequence encoding an antigen as later defined herein.

A nucleic acid molecule described in this invention is attractive since the encoded protein can be used as an adjuvant. An adjuvant is defined herein as a molecule which is able to present an antigen to the immune system in such a way that an immune response, or an increase thereof, is elicited against said antigen when the antigen is administered in combination with the adjuvant. To analyze the antigen-specific elicited immune response, said immune response is compared to the immune response induced in presence of the antigen without the adjuvant. The induction is assessed in a subject or in cells from a subject.

In this context, the antigen-specific elicited immune response is synonymous with the induced immune response against said antigen or the increase in the induction of an immune response against said antigen or a detectable immune response against said antigen. Eliciting an antigen-specific immune response may be replaced with inducing, enhancing, or increasing an immune response against an antigen.

An immune response may be a B and/or a T cell response. An immune response may be a B cell response, i.e. production of an antibody specifically directed against said antigen. An antibody is preferably an IgG antibody, more preferably an IgG2a and/or an IgG1 antibody. An immune response may be a T cell response, preferably a Th1 response, a Th2 response or a balanced Th2/Th1 response. The skilled person knows that depending on the disease, a B and/or T cell response may be required to be induced to control it. The production of said antibody could be assessed by ELISA, preferably as carried out in the examples. Alternatively said immune response may be detected by measuring the production of cytokines such as, for example, IFNgamma, IL-6, TNFalpha, or IL-10. The production of such cytokines could be assessed by ELISA, preferably as carried out in the examples.

In a preferred embodiment, the detection of the antigen-specific elicited immune response means that said detection occurs after at least one, two, three, four, five, six, seven, eight, nine, ten, eleven, twelve hours or more or after at least one day of administration of said adjuvant and antigen, or at least two days, or at least three days, or at least four days or more. The detection is assessed in a subject or in cells from a subject, preferably as carried out in the examples.

In the context of the invention, the antigen-specific elicited immune response preferably means a detectable immune response against said antigen. A detectable increase is preferably an increase of at least 5% of the amount of an antibody and/or of a cytokine as already identified herein, or 10%, 15%, 20%, 25%, 30%, 35%, 40%, 45%, 50%, 55%, 60%, 65%, 70%, 75%, 80%, 85%, 90%, 95%, 100%, 150%, 200% or more after at least one, two, three, four, five, six, seven, eight, nine, ten, eleven, twelve hours or more or after at least one day of administration of said adjuvant and antigen, or at least two days, or at least three days, or at least four days or more. The detection is assessed in a subject or in cells from a subject, preferably as carried out in the examples.

Preferably, said amino acid sequence and/or or nucleotide sequence having at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity or similarity with a specific identified amino acid and/or nucleotide sequence as defined earlier herein (SEQ ID NO:1 respectively SEQ ID NO:2) are said to be functional when the encoded polypeptide qualifies as an adjuvant. Said polypeptide, represented by said amino acid sequence, is capable of eliciting, inducing, enhancing, or increasing an immune response against an antigen when used with said antigen to at least some extent. To "at least some extent" preferably means that at least 50%, at least 60%, at least 70%, at least 80%, at least 90% or 100% of the antigen-specific immune response detected using SEQ ID NO:1. Eliciting, inducing, enhancing, or increasing an immune response against an antigen has been earlier defined herein.

A nucleic acid molecule as defined herein is preferably a molecule comprising at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or more contiguous nucleotides of SEQ ID NO:2, and whose encoded polypeptide is able to elicit, induce, enhance, or increase an immune response against an antigen when used with an antigen as earlier defined herein. In a preferred embodiment, said nucleic acid molecule as defined herein is preferably a molecule comprising at least 762, 765, 770, 780, 790, 800, 810, 820, 830, 840 850, 860, 870, 880, 890, 900, 910, 920, 930, 940, 950, 960, 970, 980, 990, 1000 or 1110 contiguous nucleotides of SEQ ID NO: 2. In a preferred embodiment, said nucleic acid molecule as defined herein is preferably a molecule comprising at most 1110, 1000, 990, 980, 970, 960, 950, 940, 930, 920, 910, 900, 890, 880, 870, 860, 850, 840, 830, 820, 810, 800, 790, 780, 770 or 765 contiguous nucleotides of SEQ ID NO: 2.

A polypeptide as defined herein is preferably a polypeptide comprising at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or more contiguous amino acids of SEQ ID NO:1 and which is able to elicit, induce, enhance, or increase an immune response against an antigen when used with an antigen as earlier defined herein. In a preferred embodiment, said nucleic acid molecule as defined herein is preferably a molecule comprising at least 254, 260, 270, 280, 290, 300, 310, 320, 330, 340, 350, 360 or 370 contiguous amino acids of SEQ ID NO: 1. In a preferred embodiment, said nucleic acid molecule as defined herein is preferably a molecule comprising at most 370, 360, 350, 340, 330, 320, 310, 300, 290, 280, 270, 260 or 254, contiguous amino acids of SEQ ID NO: 1. The polypeptide consisting of SEQ ID NO:1 is also called AAP (Augmentor and Activator Protein).

An amino acid or nucleotide sequence, encompassed by the present invention, may be derived from one of the sequences as identified herein by substituting, inserting, deleting, or adding one, 2, 3, 4, 5, 6, 7, 8, 9, 10 or more nucleotides or amino acids, respectively. An amino acid sequence, encompassed by the present invention, may be derived from one of the sequences as identified herein by adding additional N- or C-terminal amino acids or chemical moieties to increase stability, solubility and immunogenicity. In an embodiment, an amino acid sequence encompassed by the present invention is derived from SEQ ID NO:1 by conservative substitution of at least one amino acid present in SEQ ID NO:1. Said amino acid that may be replaced may be a histidine. The skilled person knows that histidine may be substituted by asparagine or glutamine (i.e. conservative substitution as later defined herein). Therefore in an embodiment, an amino acid sequence encompassed by the invention is derived from SEQ ID NO:1 and comprises 1, 2, 3, 4, 5, or 6 histidines at the most. Accordingly, in an embodiment, a nucleic acid sequence encompassed by the invention is derived from SEQ ID NO:2 and encodes for an amino acid sequence that comprises 1, 2, 3, 4, 5, or 6 histidines at the most. In an embodiment, said amino acid sequence does not comprise any histidine and/or said corresponding nucleic acid sequence codes for an amino acid sequence that does not comprise a histidine.

Accordingly, in an embodiment, a nucleic acid molecule is represented by a nucleotide sequence selected from the group consisting of:
  i. nucleotide sequences encoding a polypeptide or a peptide comprising an amino acid sequence that has at least 50% sequence identity or similarity with the amino acid sequence of SEQ ID NO:1,
  ii. nucleotide sequences comprising a nucleotide sequence that has at least 50% sequence identity or similarity with the nucleotide sequence of SEQ ID NO:2,
  iii. nucleotide sequences the complementary strand of which hybridizes to a nucleic acid molecule of sequence of (i) or (ii) and
  iv. nucleotide sequences which differ from the sequence of a nucleic acid molecule under (iii) due to the degeneracy of the genetic code
and wherein said nucleic acid molecule codes for an amino acid sequence that comprises 1, 2, 3, 4, 5 or 6 histidines at the most. Preferably said nucleic acid molecule codes for an amino acid sequence that does not comprise a histidine. Preferably in said nucleic acid molecule, at least one codon coding for histidine or at least 2, 3, 4, 5 or 6 codon coding for histidines have been substituted by a codon coding for asparagine or glutamine.

In a preferred embodiment, a nucleic acid molecule of the invention being represented by a nucleotide sequence as defined earlier herein further comprises a nucleotide sequence encoding an antigen. We found that the immune response elicited by an adjuvant of the invention was optimal when the corresponding nucleotide sequence encoding an antigen was comprised within, or fused to, or operably linked to, a nucleic acid molecule encoding the adjuvant as earlier defined herein. Therefore the adjuvant of the invention is preferably used in such a way that its encoding nucleotide sequence is fused to or operably linked with a nucleotide sequence encoding an antigen.

In a preferred embodiment, said nucleic acid molecule of the invention is free of or does not comprise a sequence encoding for a polypeptide is identical or is at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75% to SEQ ID NO: 3 over its entire length.

An antigen is defined herein as a molecule which is able to be recognized by an antibody raised against said antigen when said molecule is present in a subject. An antigen which is able to induce a specific immune response from a subject when said antigen is present in said subject is said to be immunogenic or to be an immunogen. An immune response is preferably as defined earlier herein. An antigen is preferably a polypeptide or a peptide. A peptide may comprise 6, 7, 8, 9, 10, 11, 12, 13, 14, 15, 16, 17, 18, 19, 20, 21, 22, 23, 24, 25, 26, 27, 28, 29, 30 amino acids or more. An antigen may be a protein fragment or a full length protein originating from an organism as identified later herein. It is also possible to use several antigens from the same organism in order to be more effective in combating the organism. An antigen may also be defined by reference to an encoding nucleic acid molecule represented by a nucleic acid sequence.

The source of an antigen may be a protein, a digest of the protein and/or a fragment thereof, which may be in a purified form or may be comprised within a crude composition, preferably of biological origin, such as a bacterial lysate, parasitic lysate, yeast lysate, viral lysate, fungal lysate, sonicate or fixate. Alternatively, an antigen may be chemically synthesized or enzymatically produced in vitro. The source of a protein, or fragment thereof as antigen, may also be a nucleic acid encoding said, or fragment thereof, from an RNA or DNA template. The RNA or DNA molecules may be 'naked' DNA, preferably comprised in vesicles or liposomes, or they may be comprised in a nucleic acid construct or a vector. The vector may be any (recombinant) DNA or RNA vector known in the art, and preferably is a plasmid; wherein genes encoding latency antigens are operably linked to regulatory sequences conferring expression and translation of the encoded messengers. The vector may also be any DNA or RNA virus, such as, but not limited to, Adenovirus, Adeno-Associated Virus (AAV), a retrovirus, a lentivirus, modified Vaccinia Ankara virus (MVA) or Fowl Pox virus, or any other viral vector capable of conferring expression of a polypeptide into a chosen subject. DNA vectors may be non-integrating, such as episomally replicating vectors, or may be vectors integrating in the host genome by random integration or by homologous recombination.

DNA molecules comprising genes encoding an antigen protein, or fragments thereof according to the current invention, optionally embedded in a vector such as a virus or plasmid, may be integrated in a genome of a subject. In a preferred embodiment of the invention, such a host may be a micro-organism. Preferably such a recombinant micro-organism is a *Mycobacterium*, for instance of the species *M. tuberculosis*, *M. smegmatis* or *M. bovis* and most preferably *M. bovis* Bacillus Calmette Guerin (BCG) or *M. smegmatis*, capable of delivering to a host the polypeptides or fragments thereof according to the invention (as described in Yue. Y. et al, (2007), J. Virol. Meth., 141: 41-48, Cayabiyab Y. et al, (2006), J. Virol., 80: 1645-1652). Recombinant BCG and methods for recombination are known in the art; for instance, in WO2004094469. Such a recombinant micro-organism may be formulated as a live recombinant and/or live attenuated vaccine, as shown in Jacobs et al. 1987, Nature, 327 (6122):532-5. The vector may also be comprised in a host of bacterial origin, such as, but not limited to, live-attenuated and/or recombinant *Shigella* or *Salmonella* bacteria.

In the context of the invention, a subject means a human or an animal. An animal which is encompassed within the scope of the invention includes a mammal, preferably a dog.

An antigen may originate from any organism known to be associated with a disease or a condition in a subject. An antigen may originate from a microorganism such as a bacterium, a yeast, a fungus, a parasite. Alternatively an antigen may originate from a virus. An antigen may also be a self or auto antigen as, for example, those associated or linked with cancer or a tumor antigen. Antigens may also be associated with or linked to allergic diseases.

A disease may be a parasitic disease. In this case, an antigen may originate from a protozoan belonging to the apicomplexa (such as *Plasmodium*) and/or kinetoplastidae phylum, and in particular members of the trypanosomatid family, more in particular different species of the trypanosomatical protozoan *Leishmania*. There are over 20 known species of *Leishmania*, including species of the subgenus *Leishmania*, comprising the complex *L. major*, including *L. major*, the complex *L. Donovani*, including *L. chagasi, L. donovani* and *L. infantum*, the complex *L. Mexicana*, including *L. amazonensis* and *L. mexicana*, as well as the subspecies *Viannia*, comprising the complex *L. braziliensis*, including *L. braziliensis* and *L. peruviana* and the complex *L. guyanensis*, including *L. guyanensis* and *L. panamensis*. In a preferred embodiment, an antigen originates from a *Leishmania* species, preferably *Leishmania major* and/or *Leishmania infantum*. In another preferred embodiment, an antigen originates from a *Plasmodium* species. *Plasmodium* species of particular interest are *Plasmodium falciparum* and *Plasmodium vivax*.

For example, if an antigen originates from a parasite, preferably from a *Leishmania* species causing leishmaniasis, said compounds could be selected from a group consisting of a source of other proteins from a parasite causing a parasitic disease as described in the publication by Iborra, S. et al. (Iborra, S., et al 2004. Vaccine 22:3865-76). A preferred protein source of antigens is in this context a histone such as a H2A, H2B, H3, H4, or a ribosomal protein such as L1P0, L2, L7, L8, L16, S6, L3, L5 and S4. A preferred H2A protein is represented by SEQ ID NO:3. A preferred nucleic acid encoding a H2A is represented by SEQ ID NO:4. A preferred H2B protein is represented by SEQ ID NO:5. A preferred nucleic acid encoding a H2B is represented by SEQ ID NO:6. A preferred H3 protein is represented by SEQ ID NO:7. A preferred nucleic acid encoding a H3 is represented by SEQ ID NO:8. A preferred H4 protein is represented by SEQ ID NO:9. A preferred nucleic acid encoding a H4 is represented by SEQ ID NO:10. A preferred LiP0 protein is represented by SEQ ID NO:11. A preferred nucleic acid encoding a L1P0 is represented by SEQ ID NO:12. A preferred L2 protein is represented by SEQ ID NO:13. A preferred nucleic acid encoding L2 is represented by SEQ ID NO:14. A preferred L7 protein is represented by SEQ ID NO:15. A preferred nucleic acid encoding a L7 is represented by SEQ ID NO:16. A preferred L8 protein is represented by SEQ ID NO:17. A preferred nucleic acid encoding a L8 is represented by SEQ ID NO:18. A preferred L16 protein is represented by SEQ ID NO:19. A preferred nucleic acid encoding a L16 is represented by SEQ ID NO:20. A preferred S4 protein is represented by SEQ ID NO:21. A preferred nucleic acid encoding a S4 is represented by SEQ ID NO:22. A preferred S6 protein is represented by SEQ ID NO:23. A preferred nucleic acid encoding a S6 is represented by SEQ ID NO:24. A preferred L3 protein is represented by SEQ ID NO:25. A preferred nucleic acid encoding a L3 is represented by SEQ ID NO:26. A preferred L5 protein is represented by SEQ ID NO:27. A preferred nucleic acid encoding a L5 is represented by SEQ ID NO:28.

Another example is the use of poly-proteins containing several parasite antigens as seen in Stober et al and Aebischer, et al and Poot et al. (Stober C. B. U. G., et al (2006), *Vaccine.*, 24: 2602-2616; Aebischer T., et al, (2000) *Infection and Immunity.*, 68: 1328-1336; and Poot J et al, (2009), *Vaccine*, 27: 4439-4446).

A histone protein may also be used as a protein source of antigens. Preferred compounds include a histone protein or fragment thereof, or a nucleic acid molecule encoding said histone or said histone fragment. More preferably, a histone protein is H2A, H2B, H3 and/or H4 as identified in EP 1 687 023. Histones H2A, H2B, H3 and H4 are well-conserved nuclear proteins and their sequences are well-known in the art (Requena, J. M., et al 2000; Parasitol Today 16:246-50).

Preferably, the histones are obtained from an organism which is close to the disease causing organism in the evolutionary tree. Therefore, of particular interest as a source of histones to be used in the treatment of parasitic diseases such as Leishmaniasis are protozoans, as for example *plasmodium*. Additionally, of interest are members of the trypanosomatid family, more in particular different species of the trypanosomatical protozoan *Leishmania*.

Other preferred compounds include other ribosomal protein or fragment thereof or a nucleic acid molecule encoding said protein or fragment thereof. Examples of other ribosomal proteins include L19 and S4.

Other preferred compounds include a Ribosomal Protein Extract as identified in WO 2009/090175.

A disease may include, but is not limited to, allergy or a cancer. Any type of antigen known to be associated or be specific with a cancer may be used in the context of the invention. Such type of antigen may also be named a tumor antigen. A tumor antigen may be a protein product of a mutated oncogene or a mutated tumor suppressor gene, or a protein product of any gene or mutated gene known to be expressed in a tumor or in a cancer. A tumor antigen may be a protein product of an overexpressed or aberrantly expressed gene. A tumor antigen may be a protein product of an oncogenic virus. A tumor antigen may be a protein product of an oncofetal gene. Examples of tumor antigen include protein product of the following genes: alphafetoprotein (AFP), carcinoembryonic antigen (CEA), epithelial tumor antigen (ETA), Melanoma-associated antigen (MAGE), p53 or CD20. A tumor antigen as defined herein may also be part of a protein product, i.e. a polypeptide, a peptide derived from a protein product of a gene as identified herein.

A preferred cancer antigen include CD20 or a fragment thereof. CD20 is expressed in some B cell malignancies. A preferred amino acid sequence representing CD20 is identified as SEQ ID NO:37. A preferred antigen in this context comprises 6, 7, 8, 9, 10, 11, 12, 13, 14, 15, 16, 17, 18, 19, 20, 21, 22, 23, 24, 25, 26, 27, 28, 29, 30 contiguous amino acids or more of SEQ ID NO:37 and/or has at least 50, 55, 60, 65, 70, 75, 80, 85, 90, 95 or 99% identity or similarity with SEQ ID NO:37.

A cancer may be gastric ademoma and/or breast tumour. A preferred cancer antigen includes a S100A2 protein or a fragment thereof. The S100A2 protein is a calcium-binding protein that is up regulated in association with human gastric adenocarcinoma (1) and breast (2) tumour progression. A preferred amino acid sequence representing S100A2 is identified as SEQ ID NO: 42. A preferred nucleic acid sequence coding for a preferred S100A2 is identified a SEQ ID NO: 43. A preferred antigen in this context comprises 6, 7, 8, 9, 10, 11, 12, 13, 14, 15, 16, 17, 18, 19, 20, 21, 22, 23, 24, 25, 26, 27, 28, 29, 30 contiguous amino acids or more of SEQ ID NO:42 and/or has at least 50, 55, 60, 65, 70, 75, 80, 85, 90, 95 or 99% identity or similarity with SEQ ID NO:42.

A disease may also be allergy. An antigen may also be associated with or linked to an allergic disease. Examples of preferred allergic antigens include an allergen from a *Cupressus* species, preferably *Cupressus arizonica* (Cupa4 or Cupa1). A preferred nucleic acid sequence representing coding for a preferred Cupa4 is identified as SEQ ID NO:38. A preferred nucleic acid sequence representing coding for a preferred Cupa1 is identified as SEQ ID NO:39. A preferred amino acid sequence representing a preferred Cupa4 is identified as SEQ ID NO:40. A preferred amino acid sequence representing a preferred Cupa1 is identified as SEQ ID NO:41. A preferred antigen in this context comprises 6, 7, 8, 9, 10, 11, 12, 13, 14, 15, 16, 17, 18, 19, 20, 21, 22, 23, 24, 25, 26, 27, 28, 29, 30 contiguous amino acids or more of an amino acid sequence encoded by SEQ ID NO:38 or 39 and/or has at least 50, 55, 60, 65, 70, 75, 80, 85, 90, 95 or 99% identity or similarity with an amino acid sequence encoded by SEQ ID NO:38 or 39.

Another preferred antigen in this context comprises 6, 7, 8, 9, 10, 11, 12, 13, 14, 15, 16, 17, 18, 19, 20, 21, 22, 23, 24, 25, 26, 27, 28, 29, 30 contiguous amino acids or more of an amino acid sequence represented by SEQ ID NO:40 or 41 and/or has at least 50, 55, 60, 65, 70, 75, 80, 85, 90, 95 or 99% identity or similarity with an amino acid sequence represented by SEQ ID NO:40 or 41.

However, the skilled person will understand that the invention is not limited to this specific antigen.

Each of the antigens identified herein (i.e. proteins, parts thereof, polypeptide or peptide) is preferably used with or fused to a polypeptide being an adjuvant as earlier defined herein. It means that in a preferred embodiment, a nucleic acid molecule encoding an antigen is operably linked with a nucleic acid molecule of the invention as earlier defined herein whose encoded polypeptide functions as an adjuvant. In a more preferred embodiment, said nucleic acid molecule encoding an antigen being operably linked with a nucleic acid molecule of the invention as earlier defined herein encoding a polypeptide which functions as an adjuvant is one single nucleic acid molecule, encoding one single polypeptide. Said polypeptide may be called a chimeric polypeptide. This chimeric polypeptide comprises or consists of an antigen fused to an adjuvant of the invention. This chimeric polypeptide may comprise one or more additional amino acids at the 5' and/or at the 3' and/or between the antigen and the adjuvant.

The invention therefore provides a nucleic acid molecule as earlier defined herein encoding a polypeptide which is able to behave as an adjuvant for a given antigen, when this nucleic acid sequence is operably linked to a nucleotide sequence encoding said antigen. In a preferred embodiment, this nucleic acid molecule encodes a polypeptide which is able to induce an antigen-specific immune response in a subject. Therefore the invention encompasses two types of nucleic acid molecules:
- one comprising or consisting of a nucleic acid molecule encoding an adjuvant,
- one comprising or consisting of a nucleic acid molecule encoding an adjuvant fused to a nucleic acid molecule encoding an antigen.

Depending on the type of source used (protein-based or nucleic acid-based), the skilled person will know which type of formulation is suited. An antigen may be administered as such (naked protein or nucleic-acid). Alternatively, a nucleic acid-based source may be administrated using a nucleic acid construct as defined herein. Preferably a protein-based formulation is chosen. More preferably, a chimeric polypeptide as earlier identified herein is used.

In another embodiment, an antigen may originate from a virus. Any virus that causes a disease in humans from which antigens are known is encompassed within the scope of the present invention.

In an other embodiment, an antigen may originate from a yeast, a fungus, an allergen or a cancer cell or any other pathological cell. Any yeast or fungus that causes a disease in humans from which antigens are known is encompassed within the scope of the present invention.

Accordingly, a nucleic acid molecule of the invention encodes a polypeptide, preferably a chimeric polypeptide as identified herein which is able to induce an antigen-specific immune response when said nucleic acid molecule comprises a nucleotide sequence encoding an antigen.

Polypeptide

In a further aspect, there is provided a polypeptide encoded by a nucleic acid molecule as earlier identified herein. This polypeptide comprises an adjuvant and preferably an antigen as defined in the previous section.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

Nucleic Acid Construct

In a further aspect, there is provided a nucleic acid construct comprising a nucleic acid molecule as identified in the previous section. This nucleic acid construct may comprise a nucleic acid molecule encoding a polypeptide defined as an adjuvant in the previous section. This nucleic acid construct may comprise a nucleic acid molecule encoding a polypeptide defined as an adjuvant and a nucleic acid molecule encoding an antigen as defined in the previous section.

The invention also relates to an expression vector comprising a nucleic acid construct of the invention. Preferably, an expression vector comprises a nucleotide sequence of the invention, which is operably linked to one or more control sequences, which direct the production or expression of the encoded polypeptide in a cell, a subject, or a cell-free expression system. An expression vector may be seen as a recombinant expression vector.

Accordingly, a nucleic acid molecule as defined herein encoding a polypeptide comprising or consisting or composed of an adjuvant, is preferably for use as a medicament, more preferably as an adjuvant. Accordingly, said polypeptide is preferably for use as a medicament, more preferably as an adjuvant.

Accordingly, a nucleic acid molecule as defined herein encoding a polypeptide comprising or consisting or composed of an adjuvant and an antigen is preferably for use as a medicament, more preferably as a vaccine against said antigen. Accordingly, said polypeptide is preferably for use as a medicament, more preferably as a vaccine against said antigen.

A vaccine of the invention may function as a therapeutic vaccine. Typically, there is a time period between contact with an antigen, i.e. infection and apparition of the first symptom of a disease associated with said antigen. In this case, a vaccine would act as a pharmacological immune product that would prevent and/or treat the disease and/or delay its progression by eliciting in the host an immune response that counteracts the pathological effect of the disease. A therapeutic vaccine differs from a prophylactic vaccine in that a therapeutic vaccine will induce protection in a subject who already has the infection or the disease. In another embodiment, a vaccine is a prophylactic vaccine. A prophylactic vaccine may be administered to a subject before said subject has been contacted with said antigen.

A medicament as defined herein is preferably administered parenterally, e.g. by injection or infusion by intravenous, subcutaneous, intraperitoneal, intramuscular, intraarterial or intralesional route. A preferred administration mode is subcutaneous. A medicament may be combined with a pharmaceutically acceptable medium or delivery vehicle by conventional techniques known in the art. For example, a medicament may be dissolved in Phosphate buffer saline (PBS). Methods for preparing parenterally administrable compositions are well known in the art and described in more detail in various sources, including, for example, Remington's Pharmaceutical Sciences, Ed. A R Gennaro, 20th edition, 2000, Williams & Wilkins, PA, USA. A medicament is preferably administered in a therapeutically effective dose, i.e. one that will increase the ability of the human or animal immune system to fight a disease or condition as defined herein. Preferably, a therapeutically effective dose of a medicament of the invention will prevent and/or delay the development of said disease or condition. Depending on the disease or the condition, the skilled person will know which parameter or symptom associated with the development of said disease to choose in order to follow the development of the disease or condition.

The invention further encompasses the use of another distinct known adjuvant in addition to a nucleic acid molecule or a polypeptide of the invention. Any known adjuvant may be used in the present invention. The skilled person knows several suitable adjuvants. Adjuvants are most preferably selected from the following list of adjuvants: cationic (antimicrobial) peptides, saponine and Toll-like receptor (TLR) ligands such as, but not limited to, poly(I:C), CpG motifs, LPS, lipid A, lipopeptide Pam3Cys and bacterial flagellins or parts thereof, and their derivatives having chemical modifications. Other preferred adjuvants for use in the method and in compositions according to the invention are: mixtures with live or killed BCG, immunoglobulin complexes with the said latency antigens or parts thereof, IC31 (from www.intercell.com; in WO03047602), QS21/MPL (US2003095974), DDA/MPL (WO2005004911), DA/TDB (WO2005004911; Holten-Andersen et al, 2004 Infect Immun. 2004 March; 72(3):1608-17) and soluble LAG3 (CD223) (from www.Immunotep.com; US2002192195). In addition, another preferred adjuvant includes the use of *Corynebacterium paryum* or *Propionobacterium acnes* (Aebischer T., et al, (2000)

Infection and Immunity, 68: 1328-1336, Poot J et al, (2009), Vaccine, 27: 4439-4446 and Ferreira J. H. et al, (2008), Vaccine, 26: 67-685).

Particularly preferred adjuvants are those that are known to act via the Toll-like receptors. Adjuvants that are capable of activation of the innate immune system, can be activated particularly well via Toll like receptors (TLR's), including TLR's 1-10 and/or via a RIG-1 (Retinoic acid-inducible gene-1) protein and/or via an endothelin receptor. Compounds capable of activating TLR receptors, and modifications and derivatives thereof, are well documented in the art. TLR1 may be activated by bacterial lipoproteins and acetylated forms thereof; TLR2 may, in addition, be activated by Gram positive bacterial glycolipids, LPS, LPA, LTA, fimbriae, outer membrane proteins, heatshock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines and derivatives. TLR9 may be activated by unmethylated CpG DNA or chromatin-IgG complexes. In particular TLR3, TLR4, TLR7 and TLR9 play an important role in mediating an innate immune response against viral infections, and compounds capable of activating these receptors are particularly preferred for use in the invention. Particularly preferred adjuvants comprise, but are not limited to, synthetically produced compounds comprising dsRNA, poly(I:C), unmethylated CpG DNA which trigger TLR3 and TLR9 receptors, IC31, a TLR9 agonist, IMSAVAC, a TLR4 agonist. In another preferred embodiment, an adjuvant is physically linked to a nucleic acid molecule as earlier defined herein. Physical linkage of adjuvants and costimulatory compounds or functional groups to the HLA class I and HLA class II epitope comprising peptides, provides an enhanced immune response by simultaneous stimulation of antigen presenting cells, in particular dendritic cells, whose role is to internalize, metabolize and display antigens. Another preferred immune modifying compound is a T cell adhesion inhibitor, more preferably an inhibitor of an endothelin receptor such as BQ-788 (Buckanovich R. J., et al, (1994), Proc. Natl. Acad. Sci. USA, 91:4892). BQ-788 is N-cis-2,6-dimethylpiperidinocarbonyl-L-gamma-methylleucyl-D-1-methoxycarbonyltryptopha-nyl-D-norleucine. However any derivative of BQ-788 or modified BQ-788 compound is also encompassed within the scope of this invention.

Other adjuvants include MPL-SE (Glaxo Smithkline Biologicals, Belgium) or EM005 (IDRI, USA).

In a preferred embodiment, an adjuvant is a $Th_1$-promoting adjuvant (like an adjuvant comprising a CpG ODN motif). A Th1-promoting adjuvant has been defined in the literature (Liu N., et al (2003), Nature Immunology, 687-693) as an adjuvant which is able to promote, or trigger, or induce, or induce an increase of, a $Th_1$ immune response against a given antigen when used together with this antigen as detected in supernatants of splenocytes of a treated subject when cultured with the antigen. As control, the promotion, or triggering, of a Th1 immune response is assessed in a splenocyte population of the same subject which has not been treated with the antigen and the adjuvant, or with same population only treated with the antigen. Triggering or promoting a $Th_1$ immune response is preferably defined by the induction of IFNγ as detected by culturing splenocytes of a treated subject with the antigen and/or by inducing the production of antigen-specific IgG2a immunoglobulins. The assessment of the induction of this cytokine and of IgG2a has already been defined herein. In a preferred embodiment, a Th-1 promoting adjuvant is, or comprises, or consists of, an oligodeoxynucleotide. More preferably, an oligodeoxynucleotide (ODN) comprises, or consists of, CpG in which the C is non-methylated (CpG ODN): 3' purine-CpG-5' pyrimidine. A preferred oligodeoxynucleotide is, or comprises, or consists of, a phosphorothioate-modified ODN sequence. The use of oligodeoxynucleotides having such modification is advantageous since the oligodeoxynucleotides hence used are more stable than non modified oligonucleotides and hence will not easily be degraded once they are in the blood stream. A preferred Th-1 promoting adjuvant consists of, or comprises, at least one CpG motif, at least two, or at least three. Preferred sequences of the immunostimulatory ODN (5' to 3') were TCAACGTTGA (SEQ ID NO:29) and GCTAGCGT-TAGCGT (SEQ ID NO:30). The skilled person is not limited to the sequences explicitly described herein. He/she may design other sequences conveying the Th-1 promoting property as defined earlier herein.

In a preferred embodiment, a medicine (or medical preparation or pharmaceutical composition or medicament) as defined herein is used to increase the ability of a subject's immune system to fight against an infection and/or a disease, more preferably a parasitic infection and/or a parasitic disease. In particular, it may be used for administration to a human or animal subject. A medicine as defined herein is preferably administered parenterally, e.g. by injection or infusion by intravenous, subcutaneous, intraperitoneal, intramuscular, intraarterial, intranasal, or intralesional route. A preferred administration mode is subcutaneous. The invention is not limited to a specific mode of administration of a medicament or a nucleic acid molecule or a nucleic acid construct or a peptide or a polypeptide as defined herein. A preferred mode of administration is oral administration using a capsule or a tablet. Alternatively a medicament or a nucleic acid molecule or a nucleic acid construct or a peptide or a polypeptide as defined herein may be locally administered via a catheter or a pump, or a suppository. Alternatively, a medicament or a nucleic acid molecule or a nucleic acid construct or a peptide or a polypeptide as defined herein may be topically administered. The formulation of a medicament or a nucleic acid molecule or a nucleic acid construct or a peptide or a polypeptide as defined herein or of a composition comprising said compounds depends on the intended mode of administration and (therapeutic) application. A pharmaceutical carrier can be any compatible, non toxic substance suitable to deliver said compound to a subject. E.g. sterile water, or inert solids or excipients may be used as the carrier, usually complemented with pharmaceutically acceptable adjuvants, buffering agents, dispersing agents, and the like. Compositions will either be in liquid, e.g. a stabilized suspension of said compound, or a composition comprising said compound, or in solid and/or dry forms: e.g. powder. For oral and rectal administration, said compound can be administered in solid dosage forms, such as capsules, tablets, suppositories, and powders, or in liquid dosage forms, such as elixirs, syrups, creams, ointments, enemas, and suspensions. Another form may be a semi-solid or semi-liquid form wherein said compound is present as a liquid form in, or on, a solid support such as a patch.

A medicine may be combined with a pharmaceutically acceptable medium or delivery vehicle by conventional techniques known in the art. For example, a medicament or a nucleic acid molecule or a nucleic acid construct or a peptide or a polypeptide as defined herein, and optionally a second adjuvant, may be dissolved in Phosphate buffer saline (PBS). Methods for preparing parenterally administrable compositions are well known in the art and described in more details in various sources, including, for example, Remington's Pharmaceutical Sciences, Ed. A R Gennaro, 20th edition, 2000, Williams & Wilkins, PA, USA. A medicine is preferably administered in a therapeutically effective dose, i.e. one that will increase the ability of the human or animal immune system to fight an infection and/or a disease as defined herein. Preferably, a therapeutically effective dose of a medical preparation of the invention is able to elicit an immune response as defined herein: a dose is therapeutically effective when it is able to elicit the proper immune response, or induce or induce an increase of the proper immune response against a specific antigen in a treated subject as defined herein. Even more preferably, the elicited or induced immune response is a protective immune response. In a preferred embodiment, a medicine as defined herein is a vaccine. In a more preferred embodiment, at least 5, 10, 15 or 20 micrograms of a nucleic acid molecule or a nucleic acid construct or a peptide or a polypeptide as defined herein is being used in a vaccine. Said vaccine may be administered at least once, twice, three times, four times or more. A vaccine, as defined herein, may be a prophylactic or a therapeutic vaccine. The volume in which a nucleic acid molecule or a nucleic acid construct or a peptide or a polypeptide as defined herein may be dissolved may vary from 100-500 microliters.

Composition

Additionally, there is provided a composition comprising a nucleic acid molecule or a nucleic acid construct or a peptide or a polypeptide and optionally a second adjuvant, preferably a $Th_1$-promoting adjuvant. Each feature of said composition has already been defined herein. In a preferred embodiment, this composition consists of a nucleic acid molecule or a nucleic acid construct or a peptide or a polypeptide as identified herein, a preferred $Th_1$-promoting adjuvant is a CpG ODN. A preferred composition comprises or consists of a nucleic acid molecule or a nucleic acid construct or a peptide or a polypeptide and optionally a second adjuvant, preferably a $Th_1$-promoting adjuvant dissolved in PBS or a suitable buffer. As already defined herein, an antigen may already be present as being comprised within said peptide or polypeptide or as being encoded by part of said nucleic acid molecule or being encoded by part of the nucleic acid molecule present in said nucleic acid construct. In a further preferred embodiment, it is also encompassed by the present invention that a nucleic acid molecule or a nucleic acid construct or a peptide or a polypeptide and optionally a second adjuvant, preferably a Th1-promoting adjuvant are sequentially administered. Therefore, each component does not need to be physically present in one single composition as long as they are both administered to a subject.

Such composition may further comprise a pharmaceutically acceptable adjuvant and/or carrier.

Such composition is preferably for use as a medicine or as a medicament. The medicine is preferably a vaccine. Medicine, adjuvant and vaccine have already been extensively defined herein.

A composition may be in the liquid, solid or semi-liquid or semi-solid form as already defined herein.

In a preferred embodiment, other compounds are used sequentially or simultaneously with a nucleic acid molecule or a nucleic acid construct or a peptide or a polypeptide in order to improve the specificity of the therapeutic or prophylactic treatment. It is advantageous for example to use other compounds that will further enhance the immune response of the treated subject. More preferably, such compounds are not present in a single composition together with a nucleic acid molecule or a nucleic acid construct or a peptide or a polypeptide.

Use

Accordingly, there is further provided the use of a nucleic acid molecule as identified herein encoding an adjuvant and a nucleic acid molecule encoding an antigen, a corresponding peptide, a corresponding polypeptide, a corresponding nucleic acid construct and/or a corresponding composition for the manufacture of a medicament for treating a disease or a condition associated with an antigen as identified earlier herein. Accordingly, there is further provided the use of a nucleic acid molecule as identified herein comprising a nucleic acid molecule encoding an adjuvant operably linked to a nucleic acid molecule encoding an antigen, a corresponding peptide, a corresponding polypeptide, a corresponding nucleic acid construct and/or a corresponding composition for the manufacture of a medicament being a vaccine for treating a disease or a condition associated with the antigen.

Each feature of this use has already been defined herein.

Method of Treatment

In a further aspect, there is provided a method of treatment of a disease or a condition associated with an antigen, wherein said treatment comprises a nucleic acid molecule encoding an adjuvant and a nucleic acid molecule encoding an antigen, a corresponding peptide, a corresponding polypeptide, a corresponding nucleic acid construct and/or a corresponding composition.

Accordingly, there is further provided a method of treatment of a disease or a condition associated with an antigen as identified herein, wherein said treatment comprises a vaccine, said vaccine comprising a nucleic acid molecule as identified herein comprising a nucleic acid molecule encoding an adjuvant operably linked to a nucleic acid molecule encoding an antigen, a corresponding peptide, a corresponding polypeptide, a corresponding nucleic acid construct and/or a corresponding composition.

Each feature of this method has already been defined herein.

Definitions

Sequence Identity

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Hybridization Conditions

Hybridization conditions for a nucleic acid molecule may have low or medium or high stringency (southern blotting procedures). Low or medium or high stringency conditions means pre-hybridization and hybridization at 42° C. in 5×SSPE, 0.3% SDS, 200 pg/ml sheared and denatured salmon sperm DNA, and either 25% or 35% or 50% formamide for low or medium or high stringencies respectively. Subsequently, the hybridization reaction is washed three times for 30 minutes each using 2×SSC, 0.2% SDS and either 55° C. or 65° C., or 75° C. for low or medium or high stringencies respectively.

Nucleic Acid Construct, Expression Vector, Operably Linked, Expression, Control Sequences A nucleic acid construct is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence (i.e. defined as an adjuvant) is appropriately placed at a position relative to another sequence coding for an antigen such that a chimeric polypeptide (i.e. comprising an adjuvant fused to an antigen) in a cell and/or in a subject is formed.

"Operably linked" refers to the genetic fusion of a sequence encoding a protein being able to behave as an adjuvant as defined herein to a sequence encoding an antigen as defined herein resulting in a chimeric nucleic acid sequence encoding a chimeric protein.

Expression will be understood to include any step involved in the production of the peptide or polypeptide including, but not limited to, transcription, post-transcriptional modification, translation, post-translational modification and secretion.

Control sequence is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIGS. 4.1 and 4.2. Solid phase Kmp11. Cytokine production in non-stimulated and in KAAP stimulated spleen cells from PBS, KAAP and pRcKAAP injected mice. The bars indicate the variation between triplicate determinations. The units indicated in the Y axis are given in pg/ml. In the X axis the vaccinated groups are indicated.

FIGS. 5.1 and 5.2. Solid phase Kmp11. Cytokine production in non-stimulated and in Kmp11 stimulated spleen cells from PBS, KAAP and pRcKAAP injected mice. The bars indicate the variation between triplicate determinations. The units indicated in the Y axis are given in pg/ml. In the X axis the vaccinated groups are indicated.

FIG. 14. Reactivity against S100A2 (In O.D. units) after a third immunization. The same group of animals indicated in FIG. 1 were immunized with S100AAP (1.05 µg), S100A2 (0.3 µg), AAP (0.75 µg of AAP) and S100A2+AAP (0.3 µg +0.75 m) 15 days after the administration of the second dose. The sera were obtained a week after. (a) IgG reactivity. (b) IgG1 reactivity. (c) IgG2a reactivity. The sera were analyzed at a dilution of 1/6400. The stars indicate statistical differences ($p<0.05$).

EXAMPLES

Figure 1:
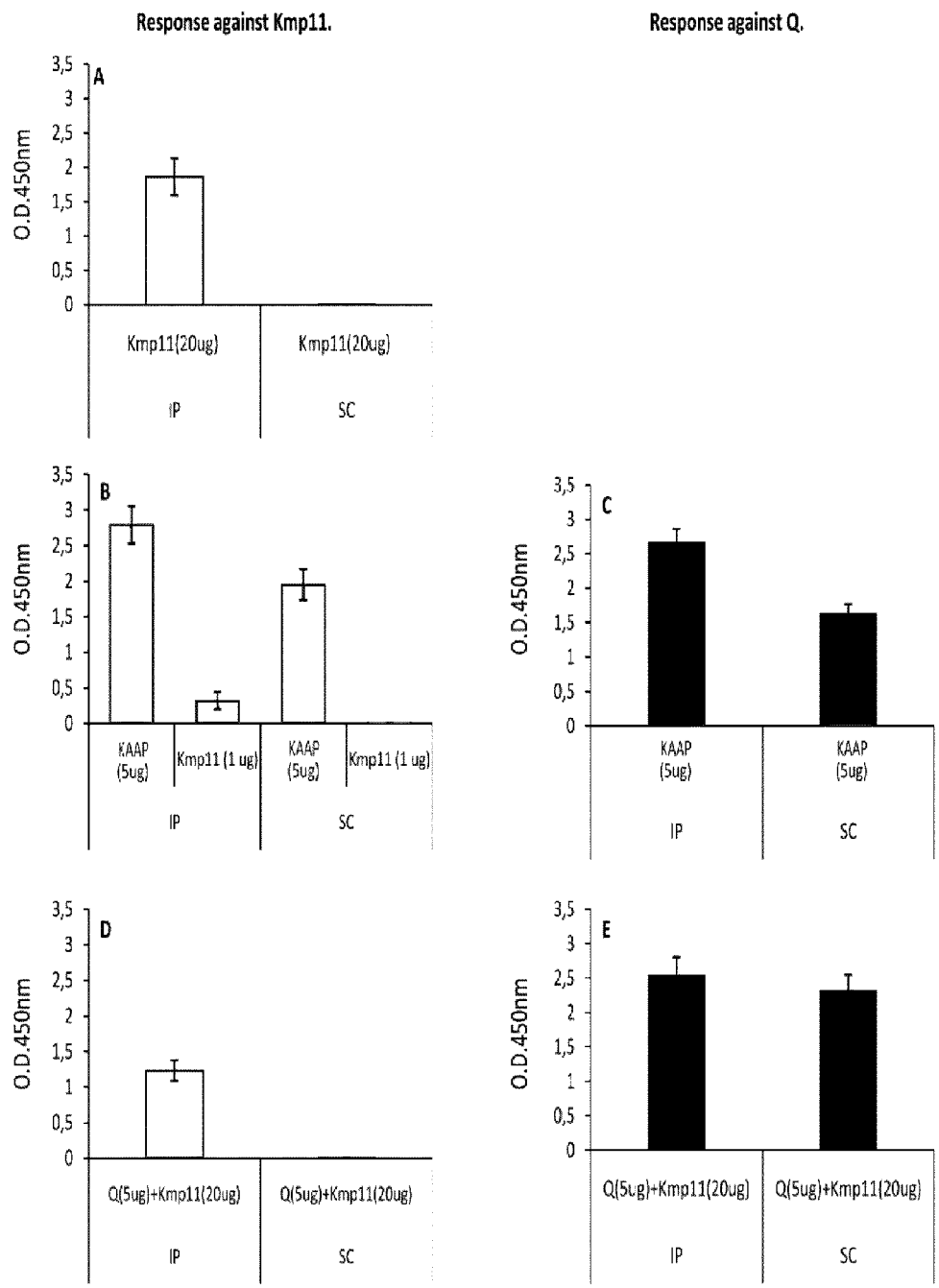
FIG. 1. Solid phase Kmp11. Humoral response against Kmp11 and against Q. A: IgG response against Kmp11 after ip and sc administration of Kmp11 (20 µg). B: IgG response against Kmp11 after ip and sc administration of KAAP (5 µg) and Kmp11 (1 µg). C: IgG response against Q after ip and sc administration of KAAP (5 µg). D: IgG response against Kmp11 after ip and sc administration of Q (5 µg)+Kmp11 (20 µg). E: IgG response against Q after ip and sc administration of Q (5 µg)+Kmp11 (20 µg). The bars indicate the response variability between the animals within a group.

Section I
Materials and Methods

Animals and immunization. Female 6-8-week-old BALB/c mice were purchased from Harlan Interfauna Ibérica S.A. (Barcelona, Spain). The immunization of the animals was done by an intraperitoneal (ip) or subcutaneous (sb) route as indicated in the legends of the Figures included in the Results Section. The mice were bled by orbital plexus puncture.

Construction of the DNA Plasmid Expressing the Chimeric Kmp11AAP Gene.

The DNA sequences coding for the amino and carboxyl terminal ends of the H2A antigenic determinants were removed from the chimeric clone pPQ (Soto M, et al. J Clin Microbiol. 1998 January; 36(1):58-63) by Bam HI digestion. The nucleic acid sequence of PQ or Q is represented by SEQ ID NO: 46. The amino acid sequence of PQ or Q is represented by SEQ ID NO: 47. The resulting clone without the sequences coding for H2A determinants was named pAAP (SEQ ID NO:2). The DNA sequence coding for the Kmp11 protein was obtained by PCR amplification of the DNA sequence coding for that protein present in plasmid pBLs-KMP-11 (Fuertes M. A., et al, J Biol Inorg Chem 6 (2001) 107-117) using as primers the forward 5' CGGGATCCTT-TAATGGCCACCACGTACGAGGAG3' (SEQ ID NO: 31) and the reverse 5'CGGGATCCCCCCTTGGATGGGTACT-GCGCAGC3' (SEQ ID NO: 32) oligonucleotides. Then, the PCR product coding for the Kmp11 protein was digested with Bam HI and inserted into pAAP (the Bam H1 digested pPQ clone lacking the H2A determinants) (SEQ ID NO:33). The resulting clone, called pKmp11AAP, was transformed into E. coli (strain M15). The chimeric purified protein expressed by the pKmp11AAP clone was called KAAP (SEQ ID NO:34). In the $10^{th}$-$12^{th}$ position a TTA triplet was included to avoid the selection of clones having an insertion of the sequence coding for Kmp11 in the reverse orientation. In the $9^{th}$-$11^{th}$ position a triplet coding for glycine was introduced to provide flexibility to the intersection between the Kmp11 protein and the protein fragment coded by pAAP.

Construction of Plasmid pRcKAAP.

To construct the DNA plasmid containing the DNA sequence coding for the KAAP protein, the pKmp11AAP plasmid indicated above was PCR amplified using as primers the forward 5'-CCCAAGCTTATGGCCACCACCTACGAG-GAG-3' (SEQ ID NO:35) and the reverse 5'-CATTACTG-GATCTATCAACAGG-3' (SEQ ID NO:36). The DNA sequence was inserted into a pRc/CMV Hind III digested plasmid. Plasmid pRC is commercially available by In vitrogen. The DNA plasmids were purified by an endotoxin free Giga-preparation Kit (Qiagen, Hilden, Germany).

Protein Purification.

The purification of the recombinant protein KAAP, expressed by clone pKmp11AAP, as well as the recombinant Q and Kmp11 proteins (Soto M, et al. J Clin Microbiol. (1998) January; 36(1):58-63, and Planelles L, et al, Immunol Cell Biol. (2002);80(3):241-7), was performed on Ninitrilotriacetic acid resin columns under denaturing conditions, according to the method provided by the supplier (Qiagen). Expression of the KAAP and Kmp11 Proteins by pRcKAAP.

COS7 cells were transfected with 20 µg of the pRcKmp11AAP or pRcKmp11 plasmids using the Lipofectin® Reagent (Gibco, BRL) according to the manufacturer's protocol. Briefly, $3\times10^6$ competent cells were seeded on 100 mm plates in Dulbecco's modified Eagle's medium plus 5% FCS and transfected when they reached 50-75% confluence. Seventy-two hours post-transfection, the cells were harvested, washed two times with ice-cold PBS and immediately lysed by addition of Laemmli's buffer. Proteins were resolved by sodium dodecyl sulphate-polyacrylamide gel electrophoresis (SDS-PAGE) and transferred to nitrocellulose membranes (Amersham, Aylesbury, UK). The blots were probed with a serum from mice immunized with the KAAP protein. A protein band of the expected size reacting with anti-KAAP was observed in the blots.

Analysis of the Humoral Response.

Serum samples were analyzed for specific antibodies against Q or Kmp11. Briefly, the wells of standard ELISA plates were coated overnight at room temperature with 100 µl of PBS containing 2 µg/ml Q or Kmp11. The IgG and the isotype-specific analysis was done using horseradish peroxidase-conjugated anti-mouse immunoglobulins (Nordic Immunological Laboratories, Tilburg, The Netherlands): Dilution of anti IgG and anti-IgG1 (1:1000) and anti-IgG2a (1:500). Ortophenylenediamine dihydrochloride—OPD—(Dako, A/S, Glostrup, Denmark) was used as substrate. After 15 min, the reaction was stopped by the addition of 100 µl of 1 M $H_2SO_4$. The absorbance was read at 450 nm.

Cytokine Analysis.

Spleens were removed from mice one week after the last immunization under aseptic conditions on a sterile dish containing DMEM medium. Single cell suspensions were prepared by grinding the spleen using an autoclaved mesh. 5-10 ml of DMEM medium was added to it and the contents were mixed to homogeneity. The clear supernatant was pipetted out slowly. Cells were pelleted by centrifugation at 4° C. at 250 g (Sorvall RC-5 centrifuge, HB-4 rotor) for 10 min. The pellet containing erythrocytes and splenocytes were collected. The pellet was washed once with 0.9% ammonium chloride to lyse the erythrocytes. The splenocytes from each mouse in a group were pooled and resuspended to a density of $10^7$ cells/ml in RPMI containing 10% FCS and 0.05 mM 2-mercaptoethanol, then divided into 200 ml aliquots ($5\times10^5$ cells) in 1.5 ml eppendorf tubes. The splenocytes were re-stimulated with 12 µg/ml KAAP or Kmp11. The cells were incubated for 48 hrs at 37° C. in atmosphere containing 5% CO2 and 95% humidity. The supernatants of the mice from each group (N=4) were pooled. All determinations were performed in triplicate. To control cell proliferation the amount of IFN-γ and IL-2 in the supernatants of ConA (3 µg/ml) treated cells were measured. High amounts of IFN-γ (1000 fold) and IL-2 (200 fold) were detected in ConA treated cells relative to untreated cells.

Cytokine determination. IL-4, IL-6, IFN-γ, TNF-α, IL-17 and IL-10 concentrations in cell culture supernatants were determined using a CBA kit (BD Biosciences, Singapore) according to manufacturer instructions. The results were acquired using FACS CALIBUR (BD Biosciences, Singapore) and analyzed using FCAP software.

Results

In order to know whether the protein coded by the amino acid sequence SEQ ID NO:1 (AAP) is able to increase or modify the humoral response to a covalently attached antigen such as Kmp11, a KAAP protein expressed by a chimeric gene formed by the genetic fusion of the AAP and Kmp11 DNAs was administered to mice. The AAP sequence is derived from the Q sequence previously described with the exception of the DNA coding for the amino and carboxyl terminal amino-acid fragments corresponding to the H2A antigens having a 75% identity. In the chimeric KAAP protein the Kmp11 protein represents 1/4 of the complete protein. An assay was designed in which two groups of 5 mice were injected each with three doses of 20 µg Kmp11, 5 µg KAAP and 20 µg Kmp11-5 µg Q on day 0, 15$^{th}$ and 30$^{th}$. The proteins were administered to mice via a subcutaneous (sc) or an intra-peritoneal (ip) route. One week after the administration of the third dose the IgG reactivity against Q and Kmp11 was determined by an ELISA test. FIG. 1A shows that the Kmp11 protein elicited high reactivity against Kmp11 when it was administered by an ip route but that it was not able to trigger an immune response when it was administered by a sc route. It was observed that after ip administration of 5 µg KAAP the response against Kmp11 was also high and similar to that observed when 20 µg of Kmp11 protein were administered alone and that, moreover, a high response was triggered after sc administration in contrast to the lack of response when 20 µg of Kmp11 were administered (FIG. 1B) alone by the same route. High response was observed against Q either when the KAAP protein was ip or sc administered (FIG. 1C).

Since a high response against Kmp11 was elicited when 5 µg of KAAP was administered and the amount of Kmp11 in 5 µg of KAAP is equivalent to about 1 µg of Kmp11, we tested whether 1 µg of Kmp11 was able to also induce a serological response. FIG. 1B shows that the protein is able to induce a slight humoral response against Kmp11 when is ip administered (mean OD=0.3) but that the response was significantly lower that that elicited after the administration of 5 µg of KAAP. It may be observed, moreover, that, as expected, there was not any reactivity against Kmp11 after sc administration of 1 µg Kmp11 but that, in contrast, the response was high after administration of the same amount of Kmp11 present in 5 µg of KAAP.

In order to know whether the increase in reactivity against Kmp11 was due to the co-administration of Kmp11 with the protein fragments present in the Q protein, the Kmp11 protein was administered mixed with Q. It was observed that the reactivity against Kmp11 decreased when the mix was administered ip and that no response was observed against Kmp11 when the mix was sc administered (FIG. 1D), as an indication that the protein fragments present in Q do not elicit any adjuvant effect on Kmp11. High serological reactivity was observed against Q (FIG. 1E).

Figure 2:
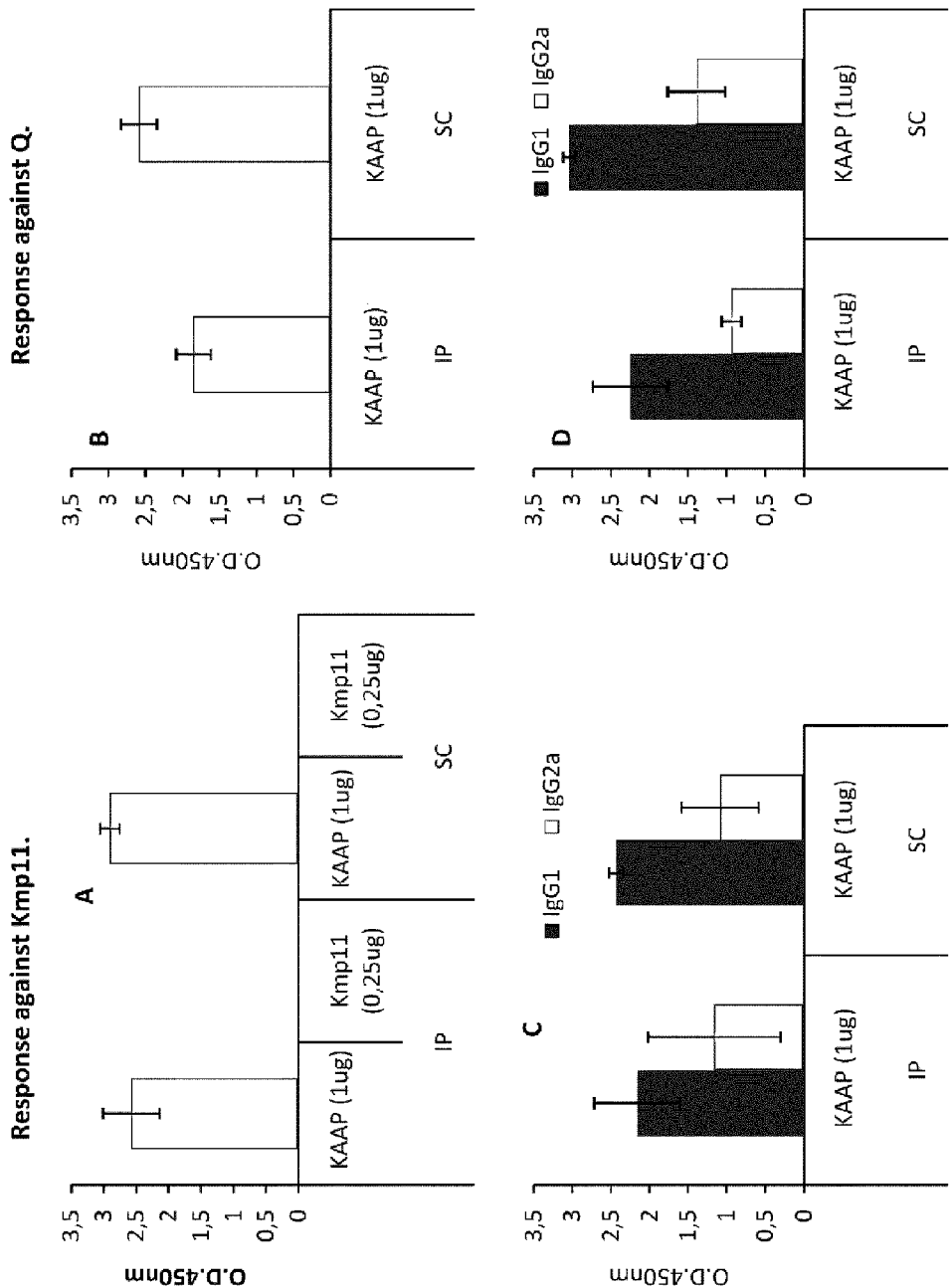
FIG. 2. Solid phase Kmp11. Humoral response against Kmp11 and against Q. A: IgG Humoral response against Kmp11 after administration of KAAP (1 µg) and Kmp11 (0.25 µg) via ip and sc. B: Humoral response against Q after administration of KAAP (1 µg) via ip and sc. C: IgG1 and IgG2a response against Kmp11 after ip and sc administration of KAAP (1 µg). D: IgG1 and IgG2a response against Q after ip and sc administration of KAAP (1 µg). The bars indicate the response variability between the animals within a group.

Due to the high serological response observed after administration of 5 µg KAAP, we analyzed the response against Q and Kmp11 after the administration of 1 µg of KAAP. Five mice were sc injected in the footpad on day 0 and 15$^{th}$. The IgG and IgG1/IgG2a response was analyzed one week after administration of the second dose. As a control, 0.25 µg of Kmp11, which is the amount present in 1 µg of KAAP, were administered to mice. FIG. 2A shows that high response against Kmp11 was obtained after administration of 1 µg KAAP either by ip or sc administration but that no response was obtained either after a sc or ip administration of 0.25 µg of Kmp11. High humoral response against Q was observed when the KAAP was administered either by an ip or sc route (FIG. 2B). The response was similar to that observed after administration of 3 µg and 5 µg of KAAP (data not shown). The type of response was predominantly of an IgG1 type either against Kmp11 or Q (FIGS. 2C and D) being the ratio IgG1/IgG2a of about 0.5.

Figure 3:
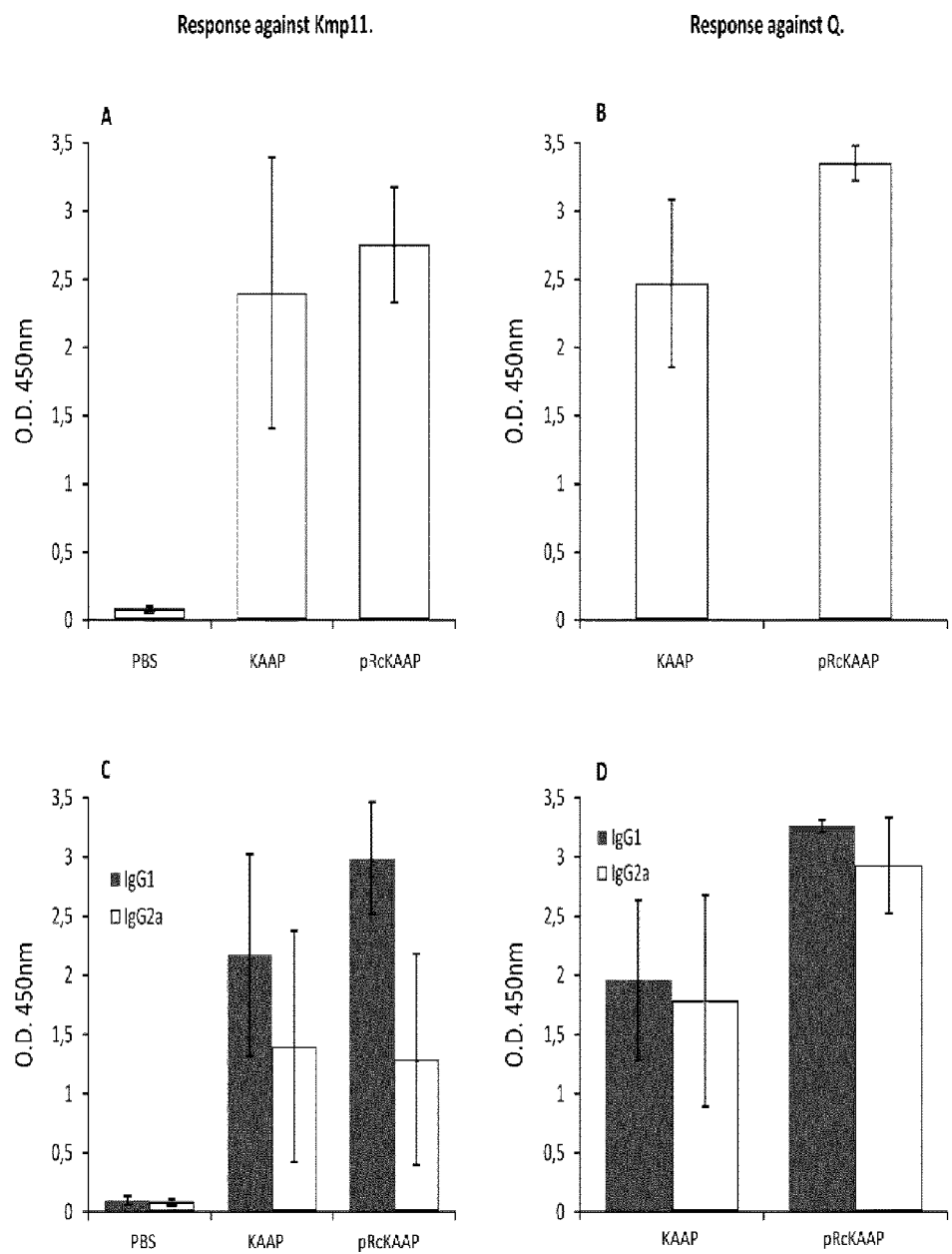
FIG. 3. Solid phase Kmp11. Humoral response against Kmp11 and against Q. A: IgG response against Kmp11 after sc administration of pRcKmp11 (20 µg), KAAP (3 µg) and pRcKAAP 20 µg). B: IgG response against Q after sc administration of KAAP (3 µg) and pRcKAAP (20 µg). C: IgG1 and IgG2a response against Kmp11 after sc administration of pRcKmp11 (20 µg), KAAP (3 µg) and pRcKAAP (20 µg). D: IgG1 and IgG2a response against Q after sc administration of KAAP (3 µg) and pRcKAAP (20 µg). The bars indicate the response variability between the animals within a group.

In order to know whether the KAAP protein is able to elicit a humoral response after administration to mice of a plasmid DNA containing the gene coding for KAAP the IgG, IgG1 and IgG2a humoral response against Q and Kmp11 was analyzed. Groups of 7 mice were injected in the footpad with 20 µg of pRcKQ1, 20 µg of pRcKmp11 and 3 µg of KAAP on day 0, 15$^{th}$ and 30$^{th}$. PBS was administered to control animals. FIG. 3 shows that high IgG reactivity against Kmp11 (FIG. 3A) and Q (FIG. 3B) was detected after administration of pRcKAAP and that it was similar to that detected after administration of the KAAP protein. However, no response was obtained after administration of the DNA plasmid containing the gene coding for Kmp11 protein alone. A balanced IgG1/IgG2a ratio was detected when the reactivity was analyzed against Q (FIG. 3D) either after KAAP or pRcKAAP administration. A slight predominance of the mean IgG1 reactivity was observed when tested against Kmp11 (FIG. 3C).

The cytokine production was analyzed in non-stimulated and in KAAP and Kmp11 stimulated spleen cells from KAAP and pRcKAAP injected mice. An antigen specific up-production of IFN-γ, IL-6, TNF-α and IL-10 was observed in KAAP stimulated cells isolated from pRcKAAP-immunized animals. No differences were detected in cytokine production by KAAP stimulated cells from PBS and KAAP-immunized mice. Since a similar increase in IL-6, TNF-α and IL-10 was detected in KAAP stimulated cells from PBS and KAAP immunized, most likely the increase in cytokine production relative to non-stimulated cells is due to an unspecific stimulation of the spleen cells rather than to a stimulation of KAAP specific cells. A similar production of IL-17 was observed in spleen cells from PBS, KAAP and pRcKAAP-immunized mice stimulated with KAAP (FIGS. 4.1 and 4.2). An up-production of IFN-γ and IL-17 was also observed after Kmp11 stimulation of spleen cells from pRcKAAP-immunized animals. Also an increase in IL-17 production was observed in cells from KAAP-immunized mice. In addition, an unspecific production of TNF-α, IFN-γ and IL-6 was observed in the cell cultures stimulated with Kmp11 relative to non-stimulated cells (FIGS. 5.1 and 5.2).

Conclusion:

The immunogenic potential of Kmp11 is highly increased when genetically fused to a chimeric protein formed by fragments from the Lip2a, Lip2b and P0 proteins from *Leishmania infantum*. A chimeric protein containing the Lip2a, Lip2b and P0 fragments mix (but not fused to) with Kmp11 does not increase the immunogenic potential of Kmp11.

The Kmp11 protein when administered as DNA fused to the DNA fragments coding for the antigenic determinants of Lip2a, Lip3b and P0 proteins from *Leishmania infantum* elicited a high humoral response. The Kmp11 protein when administered alone as DNA does not elicit a detectable humoral response.

An antigen specific up-production of IFN-γ, IL-6, TNF-α and IL-10 was observed in KAAP stimulated cells isolated from pRcKAAP-immunized animals. Also an up-production of IFN-γ was observed after stimulation with Kmp11. This type of up-production was not detected in KAAP stimulated cells isolated from KAAP-immunized animals.

The protein resulting from in vitro translation of the AAP DNA sequence may be used as a tool for promoting the generation of antibodies against a genetically fused protein. The AAP DNA sequence may be used as a vector to promote the immunogenic potential of an antigen when administered as DNA.

The AAP protein may be used as a carrier and as an adjuvant to elicit an immune response against a genetically fused antigen.

Section II

Materials and Methods

Construction of the CAAP Expression Vector (Cup a 4-AAP).

Figure 12:
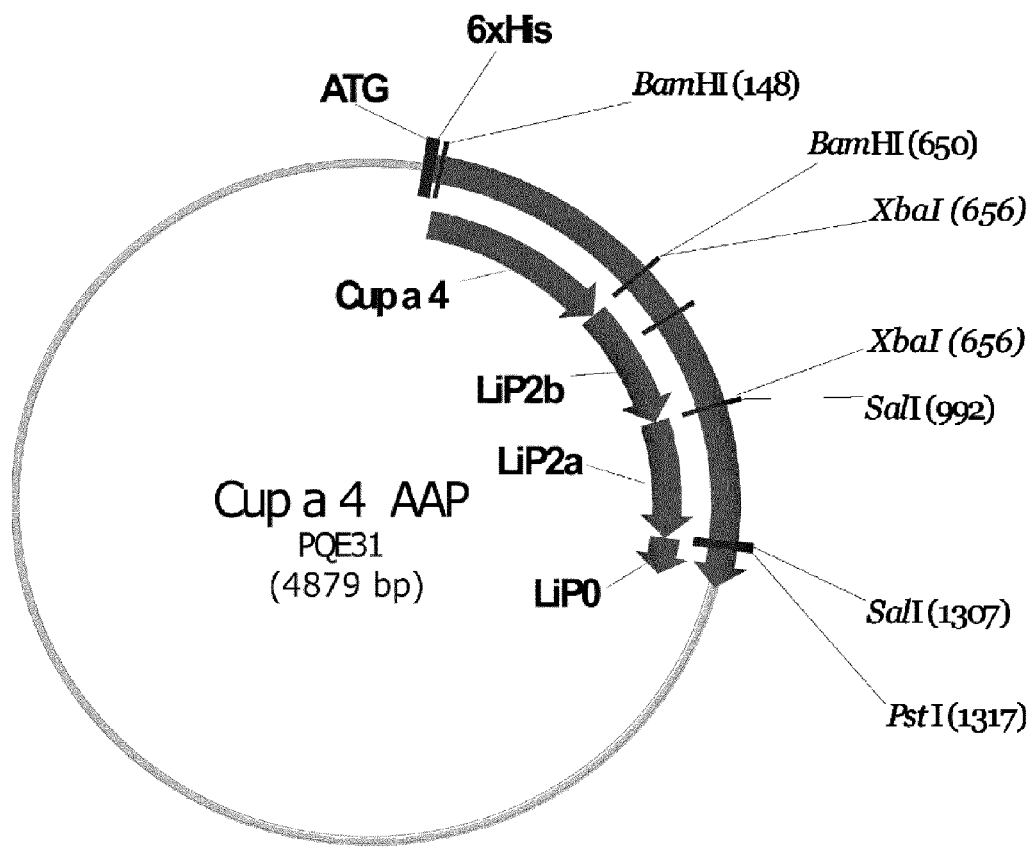
FIG. 12. Expression vector Cup a4 AAP

Cup a 4 had been previously cloned into the pQE-30 vector and expressed and purified as a recombinant protein (Molecular cloning and characterization of Cup a 4, a new allergen from *Cupressus arizonica*, Biochem Biophys Res Commun. 2010 Oct. 22; 401(3):451-7. Yago Pico de Coaña, Nuria Parody, Miguel Ángel Fuertes, Jerónimo Carnés, Daniela Roncarolo, Renato Ariano, Joaquín Sastre, Gianni Mistrello, Carlos Alonso). The protein was, then, inserted into the AAP vector that had been prepared after digestion of the KAAP quimeric protein with Bam HI in order to liberate the K (Kmp11) fragment (This patent). The resulting expression vector contains the AAP chimeric protein plus the Cup a 4 *C. arizonica* allergen (FIG. 12). The protein is called CAAP.

Expression and Purification of the CAAP Protein.

The vector coding for the CAAP protein (reporter protein) was transformed into the *E. coli* expression strain M15 (Qiagen). Expression was carried out in standard conditions after the addition of 1 mM IPTG during 5 hours to the bacterial culture that had been transformed with the CAAP vector. Purification of the protein was done as described previously for KAAP.

Results

In a previous section it was shown that the immune response of a poorly immunogenic protein is highly increased when fused to the AAP fragment. In order to know whether the AAP fragment could serve also as an adjuvant and, therefore, increase the immunogenic potential of a protein that it is highly immunogenic even in the absence of adjuvant, the CAAP vector was constructed. The Cup a 4 is an allergenic protein from *Cuppressus arizonica*. It has been described that in 10% of *Cuppressus* allergic patients an intense IgGE response is triggered against Cup a 4. To test whether AAP fused to Cup a 4 increases the immunogenicity of Cup a 4 a group of mice (N=5) was injected, each one, with 5 µg of the recombinant CAAP protein equivalent to 3 and 2 µg of AAP and Cup a 4, respectively. A second group of mice (N=5) was injected each one with a mix formed by 3 µg of AAP and 2µ of Cup a 4. A third group of mice (N=5) was injected each one with 2 µg of the Cup a 4 protein. To a fourth group 3 µg of AAP was administered. All proteins were dissolved in PBS and administered to mice via s.c. in the absence of any adjuvant.

Figure 6:
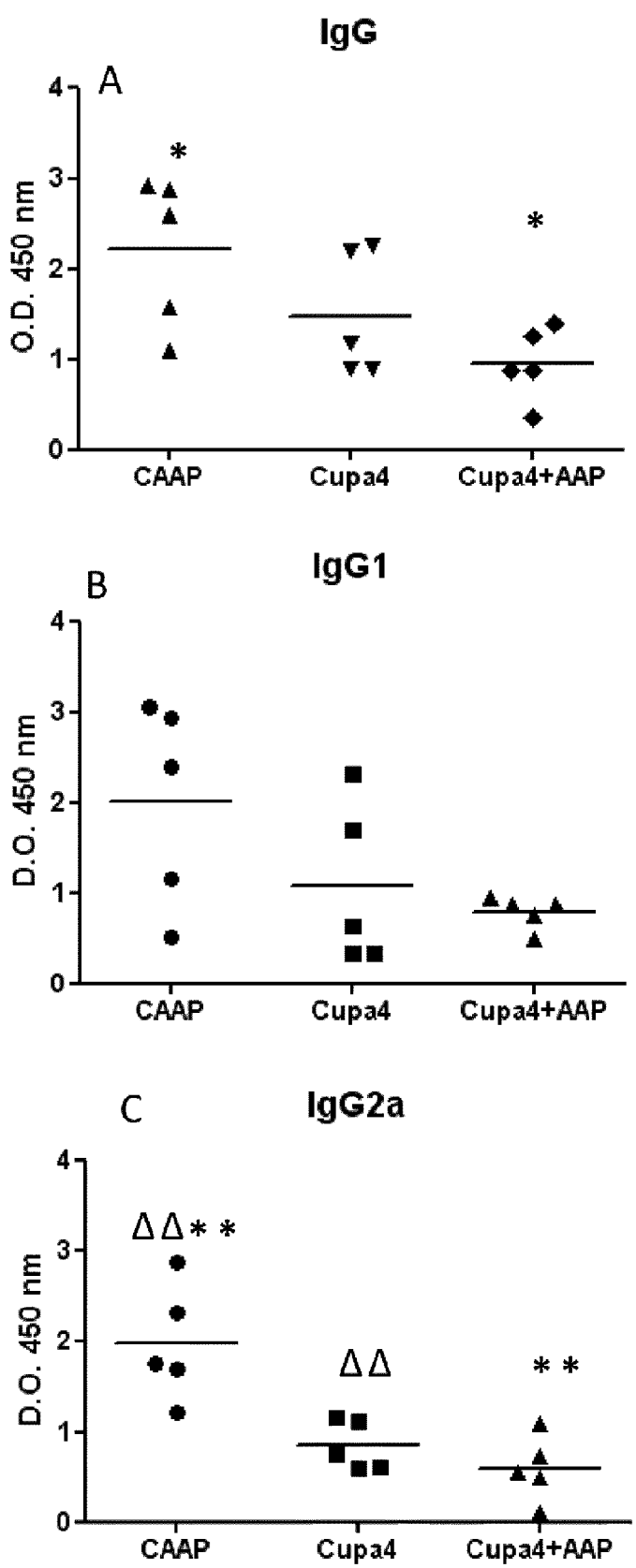
FIG. 6. Solid phase Cup a 4. Animals were immunized with three doses of PBS, 5 µg of CAAP; 2 µg of Cup a 4 and 2 µg Cup a 4+3 µg of AAP. A week after administration of the third dose sera were collected and analyzed for reactivity against Cup a 4. Panel A: IgG reactivity. Panel B: IgG1 reactivity. Panel C: IgG2a reactivity. The sera were tested at a dilution of 1/2000 for IgG and 1/1000 for IgG1 and IgG2a. Stars indicate statistical differences.

The IgG reactivity against Cup a 4 was determined at a dilution of 1/2000. As expected a week after administration of a third dose of PBS or AAP no response against Cup a 4 was observed (data not shown). The results of the IgG response a week after administrations of the third dose of Cup a 4, CAAP, Cup a 4+AAP and AAP are shown in FIG. 6A. It may be observed that in the Cup a 4 immunized animals an IgG response was elicited against Cup a 4 as expected from a highly immunogenic protein. The response was variable ranging from 0.9 to 2.3 with a mean value of 1.4 OD. A small decrease in reactivity against Cup a 4 was observed in the Cup a 4+AAP immunized animals. This indicates that the administration of AAP mixed with Cup a 4 did not increase the immunogenicity of Cup a 4 but that on the contrary AAP competes with Cup a 4. The mean value was 0.95 OD. However, when the Cup a 4 protein was administered fused to AAP (CAAP) an increase in response was observed in most of the animals. The response ranged from 1.1 to 2.9 OD with a mean value of 2.2 OD, in contrast to the 1.4 OD detected in the Cup a 4 immunized animals. A similar behaviour regarding the IgG response against Cup a 4 in the sera from the Cup a 4, Cup a 4+AAP and CAAP and AAP animals was observed one week after administration of the second dose (FIG. 7A) as a further indication of the intense immunogenic character of Cup a 4. In order to know whether the AAP has any influence in the modulation of the IgG1 and IgG2a response elicited against Cup a 4 the IgG1 and IgG2a isotype response was analyzed in the animals immunized with Cup a 4, Cup a 4+AAP and CAAP (dilution of the sera 1/400) one week after administration of the second and their dose.

Figure 7:
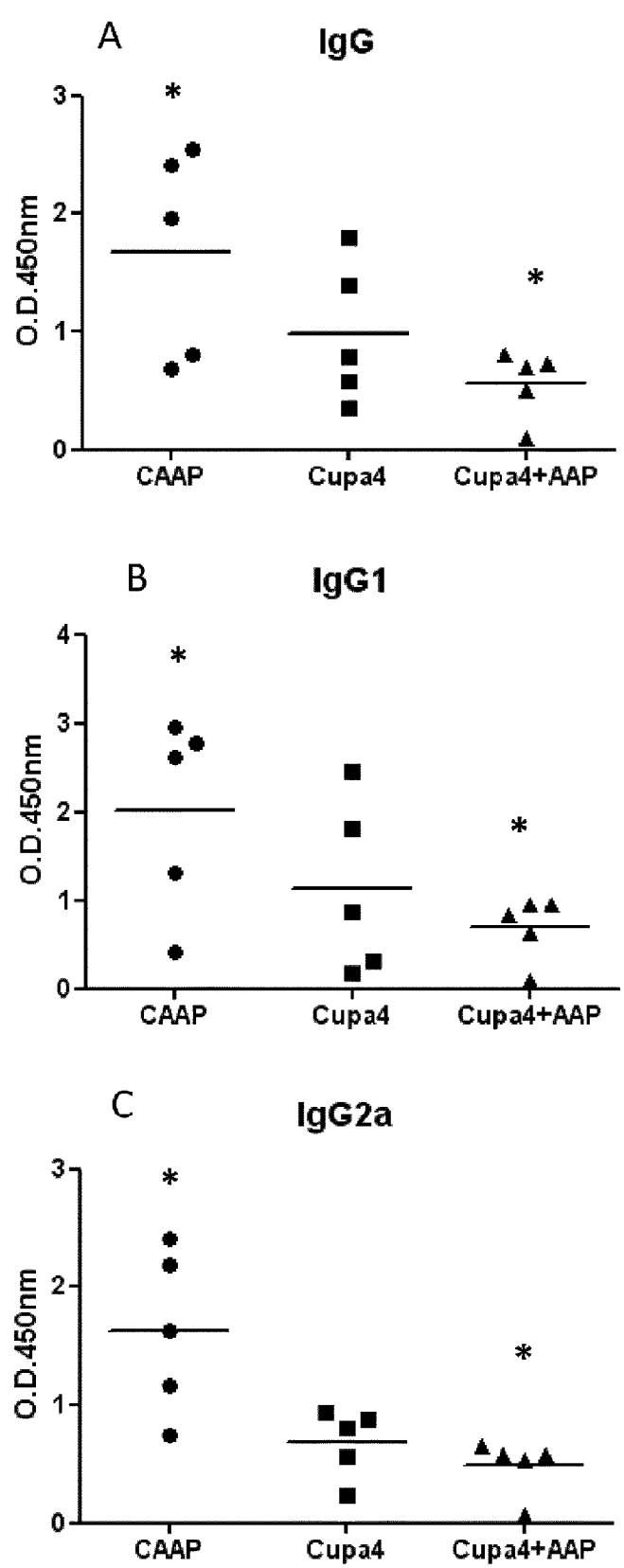
FIG. 7. Solid phase Cup a 4. Animals were immunized with two doses of PBS, 5 µg of CAAP; 2 µg of Cup a 4 and 2 µg of Cup a 4+3 µg of AAP. A week after administration of the second dose sera were collected and analyzed for reactivity against Cup a 4. Panel A: IgG reactivity; Panel B: IgG1 reactivity; Panel C: IgG2a reactivity. The sera were tested at a dilution of 1/1600 for IgG and 1/400 for IgG1 and IgG2a. Stars indicate statistical differences.

FIG. 7B shows that one week after the administration of the second dose of Cup a 4 also a dispersed intensity in IgG1 reactivity was detected ranging from 0.18 to 2.4 OD (mean value of 1.1). The IgG1 reactivity against Cup a 4 in the Cup a 4+AAP immunized animals was somewhat lower and uniform, around the mean value of 0.7 OD. In contrast the mean value of the IgG1 reactivity against Cup a 4 in the animals immunized with CAAP was higher (mean value of 2 OD), than that observed in the Cup a 4 and Cup a 4+AAP animals as a further indication that the AAP behaved as an adjuvant when fused to the antigen. Similar differences were also observed when the IgG1 reactivity against Cup a 4 was analyzed one week after the administration of the third dose (FIG. 6B), in particular when compared with the Cup a 4+AAP mixture was administered. When the intensity of the IgG2a reactivity against Cup a 4 was analyzed in the sera from animals immunized with Cup a 4, CAAP and Cup a 4+AAP one week after the third dose it was observed that in the sera of animals immunized with Cup a 4 and Cup a 4+AAP (FIG. 6C) the reactivity was uniform around a mean value of 0.8 and 0.6 OD, respectively. The IgG2a responses observed in the CAAP group, with values ranging from 1.1 to 2.9 OD and a mean value of 1.9 OD, were higher than those detected in the Cup a 4 and the Cup a 4+AAP animals. A similar observation was detected when the sera, obtained one week after the second dose, from the Cup a 4, Cup a 4+AAP and CAAP animals were analyzed (FIG. 7C).

Figure 8:
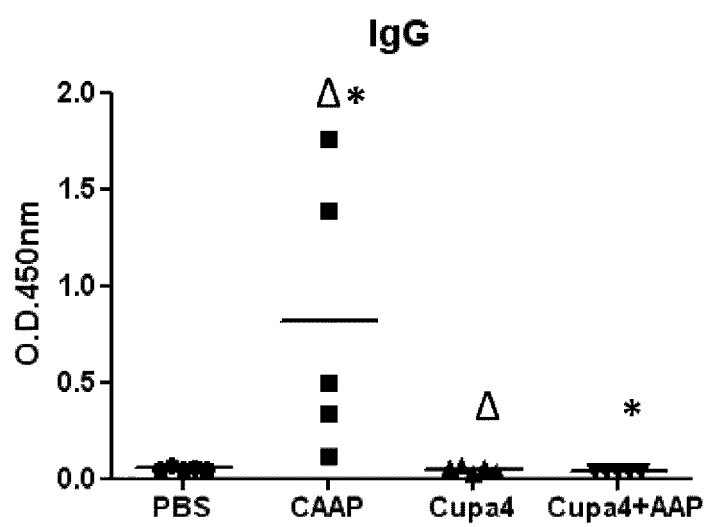
FIG. 8. Solid phase Cup a 4. IgG reactivity of the sera from animals immunized with a single dose of PBS, 1.25 µg CAAP; 0.5 µg of Cup a 4 and 0.5 µg of Cup a 4+0.75 µg of AAP. A week after administration of the dose sera were collected and analyzed for reactivity against Cup a 4. The sera were tested at a dilution of 1/100. Stars indicate statistical differences.
Figure 9:
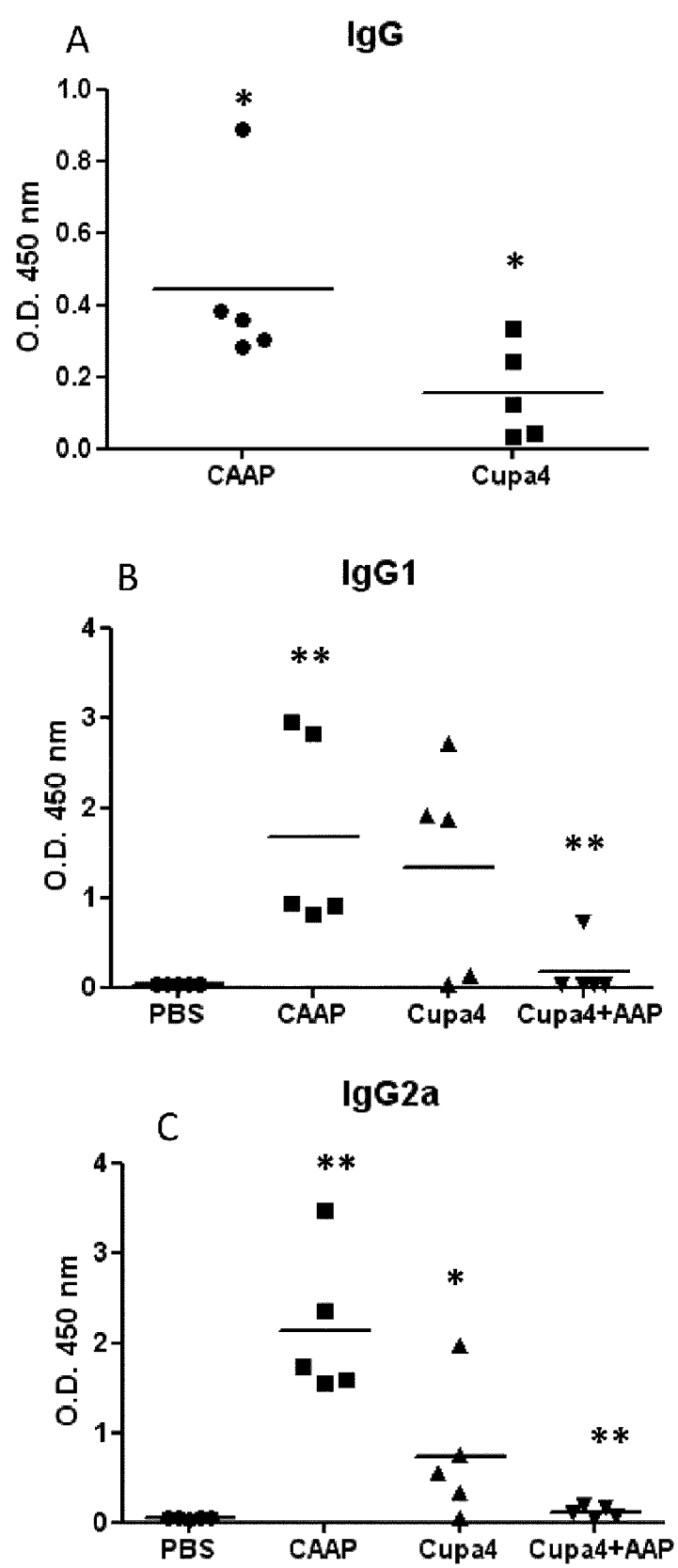
FIG. 9. Solid phase Cup a 4. Animals immunized with two doses of PBS, 1.25 µg CAAP; 0.5 µg of Cup a 4 and 0.5 µg of Cup a 4+0.75 µg of AAP. A week after administration of the second dose sera were collected and analyzed for reactivity against Cup a 4. Panel A: IgG; Panel B: IgG1; Panel C: IgG2a. The sera were tested at a dilution of 1/4000 for IgG and 1/100 for IgG1 and IgG2a. Stars indicate statistical differences.

To have a further evidence of the early adjuvant capacity of AAP a group of animals was immunized with 1/4 of the Cup a 4, CAAP and Cup a 4+AAP protein doses used in the experiment shown above (equivalent to 0.5 µg of Cup a 4, 1.5 µg CAAP and 0.5 µg Cup a 4+0.75 µg AAP, respectively). The sera were collected a week after the first dose. The IgG reactivity against Cup a 4 was determined at 1/100 dilution. The results are shown in FIG. 8. It was observed that while there was no response against Cup a 4 in any of the animals immunized with Cup a 4 or Cup a 4+AAP, positive responses were observed in all of the animals immunized with CAAP. Again it was observed that the response was variable ranged from 0.16 to 1.7 OD. Thus, with the exception of one animal the response was high in most of the animals at that early stage post immunization. After administration of a second dose an interesting result was also observed. In the Cup a 4+AAP group the response triggered by AAP competes with the response triggered by Cup a 4. In fact no reactivity against Cup a 4 was detected (FIG. 9A). Interestingly, this competition did not occur when the antigen was fused to AAP. In order to discriminate in detail the adjuvant capacity of AAP the sera were analyzed at a dilution of 1/4000 (FIG. 9A). The mean OD of the sera of animals immunized with CAAP was 0.45 OD while it was 0.15 OD in the sera from the Cup a 4 animals. In this group the reactivity of the sera against Cup a 4 of two animals was close to the background level. All the sera from the CAAP group of animals were positive. The difference between the reactivity against Cup a 4 in both groups was statistically different (p<0.05). When the IgG1 and IgG2a response was analyzed (dilution 1/100) the data shown above (FIGS. 7B and 7C) were confirmed (FIGS. 9B and 9C). The AAP when fused to the antigen directs the response towards IgG2a. The p value of the reactivity of the response against Cup a 4 due to administration of CAAP relative to Cup a 4 was 0.055 and relative to Cup a 4+AAP was p<0.05).

Thus, the data presented indicate that the AAP protein fragment when administered fused to Cup a 4 is able not only to increase the immune response against a highly immunogenic protein, such as Cup a 4, but it is also able to modulate the type of response elicited, in particular towards a IgG2a response. That type of adjuvant activity is not observed when AAP was administered mixed with protein Cup a 4. On the contrary, AAP seems to compete with the immune activity of the antigen.

Section III
Preparation of the S100AAP Expression Vector

Figure 13:
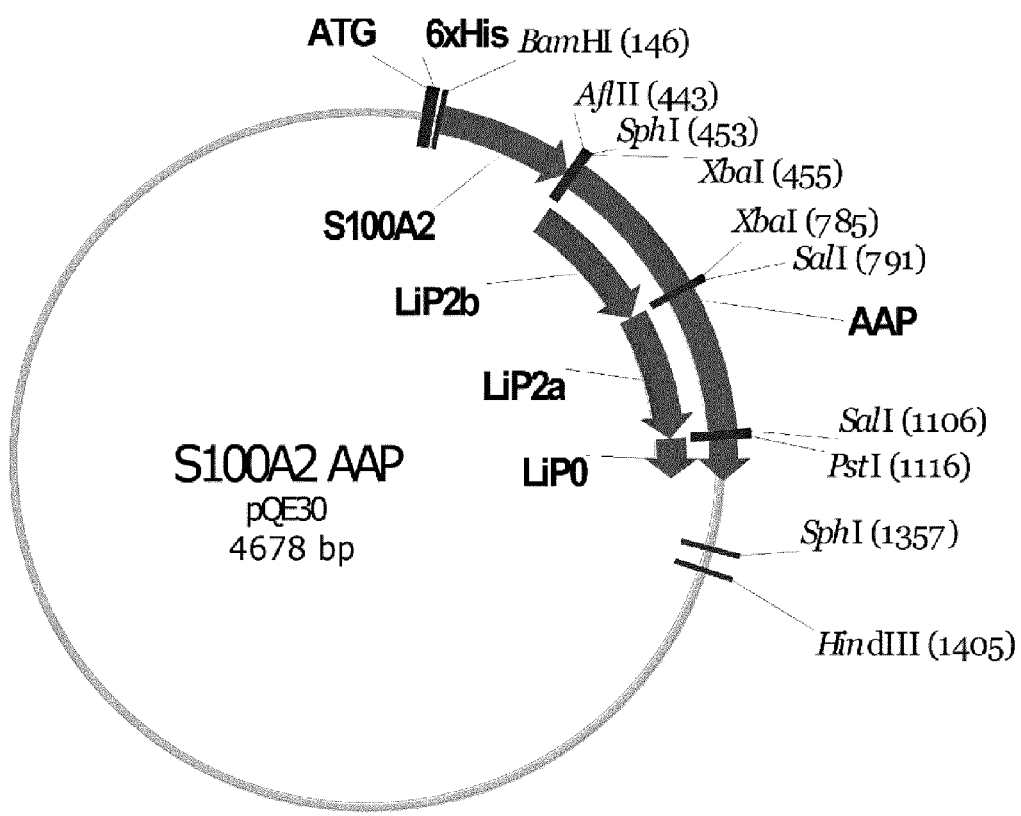
FIG. 13. Expression vector S100A2 AAP

After PCR amplification of the S100A2 DNA fragment in the Invitrogen pDEST-17 vector (Laboratory stock), using the 5'-AAGGATCCATGTGCAGTTCTCTGGAG-3' (SEQ ID NO: 44) and 5'-AACTTAAGCAGGGTCGGTCTGGGCAG-3' (SEQ ID NO: 45) primers, it was subcloned into a pST Blue-1 vector (the Bam HI and Afl II restriction sites are shown in italics). It was, then, subcloned into a modified AAP vector (in a PQE30 vector) that had been synthesized including the necessary restriction sites. The resulting expression vector contains the three fragments of the AAP chimeric protein plus the S100A2 DNA fragment (FIG. 13). This vector was transformed into the E. coli expression strain M15 (Qiagen). Expression was carried out in standard conditions: Induction of a 0.8 $O.D._{450nm}$ culture with 1 mM IPTG during 5 hours. The final vector was named S100AAP. The S100A2 protein was expressed in the PQE30 vector.

Figure 10:
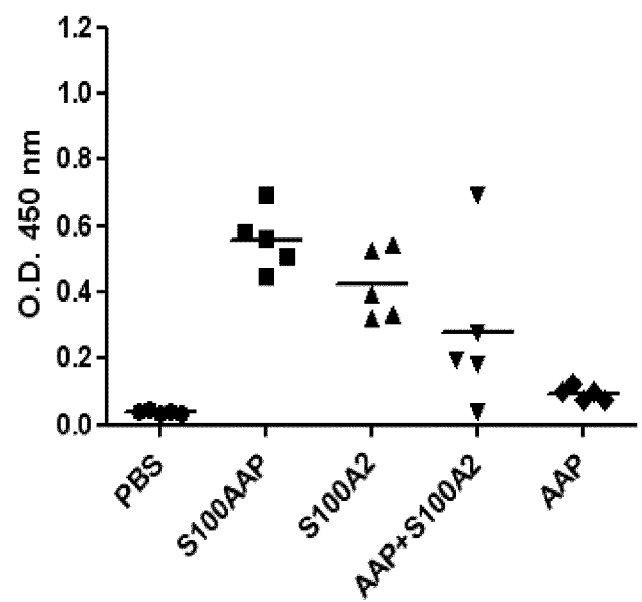
FIG. 10. Solid phase S100A2. Reactivity against S100A2 (In O.D. units). Four groups of animals (N=5) were immunized with a single dose of S100AAP (1.05 µg), S100A2 (0.3 µg), AAP (0.75 µg of AAP) and S100A2+AAP (0.3 µg+0.75 µg). PBS buffer was administered to another group of animals used as controls. The sera were obtained 15 days after administration of the proteins. The sera were analyzed at a dilution of 1/100

In previous sections it was shown that the immune response against a parasite poorly immunogenic protein (Kmp11) is highly increased when fused to the AAP DNA sequence and that the immune response against a plant highly immunogenic protein (Cup a4) is also increased when fused the AAP DNA sequence. It was also shown that the capacity of AAP to increase the immunogenicity of the reporter protein was only efficacious when the reporter protein was genetically fused to AAP. In order to know whether the AAP fragment could also serve as an adjuvant and, therefore, increase the immunogenic potential of a mammalian protein the S100AAP vector was constructed. The S100A2 protein is a calcium-binding protein that is up regulated in association with human gastric adenocarcinoma (1) and breast (2) tumour progression. To test whether AAP fused to S100 increases the immunogenicity of the reporter protein a group of mice (N=5) was injected, each one, with 1.05 µg of the recombinant S100AAP protein equivalent to 0.75 µg and 0.3 µg of AAP and S100A2, respectively. A second group of mice (N=5) was injected each one with a mixed formed by 0.75 µg of AAP and 0.3µ of S100A2. A third group of mice (N=5) was injected each one with 0.3 µg of S100A2. To a fourth group 0.75 µg of AAP were administered. All proteins were dissolved in PBS and administered to mice via s.c. As control another group of mice (N=5) were injected each one with a buffer solution (PBS). FIG. 10 shows the total IgG response against S100A2 at a dilution of 1/100 one week after administration of the first dose. As expected it was observed that neither the sera from the mice immunized with AAP or PBS showed any positive reactivity against S100A2. With the exception of one mouse the reactivity against S100A2 decreased when the protein was administered mixed to AAP as previously reported for Cup a4 as an indication of the competitive effect between two immunogenic proteins when administered as a mix (The reactivity of the serum of one animal was negative). The data from the mice immunized with the S100A2 protein alone indicated that that protein is also immunogenic in mice in the absence of adjuvant since even the low amount of protein administered was able to induce a low but positive response (mean OD=0.41). In spite of that it was observed that there was not any immune competition between AAP and S100A2 in mice immunized with S100AAP but that, on the other hand, the reactivity against S100A2 increased (30%) when the administered protein was fused to AAP (mean OD=0.54).

Figure 11:
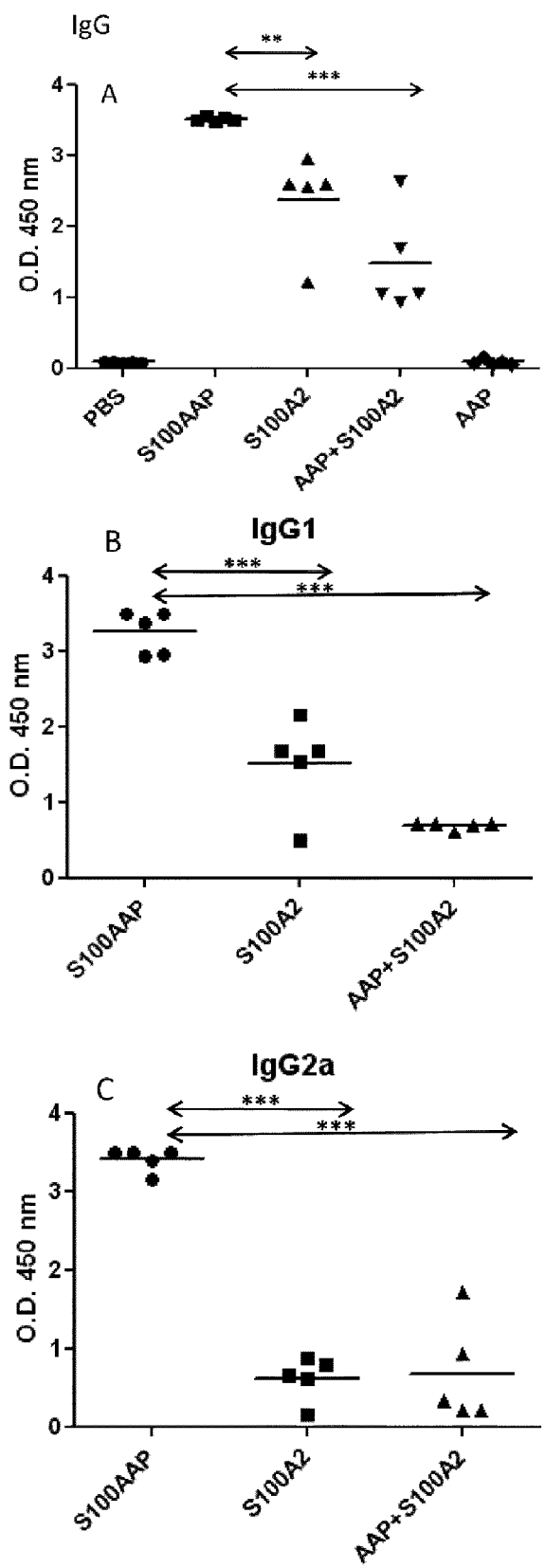
FIG. 11. Solid phase S100A2. Reactivity against S100A2 (In O.D. units). The same group of animals indicated in FIG. 1 were immunized with S100AAP (1.05 µg), S100A2 (0.3 µg), AAP (0.75 µg of AAP) and S100A2+AAP (0.3 µg+0.75 µg) 15 days after administration of the first dose. The sera were obtained a week after. (A) IgG reactivity. (B) IgG1 reactivity. (C) IgG2 reactivity. The sera were analyzed at a dilution of 1/200. The stars indicate high statistical differences.

As shown in FIG. 11A, the adjuvant capacity of AAP when fused to the protein reporter was clearly observed after the administration of a second dose of S100AAP, S100A2, AAP+ S100A2 and AAP (1.05 µg de S100AAP; 0.3 µg de S100A2; 0.75 µg of AAP plus 0.3 µg of S100A2 and 0.75 µg of AAP). A statistically significant difference in reactivity against S100A2 between the sera of the animals immunized with S100AAP and of those immunized with the S100A2 protein alone was detected. In agreement with the observations indicated above regarding the reactivity against Kmp11 and Cup a4 after administration of AAP non fused to the reporter proteins it was detected that AAP did not have any adjuvant capacity when non fused to the reporter S100A2 protein. On the other hand an immune competition between both proteins also seems to occur. Thus, an immunologically interesting feature may be deduced from the three experimental designs since AAP needs to be fused to the reporter protein to exercise the adjuvant effect. In other words this mean that the built-in adjuvant capacity of AAP is relevant when genetically fused to the reporter protein. The adjuvant effect was further observed when the type of response was analyzed (FIG. 11B). It was detected that not only the IgG reactivity against S100A2 increased after administration of the S100AAP relative to the reactivity against S100A2 after administration of S100A2 or AAP+S100A2 but that this increase in reactivity was also observed when the IgG2a type was analyzed. The IgG1/IgG2a reactivity ratio observed after administration of S100A2 had a mean value of 2.1 while it was 0.95 when the animals were immunized with S100AAP as indication that the adjuvant capacity of AAP when fused to the reporter protein triggers the IgG1-IgG2a response towards IgG2a. In agreement with the observations indicated above regarding the IgG response when the animals were immunized with a protein mix it was observed that the IgG1 reactivity of the sera of the animals immunized with S100AAP was significantly higher than the sera form the animals immunized with AAP+ S100A2. The mean of the IgG2a response in both cases was similar as a further in indication of the capacity of AAP to revert toward IgG2a only when fused to the reporter protein.

1—Identification of potential biomarkers for early and advanced gastric adenocarcinoma detection. Economescu M C, Necula L G, Dragu D, Badea L, Dima S O, Tudor S, Nastase A, Popescu I, Diaconu C C. Hepatogastroenterology. 2010 November-December; 57(104): 1453-64.

2—McKiernan E, McDermott E W, Evoy D, Crown J, Duffy M J. The role of S100 genes in breast cancer progression. Tumour Biol. 2011 June; 32(3):441-50

The adjuvant capacity of AAP in relation to S100A2 is further, even more clearly, observed alter administration of the third dose as indicated:

As a further indication of the adjuvant capacity of AAP the sera of the same animals obtained after the administration of a third dose of the antigens were analyzed. FIG. 14 shows the response against S100A2. After a titration curve of the dilution of the sera used for analysis a dilution of 1/6400 was chosen since it is the dilution that better discriminate the adjuvant capacity of AAP. It was clearly detected that the reactivity against S100A2 of the sera of the animals immunized with S100AAP is significantly higher than that observed in the sera of the animals immunized with either the mix of the S100A2 protein. In order to know whether the AAP modulates the humoral response the IgG1 and IgG2a response was analyzed. It was observed that an increase was observed in both types of responses. When the protein was administered alone the IgG2a/IgG1 mean ratio was 0.45. However, the mean ratio between IgG2a/IgG1 was 1.6 when AAP was fused to S100A2 as an indication that AAP modulates the response towards IgG2a. It should be noticed, in addition that AAP also modulates the response towards IgG2a when is administered mixed to S100A2 (IgG2a/IgG1 mean ratio equivalent to 1.1).

SEQ ID NO: 2
GGATCCTCTAGACCCATGTCCACCAAGTACCTCGCCGCGTACGCTCTGGC
CTCCCTGAGCAAGGCGTCCCCGTCTCAGGCGGACGTGGAGGCTATCTGCA
AGGCCGTCCACATCGACGTCGACCAGGCCACCCTCGCCTTTGTGATGGAG
AGCGTTACGGGACGCGACGTGGCCACCCTGATCGCGGAGGGCGCCGCGAA
GATGAGCGCGATGCCGGCGGCCAGCTCTGGTGCCGCTGCTGGCGTCACTG
CTTCCGCTGCGGGTGATGCGGCTCCGGCTGCCGCCGCTGCTAAGAAGGAC
GAGCCGGAGGAGGAGGCCGACGACGACATGGGCCCCTCTAGAGTCGACCC
CATGCAGTACCTCGCCGCGTACGCCCTCGTGGCGATGTCTGGCAAGACGC
CGTCGAAGGCGGACGTTCAGGCTGTCCTGAAGGCCGCCGGCGTTGCCGTG
GATGCCTCCCGCGTGGATGCCGTCTTCCAGGAGGTGGAGGGCAAGAGCTT
CGATGCGCTGGTGGCCGAGGGCCGCACGAAGCTGGTGGGCTCTGGCTCTG
CCGCTCCTGCTGGCGCTGTCTCCACTGCTGGTGCCGGCGCTGGCGCGGTG
GCCGAGGCGAAGAAGGAGGAGCCCGAGGAGGAGGAGGCCGATGATGACAT
GGGCCCCGTCGACCTGCAGCCCGCCGCTGCCGCGCCGGCCGCCCCTAGCG
CCGCTGCCAAGGAGGAGCCGGAGGAGAGCGACGAGGACGACTTCGGCATG
GGCGGTCTCTTCTAA

SEQ ID NO: 1
GSSRPMSTKYLAAYALASLSKASPSQADVEAICKAVHIDVDQATLAFVME
SVTGRDVATLIAEGAAKMSAMPAASSGAAAGVTASAAGDAAPAAAAAKKD
EPEEEADDDMGPSRVDPMQYLAAYALVAMSGKTPSKADVQAVLKAAGVAV
DASRVDAVFQEVEGKSFDALVAEGRTKLVGSGSAAPAGAVSTAGAGAGAV
AEAKKEEPEEEEADDDMGPVDLQPAAAAPAAPSAAAKEEPEESDEDDFGM
GGLF

---

The invention claimed is:

1. A nucleic acid molecule having a nucleotide sequence selected from the group consisting of:
   i. nucleotide sequences encoding a polypeptide comprising an amino acid sequence that has at least 50% sequence identity with the amino acid sequence of SEQ ID NO:1 over its entire length,
   ii. nucleotide sequences comprising a nucleotide sequence that has at least 50% sequence identity with the nucleotide sequence of SEQ ID NO:2 over its entire length,
   iii. nucleotide sequences the complementary strand of which hybridizes to a nucleic acid molecule of sequence of (i) or (ii) and
   iv. nucleotide sequences which differ from the nucleotide sequence of (iii) due to the degeneracy of the genetic code,
   wherein said nucleotide sequence is operably linked to a nucleotide sequence encoding an antigen, and wherein said nucleic acid molecule is free of a sequence encoding for a polypeptide identical to SEQ ID NO: 3 over its entire length.

2. A nucleic acid molecule according to claim 1, wherein the nucleic acid molecule encodes a polypeptide which is able to elicit an antigen-specific immune response in a subject.

3. A nucleic acid molecule according to claim 1, wherein said antigen:
   is specific for a disease or condition in a subject,
   is any antigen that originates from an organism that causes a disease or condition in a subject,
   comprises an allergen or
   comprises a cancer antigen.

4. A nucleic acid molecule according to claim 1, wherein said antigen is a self or auto antigen or originates from virus or a microorganism such as a bacterium, a yeast, a fungus or a parasite.

5. A polypeptide encoded by a nucleic acid molecule as identified in claim 1.

6. A vector comprising a nucleic acid molecule as identified in claim 1.

7. A composition comprising a nucleic acid molecule as identified in claim 1 and a pharmaceutical carrier.

8. A vaccine comprising a nucleic acid molecule according to claim 1.

9. Method of treatment of a disease or a condition in a subject wherein an antigen as identified in claim 1:
   is specific for said disease or condition
   is any antigen that originates from an organism that causes said disease or condition in the subject,
   comprises an allergen causing an allergy if said disease or condition is said allergy or
   comprises a cancer antigen associated with a cancer if said disease or condition is said cancer,
   wherein said treatment comprises administering to the subject a nucleic acid molecule as identified in claim 1.

10. Method of treatment of a disease or a condition in a subject wherein an antigen as identified in claim 1:
   is specific for said disease or condition
   is any antigen that originates from an organism that causes said disease or condition in the subject,
   comprises an allergen causing an allergy if said disease or condition is said allergy or
   comprises a cancer antigen associated with a cancer if said disease or condition is said cancer,
   wherein said treatment comprises administering to the subject a vaccine comprising a nucleic acid molecule as identified in claim 1.

11. A composition comprising a polypeptide as identified in claim 5 and a pharmaceutical carrier.

12. A composition comprising a vector as identified in claim 6 and a pharmaceutical carrier.

13. Method of treatment of a disease or a condition in a subject wherein an antigen as identified in claim 5:
   is specific for said disease or condition
   is any antigen that originates from an organism that causes said disease or condition in the subject,
   comprises an allergen causing an allergy if said disease or condition is said allergy or
   comprises a cancer antigen associated with a cancer if said disease or condition is said cancer,
   wherein said treatment comprises administering to the subject a polypeptide as identified in claim 5.

14. Method of treatment of a disease or a condition in a subject wherein an antigen as identified in claim 6:
   is specific for said disease or condition
   is any antigen that originates from an organism that causes said disease or condition in the subject,
   comprises an allergen causing an allergy if said disease or condition is said allergy or
   comprises a cancer antigen associated with a cancer if said disease or condition is said cancer,
   wherein said treatment comprises administering to the subject a vector as identified in claim 6.

15. Method of treatment of a disease or a condition in a subject wherein an antigen as identified in claim 7:
   is specific for said disease or condition
   is any antigen that originates from an organism that causes said disease or condition in the subject,
   comprises an allergen causing an allergy if said disease or condition is said allergy or
   comprises a cancer antigen associated with a cancer if said disease or condition is said cancer,
   wherein said treatment comprises administering to the subject a composition according to claim 7.

16. Method of treatment of a disease or a condition in a subject wherein an antigen as identified in claim 11:
   is specific for said disease or condition
   is any antigen that originates from an organism that causes said disease or condition in the subject,
   comprises an allergen causing an allergy if said disease or condition is said allergy or
   comprises a cancer antigen associated with a cancer if said disease or condition is said cancer,
   wherein said treatment comprises administering to the subject a composition according to claim 11.

* * * * *